US011773176B2

(12) United States Patent
Cha

(10) Patent No.: US 11,773,176 B2
(45) Date of Patent: *Oct. 3, 2023

(54) MULTISPECIFIC ANTIBODIES, COMPOSITIONS COMPRISING THE SAME, AND VECTORS AND USES THEREOF

(71) Applicant: APRILBIO CO., LTD., Chuncheon-si (KR)

(72) Inventor: Sang Hoon Cha, Chuncheon-si (KR)

(73) Assignee: APRILBIO CO., LTD., Chuncheon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,227

(22) Filed: Jan. 6, 2023

(65) Prior Publication Data

US 2023/0220093 A1 Jul. 13, 2023

Related U.S. Application Data

(63) Continuation of application No. 17/759,313, filed as application No. PCT/IB2021/050519 on Jan. 23, 2021, which is a continuation-in-part of application No. 16/878,255, filed on May 19, 2020, now abandoned.

(30) Foreign Application Priority Data

Jan. 24, 2020 (KR) .................. 10-2020-0009565

(51) Int. Cl.
*C07K 16/28* (2006.01)
*C07K 16/18* (2006.01)
*C07K 16/24* (2006.01)

(52) U.S. Cl.
CPC .......... *C07K 16/2875* (2013.01); *C07K 16/18* (2013.01); *C07K 16/241* (2013.01); *C07K 16/244* (2013.01); *C07K 16/249* (2013.01); C07K 2317/31 (2013.01); C07K 2317/55 (2013.01); C07K 2317/622 (2013.01); C07K 2317/92 (2013.01); C07K 2317/94 (2013.01)

(58) Field of Classification Search
None
See application file for complete search history.

(56) References Cited

U.S. PATENT DOCUMENTS

| 5,474,771 A | 12/1995 | Lederman et al. |
| 5,652,138 A | 7/1997 | Burton et al. |
| 5,804,440 A | 9/1998 | Burton et al. |
| 5,993,816 A | 11/1999 | Lederman et al. |
| 6,255,455 B1 | 7/2001 | Siegel |
| 6,331,615 B1 | 12/2001 | Lederman et al. |
| 6,340,459 B1 | 1/2002 | Yellin et al. |
| 6,403,091 B1 | 6/2002 | Lederman et al. |
| 6,451,310 B1 | 9/2002 | Lederman et al. |
| 6,592,868 B1 | 7/2003 | Lederman et al. |
| 6,610,294 B1 | 8/2003 | Lederman et al. |
| 6,858,719 B2 | 2/2005 | Siegel |
| 7,070,777 B1 | 7/2006 | Lederman et al. |
| 7,709,219 B2 | 5/2010 | Siegel |
| 8,101,553 B1 | 1/2012 | Kurosawa et al. |
| 8,124,742 B2 | 2/2012 | Siegel |
| 8,214,785 B2 | 7/2012 | Kouzaki et al. |
| 8,293,237 B2 | 10/2012 | Burkly et al. |
| 8,623,594 B2 | 1/2014 | Siegel |
| 8,647,625 B2 | 2/2014 | Vlijmen et al. |
| 8,705,130 B2 | 4/2014 | Miyazaki |
| 8,709,219 B2 | 4/2014 | Liu |
| 8,771,695 B2 | 7/2014 | Rothe et al. |
| 8,846,867 B2 | 9/2014 | Payne et al. |
| 8,858,948 B2 | 10/2014 | Grandea, III et al. |
| 8,916,160 B2 | 12/2014 | Grandea, III et al. |
| 8,968,736 B2 | 3/2015 | Croll et al. |
| 8,974,788 B2 | 3/2015 | Grandea, III et al. |
| 9,000,131 B2 | 4/2015 | Marks et al. |
| 9,101,760 B2 | 8/2015 | Hettmann et al. |
| 9,175,082 B2 | 11/2015 | Zhou et al. |
| 9,249,230 B2 | 2/2016 | Rothe et al. |
| 9,403,901 B2 | 8/2016 | Digiandomenico et al. |
| 9,441,034 B2 | 9/2016 | Sivakumar et al. |
| 9,453,068 B2 | 9/2016 | Marks et al. |
| 9,522,185 B2 | 12/2016 | Croll et al. |
| 9,567,399 B1 | 2/2017 | Campbell et al. |
| 9,617,338 B1 | 4/2017 | Campbell et al. |
| 9,657,102 B2 | 5/2017 | Smith et al. |

(Continued)

FOREIGN PATENT DOCUMENTS

| CN | 101031588 A | 9/2007 |
| EP | 1034001 B1 | 8/2004 |

(Continued)

OTHER PUBLICATIONS

Bang, Y. et al., "A novel bispecific anti-CD40L antibody, APB-A1, shows the potent immunosuppressive effect through blocking CD40-CD40L interaction," PEGS Europe, Nov. 9-13, 2020, AprilBio Co., LTD.

(Continued)

*Primary Examiner* — Adam Weidner

(74) *Attorney, Agent, or Firm* — Potomac Law Group, PLLC

(57) ABSTRACT

The present disclosure provides multispecific antibodies having increased in vivo sustainability, the multispecific antibodies comprising one or more bioactive effector moieties linked to either or both of an N-terminal and a C-terminal of an antigen binding fragment Fab that binds to human serum albumin.

19 Claims, 46 Drawing Sheets
Specification includes a Sequence Listing.

(56) References Cited

U.S. PATENT DOCUMENTS

| | | |
|---|---|---|
| 9,670,272 B2 | 6/2017 | Nitsch et al. |
| 9,708,390 B2 | 7/2017 | Sivakumar et al. |
| 9,718,872 B2 | 8/2017 | Kyratsous et al. |
| 9,718,881 B2 | 8/2017 | Gromada et al. |
| 9,771,414 B2 | 9/2017 | Kyratsous et al. |
| 9,796,788 B2 | 10/2017 | McWhirter et al. |
| 9,803,025 B2 | 10/2017 | Hettmann et al. |
| 9,840,557 B2 | 12/2017 | Orengo et al. |
| 9,879,077 B2 | 1/2018 | Cha |
| 9,938,345 B2 | 4/2018 | Papadopoulos et al. |
| 9,957,323 B2 | 5/2018 | Sainson et al. |
| 9,969,814 B2 | 5/2018 | McWhirter et al. |
| 9,987,500 B2 | 6/2018 | Papadopoulos et al. |
| 9,988,462 B2 | 6/2018 | Hettmann et al. |
| 10,023,644 B2 | 7/2018 | Gromada et al. |
| 10,058,609 B2 | 8/2018 | Zhou et al. |
| 10,106,618 B2 | 10/2018 | Lincecum et al. |
| 10,618,953 B2 | 4/2020 | Cha |
| 2002/0062010 A1 | 5/2002 | Arathoon et al. |
| 2003/0040605 A1 | 2/2003 | Siegel |
| 2004/0120951 A1 | 6/2004 | Nakashima et al. |
| 2005/0118161 A1 | 6/2005 | Laukkanen et al. |
| 2005/0282252 A1 | 12/2005 | Siegel |
| 2006/0115477 A1 | 6/2006 | Unger et al. |
| 2006/0177440 A1 | 8/2006 | Siegel |
| 2006/0286112 A1 | 12/2006 | Kellermann et al. |
| 2007/0059301 A1 | 3/2007 | Humphreys et al. |
| 2008/0124345 A1 | 5/2008 | Rothe et al. |
| 2009/0111745 A1 | 4/2009 | Tomlinson |
| 2009/0123475 A9 | 5/2009 | Siegel |
| 2010/0183631 A1 | 7/2010 | Rothe et al. |
| 2010/0196398 A1 | 8/2010 | Gazit-Bornstein et al. |
| 2010/0202968 A1 | 8/2010 | Nitsch et al. |
| 2011/0033476 A1 | 2/2011 | Grandea, III et al. |
| 2011/0070235 A1 | 3/2011 | Grandea, III et al. |
| 2011/0091449 A1 | 4/2011 | Payne et al. |
| 2011/0091960 A1 | 4/2011 | Siegel |
| 2011/0177074 A1 | 7/2011 | Sivakumar et al. |
| 2011/0182809 A1 | 7/2011 | Nitsch et al. |
| 2011/0195454 A1 | 8/2011 | McWhirter et al. |
| 2011/0200615 A1 | 8/2011 | Marks et al. |
| 2011/0229406 A1 | 9/2011 | Dettmann et al. |
| 2011/0274685 A1 | 11/2011 | Keler et al. |
| 2012/0021409 A1 | 1/2012 | McWhirter et al. |
| 2012/0058117 A1 | 3/2012 | Unger et al. |
| 2012/0058122 A1 | 3/2012 | Rothe et al. |
| 2012/0121603 A1 | 5/2012 | Grandea, III et al. |
| 2012/0156130 A1 | 6/2012 | Hettmann et al. |
| 2012/0192300 A1 | 7/2012 | Babb et al. |
| 2012/0207760 A1 | 8/2012 | Grandea, III et al. |
| 2012/0213771 A1 | 8/2012 | Keler et al. |
| 2012/0315277 A1 | 12/2012 | Grandea, III et al. |
| 2013/0045492 A1 | 2/2013 | Babb et al. |
| 2013/0158238 A1 | 6/2013 | Grandea, III et al. |
| 2013/0185821 A1 | 7/2013 | Babb et al. |
| 2013/0198879 A1 | 8/2013 | McWhirter et al. |
| 2013/0198880 A1 | 8/2013 | Babb et al. |
| 2013/0216555 A1 | 8/2013 | Nitsch et al. |
| 2013/0266514 A1 | 10/2013 | Nitsch et al. |
| 2013/0266585 A1 | 10/2013 | Nitsch et al. |
| 2013/0266586 A1 | 10/2013 | Nitsch et al. |
| 2013/0302836 A1 | 11/2013 | McWhirter et al. |
| 2013/0323248 A1 | 12/2013 | Gros et al. |
| 2013/0323249 A1 | 12/2013 | Zhou et al. |
| 2014/0017166 A1 | 1/2014 | Hettmann et al. |
| 2014/0046039 A1 | 2/2014 | Ahmed et al. |
| 2014/0056903 A1 | 2/2014 | Croll et al. |
| 2014/0088295 A1 | 3/2014 | Smith et al. |
| 2014/0227285 A1 | 8/2014 | Digiandomenico et al. |
| 2014/0363441 A1 | 12/2014 | Grandea, III et al. |
| 2015/0017096 A1 | 1/2015 | Wheeler et al. |
| 2015/0023966 A1 | 1/2015 | Digiandomenico et al. |
| 2015/0037339 A1 | 2/2015 | Gromada et al. |
| 2015/0059009 A1 | 2/2015 | McWhirter et al. |
| 2015/0098948 A1 | 4/2015 | Grandea, III et al. |
| 2015/0104459 A1 | 4/2015 | Grandea, III et al. |
| 2015/0110801 A1 | 4/2015 | Croll et al. |
| 2015/0133641 A1 | 5/2015 | Germaschewski et al. |
| 2015/0147343 A1 | 5/2015 | Nitsch et al. |
| 2015/0203579 A1 | 7/2015 | Papadopoulos et al. |
| 2015/0203580 A1 | 7/2015 | Papadopoulos et al. |
| 2015/0284450 A1 | 10/2015 | Digiandomenico et al. |
| 2015/0313193 A1 | 11/2015 | McWhirter et al. |
| 2015/0337029 A1 | 11/2015 | Kyratsous et al. |
| 2016/0083466 A1 | 3/2016 | Orengo et al. |
| 2016/0168264 A1 | 6/2016 | Rothe et al. |
| 2016/0176953 A1 | 6/2016 | Ngambo et al. |
| 2016/0215040 A1 | 7/2016 | Kyratsous et al. |
| 2016/0219847 A1 | 8/2016 | McWhirter et al. |
| 2016/0222126 A1 | 8/2016 | Hettmann et al. |
| 2016/0289310 A1 | 10/2016 | Nitsch et al. |
| 2016/0297872 A1 | 10/2016 | Digiandomenico et al. |
| 2016/0311909 A1 | 10/2016 | Sivakumar et al. |
| 2016/0376350 A1 | 12/2016 | Cha |
| 2017/0021031 A1 | 1/2017 | Hettmann et al. |
| 2017/0037124 A1 | 2/2017 | Gusarova et al. |
| 2017/0051074 A1 | 2/2017 | Kirshner et al. |
| 2017/0088620 A1 | 3/2017 | Nioi et al. |
| 2017/0096474 A1 | 4/2017 | Marks et al. |
| 2017/0096488 A1 | 4/2017 | Croll et al. |
| 2017/0101472 A1 | 4/2017 | Ullman et al. |
| 2017/0101477 A1 | 4/2017 | Gromada et al. |
| 2017/0182161 A1 | 6/2017 | Zhou et al. |
| 2017/0204200 A1 | 7/2017 | Bhatta et al. |
| 2017/0281765 A1 | 10/2017 | Zhou et al. |
| 2017/0283491 A1 | 10/2017 | Nitsch et al. |
| 2017/0320948 A1 | 11/2017 | Smith et al. |
| 2017/0332610 A1 | 11/2017 | Voronina et al. |
| 2017/0340728 A1 | 11/2017 | Kyratsous et al. |
| 2017/0355751 A1 | 12/2017 | Kyratsous et al. |
| 2017/0355757 A1 | 12/2017 | Hu et al. |
| 2017/0355774 A1 | 12/2017 | Delfino et al. |
| 2017/0362321 A1 | 12/2017 | Campbell et al. |
| 2017/0369593 A1 | 12/2017 | McWhirter et al. |
| 2018/0008672 A1 | 1/2018 | Chalothor et al. |
| 2018/0057583 A1 | 3/2018 | Orengo et al. |
| 2018/0066058 A1 | 3/2018 | Sainson et al. |
| 2018/0112001 A1 | 4/2018 | Haber et al. |
| 2018/0118836 A1 | 5/2018 | Bernett et al. |
| 2018/0118848 A1 | 5/2018 | Haber et al. |
| 2018/0127501 A1 | 5/2018 | Bemnett et al. |
| 2018/0127508 A1 | 5/2018 | Gromada et al. |
| 2018/0134781 A1 | 5/2018 | Gusarova et al. |
| 2018/0134794 A1 | 5/2018 | Babb et al. |
| 2018/0134805 A1 | 5/2018 | Hettmann et al. |
| 2018/0148503 A1 | 5/2018 | Scheinberg et al. |
| 2018/0155416 A1 | 6/2018 | Gromada et al. |
| 2018/0161464 A1 | 6/2018 | Kelly et al. |
| 2018/0185668 A1 | 7/2018 | Papadopoulos et al. |
| 2018/0186883 A1 | 7/2018 | Papadopoulos et al. |
| 2018/0214569 A1 | 8/2018 | Coppi et al. |
| 2018/0215823 A1 | 8/2018 | Smith et al. |
| 2018/0228926 A1 | 8/2018 | Kelly et al. |
| 2018/0244804 A1 | 8/2018 | MacDonald et al. |

FOREIGN PATENT DOCUMENTS

| | | |
|---|---|---|
| EP | 1223981 B1 | 1/2008 |
| JP | 2007535472 A | 12/2007 |
| JP | 2008500830 A | 1/2008 |
| KR | 100575069 B1 | 5/2006 |
| KR | 100618081 B1 | 8/2006 |
| KR | 100634847 B1 | 10/2006 |
| KR | 1020070041781 A | 4/2007 |
| KR | 1020070073886 A | 7/2007 |
| KR | 1020110008086 A | 1/2011 |
| KR | 1020120133403 A | 12/2012 |
| KR | 1020190080992 A | 7/2019 |
| WO | 9309812 A1 | 5/1993 |
| WO | 9736932 A1 | 10/1997 |
| WO | 0215445 A2 | 2/2002 |
| WO | 2005003170 A2 | 1/2005 |
| WO | 2005003360 A1 | 1/2005 |
| WO | 2005118642 A2 | 12/2005 |

(56) References Cited

FOREIGN PATENT DOCUMENTS

| | | |
|---|---|---|
| WO | 2008112003 A2 | 9/2008 |
| WO | 2008127655 A1 | 10/2008 |
| WO | 2008151319 A2 | 12/2008 |
| WO | 2009002380 A2 | 12/2008 |
| WO | 2009026558 A1 | 2/2009 |
| WO | 2009082624 A2 | 7/2009 |
| WO | 2009120922 A2 | 10/2009 |
| WO | 2010032059 A2 | 3/2010 |
| WO | 2010035012 A1 | 4/2010 |
| WO | 2010063818 A2 | 6/2010 |
| WO | 2011015649 A1 | 2/2011 |
| WO | 2011060206 A2 | 5/2011 |
| WO | 2011097603 A1 | 8/2011 |
| WO | 2012018404 A2 | 2/2012 |
| WO | 2012112489 A2 | 8/2012 |
| WO | 2012125614 A1 | 9/2012 |
| WO | 2012145673 A1 | 10/2012 |
| WO | 2012148873 A2 | 11/2012 |
| WO | 2012154999 A1 | 11/2012 |
| WO | 2012158818 A2 | 11/2012 |
| WO | 2013022782 A1 | 2/2013 |
| WO | 2013056068 A1 | 4/2013 |
| WO | 2013124419 A1 | 8/2013 |
| WO | 2013134263 A1 | 9/2013 |
| WO | 2013166448 A1 | 11/2013 |
| WO | 2013184761 A1 | 12/2013 |
| WO | 2014031712 A1 | 2/2014 |
| WO | 2014047231 A1 | 3/2014 |
| WO | 2014062245 A2 | 4/2014 |
| WO | 2014144080 A2 | 9/2014 |
| WO | 2014160179 A1 | 10/2014 |
| WO | 2014160202 A1 | 10/2014 |
| WO | 2014209384 A1 | 12/2014 |
| WO | 2015017576 A1 | 2/2015 |
| WO | 2015030539 A1 | 3/2015 |
| WO | 2015112800 A1 | 7/2015 |
| WO | 2015112805 A1 | 7/2015 |
| WO | 2015155998 A1 | 10/2015 |
| WO | 2015179535 A1 | 11/2015 |
| WO | 2016049000 A2 | 3/2016 |
| WO | 2016100807 A2 | 6/2016 |
| WO | 2016123019 A1 | 8/2016 |
| WO | 2016149678 A1 | 9/2016 |
| WO | 2016164468 A2 | 10/2016 |
| WO | 2016191246 A2 | 12/2016 |
| WO | 2017008153 A1 | 1/2017 |
| WO | 2017023761 A1 | 2/2017 |
| WO | 2017027316 A1 | 2/2017 |
| WO | 2017053856 A1 | 3/2017 |
| WO | 2017062888 A1 | 4/2017 |
| WO | 2017066204 A1 | 4/2017 |
| WO | 2017102830 A1 | 6/2017 |
| WO | 2017106383 A1 | 6/2017 |
| WO | 2017189959 A1 | 11/2017 |
| WO | 2017189963 A1 | 11/2017 |
| WO | 2017201476 A1 | 11/2017 |
| WO | 2017214548 A1 | 12/2017 |
| WO | 2017218515 A1 | 12/2017 |
| WO | 2017218707 A2 | 12/2017 |
| WO | 2018009732 A1 | 1/2018 |
| WO | 2018016881 A1 | 1/2018 |
| WO | 2018045110 A1 | 3/2018 |
| WO | 2018058001 A1 | 3/2018 |
| WO | 2018058003 A1 | 3/2018 |
| WO | 2018067331 A1 | 4/2018 |
| WO | 2018075621 A1 | 4/2018 |
| WO | 2018089532 A1 | 5/2018 |
| WO | 2018093866 A1 | 5/2018 |
| WO | 2018094112 A1 | 5/2018 |
| WO | 2018102682 A1 | 6/2018 |
| WO | 2018115859 A1 | 6/2018 |
| WO | 2018128973 A1 | 7/2018 |
| WO | 2018148476 A1 | 8/2018 |
| WO | 2018217918 A2 | 11/2018 |
| WO | 2019201866 A1 | 10/2019 |
| WO | 2021006604 A1 | 1/2021 |

OTHER PUBLICATIONS

Chen, X. et al., "Fusion protein linkers: Property, design and functionality," Advanced Drug Delivery Reviews, 65:1357-1369 (2013), Elsevier B.V.

Chi, S. et al., "MR1 SAFA, a Mouse Version of APB A1, Exhibits Therapeutic Efficacy in Collagen induced Arthritis Mouse Model by Blocking the CD40 CD40L Interaction," PEGS Boston, May 11-13, 2021, AprilBio Co., LTD.

Cho, S. et al., "Structural basis of serum albumin recognition by SL335, an antibody Fab extending the serum half-life of protein therapeutics," Biochemical and Biophysical Research Communications, 526: 941-946 (2020), Elsevier Inc., available online Apr. 2020.

Clackson, T. et al., "Making antibody fragments using phage display libraries," Letters to Nature, 352: 624-628 (1991).

Cristina, P. et al., "Systematic comparison of single-chain Fv antibody-fusion toxin constructs containing Pseudomonas Exotoxin A or saporin produced in different microbial expression systems," Microbial Cell Factories, 14:19 (2015), BioMed Central.

Griffin, L. et al., "Analysis of heavy and light chain sequences of conventional camelid antibodies from *Camelus dromedarius* and *Camelus bactrianus* species," Journal of Immunological Methods, 405:35-46 (2014), Elsevier B.V.

Holt, L. et al., "Anti-Serum Albumin Domain Antibodies for Extending the Half-Lives of Short Lived Drugs," Protein Engineering, Design and Selection, 21(5):283-288 (2008), Oxford University Press.

Hust, M. et al., "Single chain Fab (scFab) fragment," BMC Biotechnology, 7(14):1-15 (2007), BioMed Central.

International Search Report dated Dec. 2, 2014 in Intl. Pat. Appl. No. PCT/KR2014/008106.

Jazayeri, J. et al., "Half-Life Extension by Fusion to the Fc Region," Therapeutic Proteins, 157-188 (2012), Wiley-VCH Verlag GmbH & Co. KGaA.

Ji, S. et al., "Intact bioactivities and improved pharmacokinetic of the SL335-IFN-β-1a fusion protein that created by genetic fusion of SL335, a human anti-serum albumin fab, and human interferon-β," Immunology Letters, 207:46-55 (Mar. 2019), Elsevier B.V.

Kang, H. et al., "Isolation of human anti-serum albumin Fab antibodies with an extended serum-half life," Immunology Letters, 169:33-40 (2016), Elsevier B.V, available online Nov. 2015.

Kang, H. et al., "Optimal expression of a Fab-effector fusion protein in *Escherichia coli* by removing the cysteine residues responsible for an interchain disulfide bond of a Fab molecule," Immunology Letters, 184:34-42 (2017), Elsevier B.V.

Karpusas, M. et al., "Structure of CD40 Ligand in Complex with the Fab Fragment of a Neutralizing Humanized Antibody," Structure, 9:321-329 (2001), Elsevier Science Ltd.

Kenyon, N. et al., "Long-term survival and function of intrahepatic islet allografts in rhesus monkeys treated with humanized anti-CD154," Medical Sciences, 96:8132-8137 (1999), Proceedings of the National Academy of Sciences, USA.

Kim, S. et al., "Guided Selection of Human Antibody Light Chains against TAG-72 Using a Phage Display Chain Shuffling Approach," The Journal of Microbiology, 45(6):572-577 (2007), The Microbiological Society of Korea.

Lu, D. et al., "Fab-scFv fusion protein: an efficient approach to production of bispecific antibody fragments," J. Immunol. Methods, 267:213-226 (2002), Elsevier Science B.V.

Notification of Transmittal of the International Search Report and the Written Opinion of the International Searching Authority, or the Declaration dated Apr. 23, 2021 in Intl. Pat. Appl. No. PCT/IB2021/050519.

Office Action dated Mar. 21, 2017 in JP Appl. No. 2016-0538860 with English translation.

(56) References Cited

OTHER PUBLICATIONS

Osborn, B. et al., "Albutropin: a growth hormone albumin fusion with improved pharmacokinetics and pharmacodynamics in rats and monkeys," European Journal of Pharmacology, 456:149-158 (2002), Elsevier Science B.V.

Rader, C. et al., "A phage display approach for rapid antibody humanization: Designed combinatorial V gene libraries," Medical Science, 95:8910-8915 (1998), The National Academy of Sciences.

Search Report dated Feb. 27, 2017 in EP Pat. Appl. No. 14839630.2.

Sexton, L. et al., "Resistive-Pulse Studies of Proteins and Protein/Antibody Complexes Using a Conical Nanotube Sensor," 129:13144-13152 (2007), Journal of the American Chemical Society.

Shock, A. et al., "CDP7657, an anti-CD40L antibody lacking an Fc domain, inhibits CD40L-dependent immune responses without thrombotic complications: an in vivo study," Arthritis Research & Therapy, 17:234 (2015), BioMed Central.

Smith, B. et al., "Prolonged in Vivo Residence Times of Antibody Fragments Associated with Albumin," Bioconjugate Chem., 12:750-756 (2001), American Chemical Society.

Sogaard, M. et al., "Treatment with Tumor-Reactive Fab-IL-2 and Fab-Staphylococcal Enterotoxin A Fusion Proteins Leads to Sustained T Cell Activation, and Long-Term Survival of Mice with Established Tumors," International Journal of Oncology, 15:873-882 (1999), Active Biotech Research AB, Lund, SE.

Tocoian, A. et al., "First-in-human trial of the safety, pharmacokinetics and immunogenicity of a PEGylated anti-CD40L antibodyfragment (CDP7657) in healthy individuals and patients with systemic lupus erythematosus," Lupus 24:1045-1056 (2015), UCB Pharma Ltd.

Written Opinion dated Dec. 2, 2014 in Intl. Pat. Appl. No. PCT/KR2014/008106, WIPO.

Xie, J. et al., "Engineering of a Novel Anti-CD40L Domain Antibody for Treatment of Autoimmune Diseases," J. of Immunol., 192(9):4083-4092 (2014), The American Association of Immunologists, Inc.

FIG. 1B

APB-A1 H amino acid sequence

```
         10         20         30         40         50         60         70         80
DIVLTQSPAT LSVSPGERAT ISCRASQRVS SSTYSYMHWY QQKPGQPPKL LIKYASNLES GVPARFSGSG SGTDFTLTIS
         90        100        110        120        130        140        150        160
SVEPEDFATY YCQHSWEIPP TFGGGTKLEI KRGGGGSGGG GSGGGGSQVQ LVQSGAEVVK PGASVKLSCK ASGYIFTSYY
        170        180        190        200        210        220        230        240
MYWVKQAPGQ GLEWIGEINP SNGDTNFNEK FKSKATLTVD KSASTAYMEL SSLRSEDTAV YYCTRSDGRN DMDSWGQGTL
        250        260        270        280        290        300        310        320
VTVSSGGGGS GGGGSGGGGS QVQLVQSGGG PVKPGGSLRL SCAASGFMFR AYSMNWVRQA PGKGLEWVSS ISSSGRYIHY
        330        340        350        360        370        380        390        400
ADSVKGRFTI SRDNAKNSLY LQMNSLRAED TAVYYCARET VMAGKALDYW GQGTLVTVSS ASTKGPSVFP LAPSSKSTSE
        410        420        430        440        450        460        470        480
GTAALGCLVK DYFPEPVTVS WNSGALTSGV HTFPAVLQSS GLYSLSSVVT VPSSSLGTQT YICNVNHKPS NTKVDKKVEP
KSS
```

APB-A1 L amino acid sequence

```
         10         20         30         40         50         60         70         80
DIVLTQSPAT LSVSPGERAT ISCRASQRVS SSTYSYMHWY QQKPGQPPKL LIKYASNLES GVPARFSGSG SGTDFTLTIS
         90        100        110        120        130        140        150        160
SVEPEDFATY YCQHSWEIPP TFGGGTKLEI KRGGGGSGGG GSGGGGSQVQ LVQSGAEVVK PGASVKLSCK ASGYIFTSYY
        170        180        190        200        210        220        230        240
MYWVKQAPGQ GLEWIGEINP SNGDTNFNEK FKSKATLTVD KSASTAYMEL SSLRSEDTAV YYCTRSDGRN DMDSWGQGTL
        250        260        270        280        290        300        310        320
VTVSSGSISG SGKPGSGEGS TKGDIVLTQS PGTLSLSPGE TATLSCRASQ SVGSNLAWYQ QKPGQAPRLL IYGASTGATG
        330        340        350        360        370        380        390        400
VPARFSGSRS GTDFTLTITS LQPEDFATYY CQQYYSFLAK TFGQGTQLEI KRTVAAPSVF IFPPSDEQLK SGTASVVCLL
        410        420        430        440        450        460        470
NNFYPREAKV QWKVDNALQS GNSQESVTEQ DSKDSTYSLS NTLTLSKADY EKHKVYACEV THQGLSSPVT KSFNRGES
```

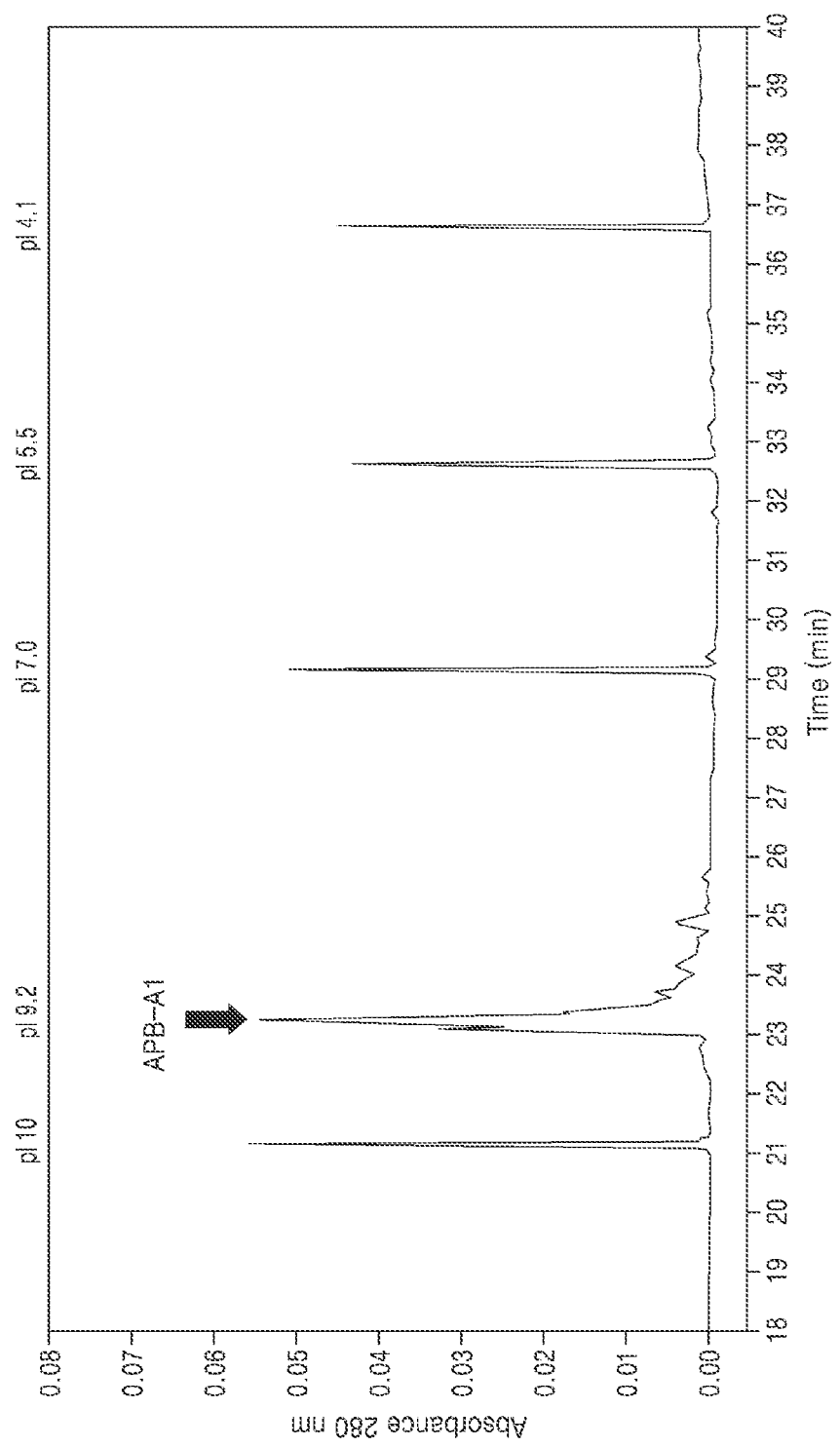

APB-B1a

FIG. 14

APB-B1 heavy chain

```
         10         20         30         40         50         60         70         80
DIVLTQSPAT LSVSPGERAT ISCRASQRVS SSTYSYMHWY QQKPGQPPKL LIKYASNLES GVPARFSGSG SGTDFTLTIS 90        100        110        120        130        140        150        160
SVEPEDFATY YCQHSWEIPP TFGQGTKLEI KRGGGGSGGG GSGGGGSQVQ LVQSGAEVVK PGASVKLSCK ASGYIFTSYY 170        180        190        200        210        220        230        240
MYWVKQAPGQ GLEWIGEINP SNGDTNFNEK FKSKATLTVD KSASTAYMEL SSLRSEDTAV YYCTRSDGRN DMDSWGQGTL 250        260        270        280        290        300        310        320
VTVSSGGGGS GGGGSGGGGS QVQLVQSGGG PVKPGGSLRL SCAASGFMFR AYSMNWVRQA PGKGLEWVSS ISSSGRYIHY 330        340        350        360        370        380        390        400
ADSVKGRFTI SRDNAKNSLY LQMNSLRAED TAVYYCARET VMAGKALDYW GQGTLVTVSS ASTKGPSVFP LAPSSKSTSE 410        420        430        440        450        460        470        480
GTAALGCLVK DYFPEPVTVS WNSGALTSGV HTFPAVLQSS GLYSLSSVVT VPSSSLGTQT YICNVNHKPS NTKVDKKVEP 490        500        510        520        530        540        550        560
KSSGGGGSGG GGSGGGGSEV QLVESGGGLV QPGGSLRLSC AASGYVFTDY GMNWVRQAPG KGLEWMGWIN TYTGEPIYAD 570        580        590        600        610
SVKGRFTFSL DTSKSTAYLQ MNSLRAEDTA VYYCARGYRS YAMDYWGQGT LVTVSS
```

APB-B1 Light chain

```
         10         20         30         40         50         60         70         80
DIVLTQSPAT LSVSPGERAT ISCRASQRVS SSTYSYMHWY QQKPGQPPKL LIKYASNLES GVPARFSGSG SGTDFTLTIS 90        100        110        120        130        140        150        160
SVEPEDFATY YCQHSWEIPP TFGQGTKLEI KRGGGGSGGG GSGGGGSQVQ LVQSGAEVVK PGASVKLSCK ASGYIFTSYY 170        180        190        200        210        220        230        240
MYWVKQAPGQ GLEWIGEINP SNGDTNFNEK FKSKATLTVD KSASTAYMEL SSLRSEDTAV YYCTRSDGRN DMDSWGQGTL 250        260        270        280        290        300        310        320
VTVSSGSTSG SGKPGSGEGS TKGDIVLTQS PGTLSLSPGE TATLSCRASQ SVGSNLAWYQ QKPGQAPRLL IYGASTGATG 330        340        350        360        370        380        390        400
VPARFSGSRS GTDFTLTITS LQPEDFATYY CQQYYSFLAK TFGQGTQLEI KRTVAAPSVF IFPPSDEQLK SGTASVVCLL 410        420        430        440        450        460        470        480
NNFYPREAKV QWKVDNALQS GNSQESVTEQ DSKDSTYSLS NTLTLSKADY EKHKVYACEV THQGLSSPVT KSFNRGESGG 490        500        510        520        530        540        550        560
GGSGGGGSGG GGSDIQMTQS PSSLSASVGD RVTITCKASQ NVGTNVAWYQ QKPGKAPKAL IYSASFLYSG VPYRFSGSGS 570        580        590        600
GTDFTLTISS LQPEDFATYY CQQYNIYPLT FGQGTKVEIK R
```

MULTISPECIFIC ANTIBODIES, COMPOSITIONS COMPRISING THE SAME, AND VECTORS AND USES THEREOF

CROSS-REFERENCE TO RELATED APPLICATIONS

This application is a continuation of U.S. application Ser. No. 17/759,313, which is a § 371 national phase of PCT/IB2021/050519, having an international filing date of Jan. 23, 2021, which claims priority to Korean Appl. No. 10-2020-0009565, filed Jan. 24, 2020, and U.S. application Ser. No. 16/878,255, filed May 19, 2020, the disclosure of each incorporated herein in its entirety by reference.

SEQUENCE LISTING

This application contains a sequence listing which has been submitted electronically in XML format and is hereby incorporated by reference in its entirety. Said XML copy, created on Jan. 3, 2023, is named 2662-0001US03 SEQL.xml and is 150 KB in size.

FIELD

The present disclosure relates to fusion constructs comprising an antigen binding fragment and bioactive effector moieties. More particularly, the present disclosure relates to multispecific antibodies comprising two or more bioactive effector moieties linked to either or both of an N-terminal and a C-terminal of an antigen binding fragment that binds to human serum albumin.

BACKGROUND

A CD40-CD40L interaction essentially acts on the creation of antigen-specific antibody immune responses, and autoantibodies involve pathogenesis of various autoimmune diseases. For effectively treating these diseases, a variety of CD40L- or CD40-specific antibodies capable of inhibiting and/or suppressing the CD40-CD40L interaction have been researched. For example, anti-CD40L monoclonal antibodies, hu5c8 IgG1 (BG-9588, ruplizumab, Antova™, Biogen, Cambridge, Massachusetts), and IDEC-131 (E6040, IDEC Pharmaceuticals, San Diego, California) have been studied for treatment of various autoimmune diseases, including, for example, systemic lupus erythematosus (SLE) and idiopathic thrombocytopenic purpura (ITP), but additional development of such antibodies has been halted due to incidence of side effects such as thromboembolism. Hence, approaches for addressing issues of the thromboembolic side effect have been attempted by many research groups through Fc engineering, and there have been several reports including for example, a PEGylated anti-CD40L Fab, CDP7657 (Dapirolizumab pegol, Biogen), and a TN3-HSA fusion protein designed to be linked to CD40L, VIB4920 (VIELABIO, Gaithersburg, MD). In this connection, as a therapeutic agent targeting CD40, not CD40L, a BI655064 antibody having a weakened Fc function (Boehringer Ingelheim, Germany), a bleselumab antibody of a human IgG4 type (Kyowa Kirin Pharmaceutical Development, La Jolla, California), and so on, are being developed by other research groups.

SUMMARY

The present disclosure provides multispecific antibodies having an extended in vivo retention time. The present disclosure also provides pharmaceutical compositions comprising the multispecific antibody. The present disclosure also provides methods of producing the multispecific antibody.

For example, disclosed herein are novel autoimmune disease therapeutic agents for suppressing a CD40-CD40L signal while eliminating the Fc-based thromboembolic side effect of an anti-CD40L antibody. To this end, a recombinant bispecific antibody has been developed, represented by (anti-CD40L scFv)$_2$-(anti-HSA Fab)-(anti-TNF-α Fv) capable of maintaining serum sustainability without a Fc region by linking a single-chain variable fragment (scFv) consisting of variable region genes $V_H$ and $V_L$ of hu5c8, a ruplizumab antibody binding to CD40L, to the N-terminal of SL335 Fab. In addition, disclosed herein are multispecific antibodies represented by (anti-CD40L scFv)$_2$-(anti-HSA Fab)-(anti-TNF-α Fv) by linking Fv or dsFv containing of a variable region gene of a certolizumab pegol antibody binding to TNF-α to the C-terminal of SL335 Fab of the bispecific antibody using a peptide linker, and identified functions and characteristics of the produced antibody protein.

Disclosed herein are multispecific antibodies comprising a structural formula of:

wherein the antigen binding fragment (Fab) is a serum albumin Fab;

wherein $R^1$ and $R^2$ are bioactive effector moieties linked to an N-terminus of the Fab, each linked to a heavy chain variable domain or a light chain variable domain of the Fab;

wherein $R^3$ and $R^4$ are bioactive effector moieties linked to a C-terminus of the Fab, each linked to a heavy chain variable domain or a light chain variable domain of the Fab;

wherein m is 0 or an integer of 1 or greater; and wherein n is 0 or an integer of 1 or greater. In some embodiments, $R^1$ and $R^2$ are same or different single-chain variable fragments (scFv). In some embodiments, $R^3$ and $R^4$ are same or different Fv fragments or disulfide-stabilized Fv (dsFv) fragments.

In some embodiments, each of $R^1$, $R^2$, $R^3$, and $R^4$ can be linked to the Fab by one or more linkers. Each linker can comprise 1 to 20 amino acids. Each linker can comprise an amino acid sequence having at least 90% identity to SEQ ID NO:3 or SEQ ID NO:4. Each linker can comprise an amino acid sequence of SEQ ID NO:3 or SEQ ID NO:4.

In some embodiments, the Fab comprises a heavy chain variable domain comprising
  (a) a heavy chain complementarity determining domain 1 (CDR1) comprising the amino acid sequence of SYGIS (SEQ ID NO:61), a heavy chain CDR2 comprising the amino acid sequence of WINTYSGGTKYAQKFQG (SEQ ID NO:62), and a heavy chain CDR3 comprising the amino acid sequence of LGHCQRGICSDALDT (SEQ ID NO:63);
  (b) a heavy chain complementarity determining domain 1 (CDR1) comprising the amino acid sequence of SYGIS (SEQ ID NO:61), a heavy chain CDR2 comprising the amino acid sequence of RINTYNGNTGYAQRLQG (SEQ ID NO:64), and a heavy chain CDR3 comprising the amino acid sequence of LGHCQRGICSDALDT (SEQ ID NO:63);

(c) a heavy chain complementarity determining domain 1 (CDR1) comprising the amino acid sequence of NYGIH (SEQ ID NO:65), a heavy chain CDR2 comprising the amino acid sequence of SISYDGSNKYY-ADSVKG (SEQ ID NO:66), and a heavy chain CDR3 comprising the amino acid sequence of DVHYYGSGSYYNAFDI (SEQ ID NO:67);

(d) a heavy chain complementarity determining domain 1 (CDR1) comprising the amino acid sequence of SYAMS (SEQ ID NO:68), a heavy chain CDR2 comprising the amino acid sequence of VISHDGGFQYY-ADSVKG (SEQ ID NO:69), and a heavy chain CDR3 comprising the amino acid sequence of AGWLRQYGMDV (SEQ ID NO:70);

(e) a heavy chain complementarity determining domain 1 (CDR1) comprising the amino acid sequence of AYWIA (SEQ ID NO:71), a heavy chain CDR2 comprising the amino acid sequence of MIWPPDADA-RYSPSFQG (SEQ ID NO:72), and a heavy chain CDR3 comprising the amino acid sequence of LYSG-SYSP (SEQ ID NO:73); or (f) a heavy chain complementarity determining domain 1 (CDR1) comprising the amino acid sequence of AYSMN (SEQ ID NO:74), a heavy chain CDR2 comprising the amino acid sequence of SISSSGRYIHY-ADSVKG (SEQ ID NO:75), and a heavy chain CDR3 comprising the amino acid sequence of ETVMAGKA-LDY (SEQ ID NO:76).

In some embodiments, the Fab comprises a light chain variable domain comprising (g) a light chain complementarity determining domain 1 (CDR1) comprising the amino acid sequence of RASQ-SISRYLN (SEQ ID NO:77), a light chain CDR2 comprising the amino acid sequence of GASRLES (SEQ ID NO:78), and a light chain CDR3 comprising the amino acid sequence of QQSDSVPVT (SEQ ID NO:79);

(h) a light chain complementarity determining domain 1 (CDR1) comprising the amino acid sequence of RASQ-SISSYLN (SEQ ID NO:80), a light chain CDR2 comprising the amino acid sequence of AASSLQS (SEQ ID NO:81), and a light chain CDR3 comprising the amino acid sequence of QQSYSTPPYT (SEQ ID NO:82);

(i) a light chain complementarity determining domain 1 (CDR1) comprising the amino acid sequence of RASQSIFNYVA (SEQ ID NO:83), a light chain CDR2 comprising the amino acid sequence of DASNRAT (SEQ ID NO:84), and a light chain CDR3 comprising the amino acid sequence of QQRSKWPPTWT (SEQ ID NO:85);

(j) a light chain complementarity determining domain 1 (CDR1) comprising the amino acid sequence of RASETVSSRQLA (SEQ ID NO:86), a light chain CDR2 comprising the amino acid sequence of GASSRAT (SEQ ID NO:87), and a light chain CDR3 comprising the amino acid sequence of QQYGSSPRT (SEQ ID NO:88);

(k) a light chain complementarity determining domain 1 (CDR1) comprising the amino acid sequence of RASQSVSSSSLA (SEQ ID NO:89), a light chain CDR2 comprising the amino acid sequence of GASSRAT (SEQ ID NO:87), and a light chain CDR3 comprising the amino acid sequence of QKYSSYPLT (SEQ ID NO:90); or (l) a light chain complementarity determining domain 1 (CDR1) comprising the amino acid sequence of RASQSVGSNLA (SEQ ID NO:91), a light chain CDR2 comprising the amino acid sequence of GAST-GAT (SEQ ID NO:92), and a light chain CDR3 comprising the amino acid sequence of QQYYSFLAKT (SEQ ID NO:93).

In some embodiments, the Fab comprises a heavy chain complementarity determining domain 1 (CDR1) comprising the amino acid sequence of AYSMN (SEQ ID NO:74), a heavy chain CDR2 comprising the amino acid sequence of SISSSGRYIHYADSVKG (SEQ ID NO:75), and a heavy chain CDR3 comprising the amino acid sequence of ETVMAGKALDY (SEQ ID NO:76), and a light chain complementarity determining domain 1 (CDR1) comprising the amino acid sequence of RASQSVG-SNLA (SEQ ID NO:91), a light chain CDR2 comprising the amino acid sequence of GASTGAT (SEQ ID NO:92), and a light chain CDR3 comprising the amino acid sequence of QQYYSFLAKT (SEQ ID NO:93).

In some embodiments, the Fab comprises a heavy chain variable domain comprising an amino acid sequence having at least 80% identity to SEQ ID NO:94, 95, 96, 97, 98, or 99.

In some embodiments, the Fab comprises a light chain variable domain comprising an amino acid sequence having at least 80% identity to SEQ ID NO:100, 101, 102, 103, 104, or 105.

In some embodiments, the Fab comprises a heavy chain variable domain comprising an amino acid sequence having at least 80% identity to SEQ ID NO:94, 95, 96, 97, 98, or 99, and a light chain variable domain comprising an amino acid sequence having at least 80% identity to SEQ ID NO:100, 101, 102, 103, 104, or 105, respectively.

In some embodiments, the Fab comprises a heavy chain domain comprising an amino acid sequence of SEQ ID NO:45 ($V_H$-$C_{H1}$ domain) and a light chain domain comprising an amino acid sequence of SEQ ID NO:46 ($V_L$-$C_L$ domain).

In some embodiments, each of the $R^1$ and $R^2$ is an anti-CD40L hu5c8 scFv. Each of the $R^1$ and $R^2$ can be an anti-CD40L hu5c8 scFv comprising an amino acid sequence having at least 80% identity to SEQ ID NO:47 or SEQ ID NO:48. Each of the $R^1$ and $R^2$ can be an anti-CD40L hu5c8 scFv comprising an amino acid sequence of SEQ ID NO:47 or SEQ ID NO:48.

In some embodiments, each of $R^3$ and $R^4$ is one or more bioactive effector moieties comprising anti-TNF-α Fv, anti-TNF-α disulfide-stabilized Fv (dsFv), anti-IL-23 Fv, anti-IL-23 dsFv, anti-IFNAR1, and/or anti-IFNAR1 dsFv. Each of $R^3$ and $R^4$ can be one or more bioactive effector moieties comprising an anti-TNF-α Fv comprising a heavy chain amino acid sequence having 80% identity to SEQ ID NO:49 and a light chain amino acid sequence having 80% identity to SEQ ID NO:50, anti-TNF-α disulfide-stabilized Fv (dsFv) comprising a heavy chain amino acid sequence having 80% identity to SEQ ID NO:51 and a light chain amino acid sequence having 80% identity to SEQ ID NO:52, anti-IL-23 Fv comprising a heavy chain amino acid sequence having 80% identity to SEQ ID NO:53 and a light chain amino acid sequence having 80% identity to SEQ ID NO:54, anti-IL-23 dsFv comprising a heavy chain amino acid sequence having 80% identity to SEQ ID NO:55 and a light chain amino acid sequence having 80% identity to SEQ ID NO:56, anti-IFNAR1 comprising a heavy chain amino acid sequence having 80% identity to SEQ ID NO:57 and a light chain amino acid sequence having 80% identity to SEQ ID NO:58, and/or anti-IFNAR1 dsFv comprising a heavy chain amino acid sequence having 80% identity to SEQ ID NO:59 and a light chain amino acid sequence having 80% identity to SEQ ID NO:60. Each of $R^3$ and $R^4$ can be one or more bioactive effector moieties comprising an anti-TNF-α

Fv comprising a heavy chain of SEQ ID NO:49 and a light chain of SEQ ID NO:50, anti-TNF-α disulfide-stabilized Fv (dsFv) comprising a heavy chain of SEQ ID NO:51 and a light chain of SEQ ID NO:52, anti-IL-23 Fv comprising a heavy chain of SEQ ID NO:53 and a light chain of SEQ ID NO:54, anti-IL-23 dsFv comprising a heavy chain of SEQ ID NO:55 and a light chain of SEQ ID NO:56, anti-IFNAR1 comprising a heavy chain of SEQ ID NO:57 and a light chain of SEQ ID NO:58, and/or anti-IFNAR1 dsFv comprising a heavy chain of SEQ ID NO:59 and a light chain of SEQ ID NO:60.

Disclosed herein are compositions comprising multispecific antibodies disclosed herein and an excipient. Also disclosed herein are pharmaceutical compositions comprising multispecific antibodies disclosed herein and a pharmaceutically accepted excipient.

Also disclosed here are methods of treating an autoimmune disease in a subject in need thereof, the methods comprising administering a pharmaceutical composition disclosed herein to the subject.

Further disclosed herein are expression vectors comprising:
(a) a promoter,
(b) a first nucleic acid molecule encoding an antigen binding fragment (Fab) that binds to serum albumin, and
(c) a second nucleic acid molecule encoding a bioactive effector moiety and a linker, wherein the promoter, the first nucleic acid sequence, and the second nucleic acid molecules are operably linked. The second nucleic acid molecule can encode 2 or more bioactive effector moieties and linkers.

In some embodiments, the first nucleic acid molecule comprises a nucleic acid sequence encoding a Fab comprising a heavy chain variable domain comprising
(a) a heavy chain complementarity determining domain 1 (CDR1) comprising the amino acid sequence of SYGIS (SEQ ID NO:61),
   a heavy chain CDR2 comprising the amino acid sequence of WINTYSGGTKYAQKFQG (SEQ ID NO:62), and
   a heavy chain CDR3 comprising the amino acid sequence of LGHCQRGICSDALDT (SEQ ID NO:63);
(b) a heavy chain complementarity determining domain 1 (CDR1) comprising the amino acid sequence of SYGIS (SEQ ID NO:61),
   a heavy chain CDR2 comprising the amino acid sequence of RINTYNGNTGYAQRLQG (SEQ ID NO:64), and
   a heavy chain CDR3 comprising the amino acid sequence of LGHCQRGICSDALDT (SEQ ID NO:63);
(c) a heavy chain complementarity determining domain 1 (CDR1) comprising the amino acid sequence of NYGIH (SEQ ID NO:65),
   a heavy chain CDR2 comprising the amino acid sequence of SISYDGSNKYYADSVKG (SEQ ID NO:66), and
   a heavy chain CDR3 comprising the amino acid sequence of DVHYYGSGSYYNAFDI (SEQ ID NO:67);
(d) a heavy chain complementarity determining domain 1 (CDR1) comprising the amino acid sequence of SYAMS (SEQ ID NO:68),
   a heavy chain CDR2 comprising the amino acid sequence of VISHDGGFQYYADSVKG (SEQ ID NO:69), and
   a heavy chain CDR3 comprising the amino acid sequence of AGWLRQYGMDV (SEQ ID NO:70);
(e) a heavy chain complementarity determining domain 1 (CDR1) comprising the amino acid sequence of AYWIA (SEQ ID NO:71),
   a heavy chain CDR2 comprising the amino acid sequence of MIWPPDADARYSPSFQG (SEQ ID NO:72), and
   a heavy chain CDR3 comprising the amino acid sequence of LYSGSYSP (SEQ ID NO:73); or
(f) a heavy chain complementarity determining domain 1 (CDR1) comprising the amino acid sequence of AYSMN (SEQ ID NO:74),
   a heavy chain CDR2 comprising the amino acid sequence of SISSSGRYIHYADSVKG (SEQ ID NO:75), and
   a heavy chain CDR3 comprising the amino acid sequence of ETVMAGKALDY (SEQ ID NO:76).

In some embodiments, the first nucleic acid molecule comprises a nucleic acid sequence encoding a Fab comprising a light chain variable domain comprising
(g) a light chain complementarity determining domain 1 (CDR1) comprising the amino acid sequence of RASQSISRYLN (SEQ ID NO:77),
   a light chain CDR2 comprising the amino acid sequence of GASRLES (SEQ ID NO:78), and
   a light chain CDR3 comprising the amino acid sequence of QQSDSVPVT (SEQ ID NO:79);
(h) a light chain complementarity determining domain 1 (CDR1) comprising the amino acid sequence of RASQSISSYLN (SEQ ID NO:80),
   a light chain CDR2 comprising the amino acid sequence of AASSLQS (SEQ ID NO:81), and
   a light chain CDR3 comprising the amino acid sequence of QQSYSTPPYT (SEQ ID NO:82);
(i) a light chain complementarity determining domain 1 (CDR1) comprising the amino acid sequence of RASQSIFNYVA (SEQ ID NO:83),
   a light chain CDR2 comprising the amino acid sequence of DASNRAT (SEQ ID NO:84), and
   a light chain CDR3 comprising the amino acid sequence of QQRSKWPPTWT (SEQ ID NO:85);
(j) a light chain complementarity determining domain 1 (CDR1) comprising the amino acid sequence of RASETVSSRQLA (SEQ ID NO:86),
   a light chain CDR2 comprising the amino acid sequence of GASSRAT (SEQ ID NO:87), and
   a light chain CDR3 comprising the amino acid sequence of QQYGSSPRT (SEQ ID NO:88);
(k) a light chain complementarity determining domain 1 (CDR1) comprising the amino acid sequence of RASQSVSSSSLA (SEQ ID NO:89),
   a light chain CDR2 comprising the amino acid sequence of GASSRAT (SEQ ID NO:87), and
   a light chain CDR3 comprising the amino acid sequence of QKYSSYPLT (SEQ ID NO:90); or
(l) a light chain complementarity determining domain 1 (CDR1) comprising the amino acid sequence of RASQSVGSNLA (SEQ ID NO:91),
   a light chain CDR2 comprising the amino acid sequence of GASTGAT (SEQ ID NO:92), and
   a light chain CDR3 comprising the amino acid sequence of QQYYSFLAKT (SEQ ID NO:93).

In some embodiments, the first nucleic acid molecule comprises a nucleic acid sequence encoding a Fab comprising a heavy chain complementarity determining domain 1 (CDR1) comprising the amino acid sequence of AYSMN (SEQ ID NO:74), a heavy chain CDR2 comprising the amino acid sequence of SISSSGRYIHYADSVKG (SEQ ID NO:75), and a heavy chain CDR3 comprising the amino acid sequence of ETVMAGKALDY (SEQ ID NO:76), and a light chain complementarity determining domain 1 (CDR1) comprising the amino acid sequence of RASQSVG-SNLA (SEQ ID NO:91), a light chain CDR2 comprising the amino acid sequence of GASTGAT (SEQ ID NO:92), and a light chain CDR3 comprising the amino acid sequence of QQYYSFLAKT (SEQ ID NO:93).

In other embodiments, the first nucleic acid molecule comprises a nucleic acid sequence encoding a Fab comprising a heavy chain variable domain comprising an amino acid sequence having at least 80% identity to SEQ ID NO:94, 95, 96, 97, 98, or 99.

In some embodiments, the first nucleic acid molecule comprises a nucleic acid sequence encoding a Fab comprising a light chain variable domain comprising an amino acid sequence having at least 80% identity to SEQ ID NO:100, 101, 102, 103, 104, or 105.

In some embodiments, the first nucleic acid molecule comprises a nucleic acid sequence encoding a Fab comprising a heavy chain variable domain comprising an amino acid sequence having at least 80% identity to SEQ ID NO:94, 95, 96, 97, 98, or 99, and a light chain variable domain comprising an amino acid sequence having at least 80% identity to SEQ ID NO:100, 101, 102, 103, 104, or 105, respectively.

In some embodiments, the first nucleic acid molecule comprises a nucleic acid sequence encoding a Fab comprising a heavy chain domain comprising an amino acid sequence of SEQ ID NO:45 ($V_H$-$C_{H1}$ domain) and a light chain domain comprising an amino acid sequence of SEQ ID NO:46 ($V_L$-$C_L$ domain).

In some embodiments, the bioactive effector moieties are anti-TNF-α Fv, anti-TNF-α dsFv, anti-IL-23 Fv, anti-IL-23 dsFv, anti-IFNAR1 Fv, and/or anti-IFNAR1 dsFv. The second nucleic acid molecule can comprise a nucleotide sequence encoding the amino acid sequence of one or more of SEQ ID NOs: 49-60.

The present disclosure provides host cells comprising the expression vector, such as an animal cell, e.g., a CHO cell line.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 1A and 1B represent the vector maps and amino acid sequences of APB-A1: H amino acid sequence of SEQ ID NO:41 and L amino acid sequence of SEQ ID NO:42.

FIGS. 4A and 4B represent PI values of APB-A1.

FIG. 13A. (GGGGS)3 (SEQ ID NO:3) and GSTSGSGKPGSGEG-STKG (SEQ ID NO:4).

FIG. 14 represents amino acid sequences of APB-B1 heavy and light chains: SEQ ID NOS:106 and 107, respectively.

DETAILED DESCRIPTION

Figure 1A:
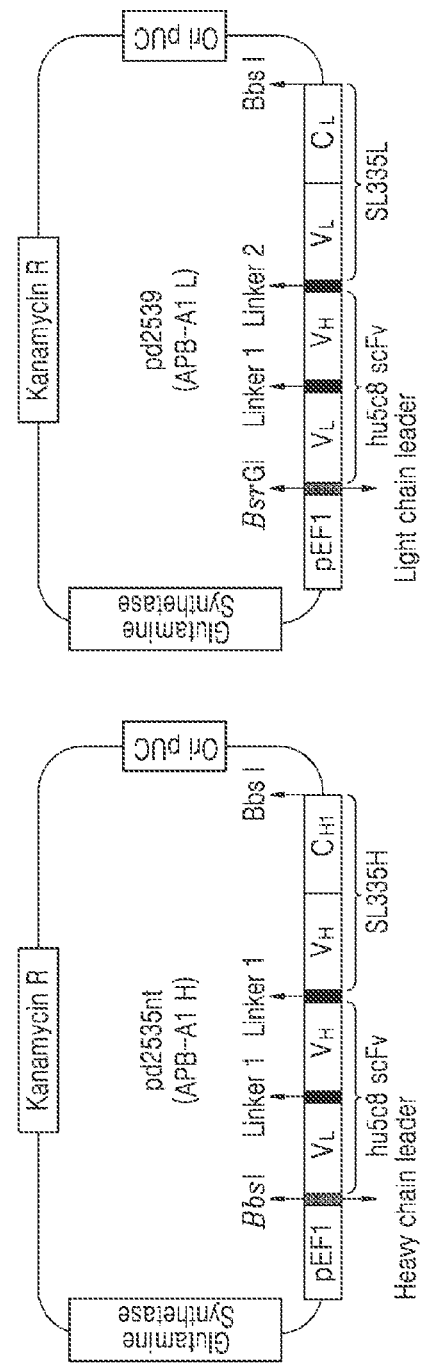

Reference will now be made in detail to embodiments, examples of which are illustrated in the accompanying drawings, wherein like reference numerals refer to like elements throughout. In this regard, the present embodiments can have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Provided herein are multispecific antibodies comprising a structural formula of:

wherein the antigen binding fragment (Fab) is a serum albumin Fab;

wherein $R^1$ and $R^2$ are bioactive effector moieties linked to an N-terminus of the Fab, each linked to a heavy chain variable domain or a light chain variable domain of the Fab;

wherein $R^3$ and $R^4$ are bioactive effector moieties linked to a C-terminus of the Fab, each linked to a heavy chain variable domain or a light chain variable domain of the Fab;

wherein m is 0 or an integer of 1 or greater; and wherein n is 0 or an integer of 1 or greater.

Also provided are isolated nucleic acids (polynucleotides), such as complementary DNA (cDNA), encoding such antibodies. Further provided are vectors (e.g., expression vectors) and cells (e.g., host cells) comprising nucleic acids (polynucleotides) encoding such antibodies. Also provided are methods of making such antibodies. In other aspects, provided herein are methods and uses for inducing, increasing or enhancing multispecific activities, and treating certain conditions, such as autoimmune diseases. Related compositions (e.g., pharmaceutical compositions), kits, and detection methods are also provided.

TERMINOLOGY

As used herein, the terms "about" and "approximately," when used to modify a numeric value or numeric range, indicate that deviations of 5% to 10% above and 5% to 10% below the value or range remain within the intended meaning of the recited value or range.

As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), bispecific antibodies, and multispecific antibodies.

As used herein, the terms "multispecific antibody" and "multispecific antibodies" are terms of art and can be used to refer to a molecule(s) with more than one bioactive effector moieties or antigen-binding sites, wherein each antigen-binding site specifically binds an antigen. The multispecific antibodies disclosed herein can have 2, 3, 4, 5, 6, 7, 8, or more bioactive effector moieties linked thereto.

Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$, $IgG_2$, or $IgG_4$) or subclass thereof. In some embodiments, the antibody is a humanized monoclonal antibody. In other embodiments, the antibody is a human monoclonal antibody, e.g., that is an immunoglobulin.

As used herein, the terms "bioeffector moiety," "antigen-binding domain," "antigen-binding region," "antigen-binding site," and similar terms refer to the portions of the multispecific antibody molecules that comprises the amino acid residues that confer on the antibody molecule its specificity for the antigen (e.g., the complementarity determining regions (CDR)). The antigen-binding region can be derived from any animal species, such as rodents (e.g., mouse, rat, or hamster) and humans.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In some embodiments, the CDRs of the antibodies described herein have been determined according to the Kabat numbering scheme.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\epsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant (KA). The $K_D$ is calculated from the quotient of $k_{off}/k_{on}$, whereas KA is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody can be replaced with an amino acid residue with a similar side chain.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization can be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques. In some embodiments, the epitope of an antibody is determined using alanine scanning mutagenesis studies.

As used herein, the terms "immunospecifically binds," "immunospecifically recognizes," "specifically binds," and "specifically recognizes" are analogous terms in the context of antibodies and refer to molecules that bind to an antigen (e.g., epitope, immune complex, or binding partner of an antigen-binding site) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In some embodiments, molecules that immunospecifically bind to an antigen bind to the antigen with a $K_A$ that is at least 2 logs, 2.5 logs, 3 logs, 4 logs or greater than the $K_A$ when the molecules bind to another antigen.

In other embodiments, molecules that immunospecifically bind to an antigen do not cross react with other proteins under similar binding conditions. In some embodiments, molecules that immunospecifically bind to an antigen do not cross react with other proteins. In some embodiments, provided herein is a multispecific antibody that binds to a specified antigen with higher affinity than to another unrelated antigen. In certain embodiments, provided herein is a multispecific antibody that binds to a specified antigen (e.g., human serum albumin) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In some embodiments, the extent of binding of a multispecific antibody described herein to an unrelated, protein is less than 10%, 15%, or 20% of the binding of the antibody to the specified antigen as measured by, e.g., a radioimmunoassay.

In some embodiments, provided herein are multispecific antibodies that bind to a human antigen with higher affinity than to another species of the antigen. In certain embodiments, provided herein are multispecific antibodies that bind to a human antigen with a 5%, 10%, 15%, 20%, 25%, 30%, 35%, 40%, 45%, 50%, 55%, 60%, 65%, 70% or higher affinity than to another species as measured by, e.g., a radioimmunoassay, surface plasmon resonance, or kinetic exclusion assay. In some embodiments, the multispecific antibodies described herein, which bind to a human antigen, will bind to another species of the antigen protein with less than 10%, 15%, or 20% of the binding of the antibody to the human antigen protein as measured by, e.g., a radioimmunoassay, surface plasmon resonance, or kinetic exclusion assay.

As used herein, the term "host cell" can be any type of cell, e.g., a primary cell, a cell in culture, or a cell from a cell line. In embodiments, the term "host cell" refers to a cell transfected with a nucleic acid molecule and the progeny or potential progeny of such a cell. Progeny of such a cell cannot be identical to the parent cell transfected with the nucleic acid molecule, e.g., due to mutations or environmental influences that can occur in succeeding generations or integration of the nucleic acid molecule into the host cell genome.

As used herein, the term "effective amount" in the context of the administration of a therapy to a subject refers to the amount of a therapy that achieves a desired prophylactic or therapeutic effect.

As used herein, the terms "subject" and "patient" are used interchangeably. The subject can be an animal. In some embodiments, the subject is a mammal such as a non-primate (e.g., cow, pig, horse, cat, dog, rat, etc.) or a primate (e.g., monkey or human), or a human. In some embodiments, the subject is a cynomolgus monkey. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

Multispecific Antibodies

Disclosed herein are multispecific antibodies comprising a structural formula of:

wherein the antigen binding fragment (Fab) is a serum albumin Fab;

wherein $R^1$ and $R^2$ are bioactive effector moieties linked to an N-terminus of the Fab, each linked to a heavy chain variable domain or a light chain variable domain of the Fab;

wherein $R^3$ and $R^4$ are bioactive effector moieties linked to a C-terminus of the Fab, each linked to a heavy chain variable domain or a light chain variable domain of the Fab;

wherein m is 0 or an integer of 1, 2, 3, or greater; and wherein n is 0 or an integer of 1, 2, 3, or greater.

In some embodiments, $R^1$ and $R^2$ are same or different single-chain variable fragments (scFv) or same or different Fv fragments or disulfide-stabilized Fv (dsFv) fragments. In some embodiments, $R^3$ and $R^4$ are same or different scFv or Fv fragments or dsFv fragments.

In some embodiments, each of $R^1$, $R^2$, $R^3$, and $R^4$ can be linked to the Fab by one or more linkers. Each linker can comprise but is not limited to 1 to 20 amino acids or any length or range therein, such as 2, 3, 4, etc. Each linker can comprise an amino acid sequence having at least 90% identity to SEQ ID NO:3 or SEQ ID NO:4. Each linker can comprise an amino acid sequence of SEQ ID NO:3 or SEQ ID NO:4.

In some embodiments, the Fab comprises a heavy chain variable domain comprising (a) a heavy chain complementarity determining domain 1 (CDR1) comprising the amino acid sequence of SYGIS (SEQ ID NO:61), a heavy chain CDR2 comprising the amino acid sequence of WINTYSGGTKYAQKFQG (SEQ ID NO:62), and a heavy chain CDR3 comprising the amino acid sequence of LGHCQRGICSDALDT (SEQ ID NO:63);

(b) a heavy chain complementarity determining domain 1 (CDR1) comprising the amino acid sequence of SYGIS (SEQ ID NO:61), a heavy chain CDR2 comprising the amino acid sequence of RINTYNGNTGYAQRLQG (SEQ ID NO:64), and a heavy chain CDR3 comprising the amino acid sequence of LGHCQRGICSDALDT (SEQ ID NO:63);

(c) a heavy chain complementarity determining domain 1 (CDR1) comprising the amino acid sequence of NYGIH (SEQ ID NO:65), a heavy chain CDR2 comprising the amino acid sequence of SISYDGSNKYY-ADSVKG (SEQ ID NO:66), and a heavy chain CDR3 comprising the amino acid sequence of DVHYYGSGSYYNAFDI (SEQ ID NO:67);

(d) a heavy chain complementarity determining domain 1 (CDR1) comprising the amino acid sequence of SYAMS (SEQ ID NO:68), a heavy chain CDR2 comprising the amino acid sequence of VISHDGGFQYY-ADSVKG (SEQ ID NO:69), and a heavy chain CDR3 comprising the amino acid sequence of AGWLRQYGMDV (SEQ ID NO:70);

(e) a heavy chain complementarity determining domain 1 (CDR1) comprising the amino acid sequence of AYWIA (SEQ ID NO:71), a heavy chain CDR2 comprising the amino acid sequence of MIWPPDADA-RYSPSFQG (SEQ ID NO:72), and a heavy chain CDR3 comprising the amino acid sequence of LYSG-SYSP (SEQ ID NO:73); or (f) a heavy chain complementarity determining domain 1 (CDR1) comprising the amino acid sequence of AYSMN (SEQ ID NO:74), a heavy chain CDR2 comprising the amino acid sequence of SISSSGRYIHY-ADSVKG (SEQ ID NO:75), and a heavy chain CDR3 comprising the amino acid sequence of ETVMAGKA-LDY (SEQ ID NO:76).

In some embodiments, the Fab comprises a light chain variable domain comprising (g) a light chain complementarity determining domain 1 (CDR1) comprising the amino acid sequence of RASQ-SISRYLN (SEQ ID NO:77), a light chain CDR2 comprising the amino acid sequence of GASRLES (SEQ ID NO:78), and a light chain CDR3 comprising the amino acid sequence of QQSDSVPVT (SEQ ID NO:79);

(h) a light chain complementarity determining domain 1 (CDR1) comprising the amino acid sequence of RASQSISSYLN (SEQ ID NO:80), a light chain CDR2 comprising the amino acid sequence of AASSLQS (SEQ ID NO:81), and a light chain CDR3 comprising the amino acid sequence of QQSYSTPPYT (SEQ ID NO:82);

(i) a light chain complementarity determining domain 1 (CDR1) comprising the amino acid sequence of RASQSIFNYVA (SEQ ID NO:83), a light chain CDR2 comprising the amino acid sequence of DASNRAT (SEQ ID NO:84), and a light chain CDR3 comprising the amino acid sequence of QQRSKWPPTWT (SEQ ID NO:85);

(j) a light chain complementarity determining domain 1 (CDR1) comprising the amino acid sequence of RASETVSSRQLA (SEQ ID NO:86), a light chain CDR2 comprising the amino acid sequence of GASSRAT (SEQ ID NO:87), and a light chain CDR3 comprising the amino acid sequence of QQYGSSPRT (SEQ ID NO:88);

(k) a light chain complementarity determining domain 1 (CDR1) comprising the amino acid sequence of RASQSVSSSSLA (SEQ ID NO:89), a light chain CDR2 comprising the amino acid sequence of GASSRAT (SEQ ID NO:87), and a light chain CDR3 comprising the amino acid sequence of QKYSSYPLT (SEQ ID NO:90); or (l) a light chain complementarity determining domain 1 (CDR1) comprising the amino acid sequence of RASQSVGSNLA (SEQ ID NO:91), a light chain CDR2 comprising the amino acid sequence of GASTGAT (SEQ ID NO:92), and a light chain CDR3 comprising the amino acid sequence of QQYYSFLAKT (SEQ ID NO:93).

In some embodiments, the Fab comprises a heavy chain complementarity determining domain 1 (CDR1) comprising the amino acid sequence of AYSMN (SEQ ID NO:74), a heavy chain CDR2 comprising the amino acid sequence of SISSSGRYIHYADSVKG (SEQ ID NO:75), and a heavy chain CDR3 comprising the amino acid sequence of ETVMAGKALDY (SEQ ID NO:76), and a light chain complementarity determining domain 1 (CDR1) comprising the amino acid sequence of RASQSVGSNLA (SEQ ID NO:91), a light chain CDR2 comprising the amino acid sequence of GASTGAT (SEQ ID NO:92), and a light chain CDR3 comprising the amino acid sequence of QQYYSFLAKT (SEQ ID NO:93), or any combinations of the heavy chain CDR1, CDR2, and CDR3 and light chain CDR1, CDR2, and CDR3 disclosed above.

In some embodiments, the Fab comprises a heavy chain variable domain comprising an amino acid sequence having at least 80%, at least 85%, at least 90%, at least 93%, at least 95%, at least 96%, at least 97%, at least 98%, at least 99%, or 100% identity to SEQ ID NO:94, 95, 96, 97, 98, or 99.

In some embodiments, the Fab comprises a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:100, 101, 102, 103, 104, or 105.

In some embodiments, the Fab comprises a heavy chain variable domain comprising an amino acid sequence having at least 80%, at least 85%, at least 90%, at least 93%, at least 95%, at least 96%, at least 97%, at least 98%, at least 99%, or 100% identity to SEQ ID NO:94, 95, 96, 97, 98, or 99, and a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:100, 101, 102, 103, 104, or 105, respectively or any combinations of heavy chain variable domain and light chain variable domain disclosed herein. For example, the Fab can comprise a heavy chain variable domain comprising an amino acid sequence having at least 80%, at least 85%, at least 90%, at least 93%, at least 95%, at least 96%, at least 97%, at least 98%, at least 99%, or 100% identity to SEQ ID NO:99 and a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:105.

In some embodiments, the Fab comprises a heavy chain domain comprising an amino acid sequence having at least 80%, at least 85%, at least 90%, at least 93%, at least 95%, at least 96%, at least 97%, at least 98%, at least 99%, or 100% identity to SEQ ID NO:45 ($V_H$-$C_{H1}$ domain) and a light chain domain comprising an amino acid sequence having at least 80%, at least 85%, at least 90%, at least 93%, at least 95%, at least 96%, at least 97%, at least 98%, at least 99%, or 100% identity to SEQ ID NO:46 ($V_L$-$C_L$ domain).

In some embodiments, each of the $R^1$, $R^2$, $R^3$ and $R^4$ can be a bioactive effector moiety, such as an anti-CD40L hu5c8 scFv. For example, each of the $R^1$, $R^2$, $R^3$ and $R^4$ can be an anti-CD40L hu5c8 scFv comprising an amino acid sequence at least 80%, at least 85%, at least 90%, at least 93%, at least 95%, at least 96%, at least 97%, at least 98%, at least 99%, or 100% identity to SEQ ID NO:47 or SEQ ID NO:48. Each of the $R^1$, $R^2$, $R^3$ and $R^4$ can be an anti-CD40L hu5c8 scFv comprising an amino acid sequence of SEQ ID NO:47 or SEQ ID NO:48.

In some embodiments, each of the $R^1$ and $R^2$ can be a bioactive effector moiety, such as an anti-CD40L hu5c8 scFv. For example, each of the $R^1$ and $R^2$ can be an anti-CD40L hu5c8 scFv comprising an amino acid sequence at least 80%, at least 85%, at least 90%, at least 93%, at least 95%, at least 96%, at least 97%, at least 98%, at least 99%, or 100% identity to SEQ ID NO:47 or SEQ ID NO:48. Each of the $R^1$ and $R^2$ can be an anti-CD40L hu5c8 scFv comprising an amino acid sequence of SEQ ID NO:47 or SEQ ID NO:48.

In some embodiments, each of $R^1$, $R^2$, $R^3$ and $R^4$ is one or more bioactive effector moieties comprising, e.g., anti-TNF-α Fv, anti-TNF-α disulfide-stabilized Fv (dsFv), anti-IL-23 Fv, anti-IL-23 dsFv, anti-IFNAR1, and/or anti-IFNAR1 dsFv.

In some embodiments, each of $R^3$ and $R^4$ is one or more bioactive effector moieties comprising, e.g., anti-TNF-α Fv, anti-TNF-α disulfide-stabilized Fv (dsFv), anti-IL-23 Fv, anti-IL-23 dsFv, anti-IFNAR1, and/or anti-IFNAR1 dsFv.

In some embodiments, each of $R^1$, $R^2$, $R^3$ and $R^4$ can be one or more bioactive effector moieties comprising an anti-TNF-α Fv comprising a heavy chain amino acid sequence having at least 80%, at least 85%, at least 90%, at least 93%, at least 95%, at least 96%, at least 97%, at least 98%, at least 99%, or 100% identity to SEQ ID NO:49 and a light chain amino acid sequence having at least 80%, at least 85%, at least 90%, at least 93%, at least 95%, at least 96%, at least 97%, at least 98%, at least 99%, or 100% identity to SEQ ID NO:50, anti-TNF-α disulfide-stabilized Fv (dsFv) comprising a heavy chain amino acid sequence having at least 80%, at least 85%, at least 90%, at least 93%, at least 95%, at least 96%, at least 97%, at least 98%, at least 99%, or 100% identity to SEQ ID NO:51 and a light chain amino acid sequence having at least 80%, at least 85%, at least 90%, at least 93%, at least 95%, at least 96%, at least 97%, at least 98%, at least 99%, or 100% identity to SEQ ID NO:52, anti-IL-23 Fv comprising a heavy chain amino acid sequence having at least 80%, at least 85%, at least 90%, at least 93%, at least 95%, at least 96%, at least 97%, at least 98%, at least 99%, or 100% identity to SEQ ID NO:53 and a light chain amino acid sequence having at least 80%, at least 85%, at least 90%, at least 93%, at least 95%, at least 96%, at least 97%, at least 98%, at least 99%, or 100% identity to SEQ ID NO:54, anti-IL-23 dsFv comprising a heavy chain amino acid sequence having at least 80%, at least 85%, at least 90%, at least 93%, at least 95%, at least 96%, at least 97%, at least 98%, at least 99%, or 100% identity to SEQ ID NO:55 and a light chain amino acid sequence having at least 80%, at least 85%, at least 90%, at least 93%, at least 95%, at least 96%, at least 97%, at least 98%, at least 99%, or 100% identity to SEQ ID NO:56, anti-IFNAR1 comprising a heavy chain amino acid sequence having at least 80%, at least 85%, at least 90%, at least 93%, at least 95%, at least 96%, at least 97%, at least 98%, at least 99%, or 100% identity to SEQ ID NO:57 and a light chain amino acid sequence having at least 80%, at least 85%, at least 90%, at least 93%, at least 95%, at least 96%, at least 97%, at least 98%, at least 99%, or 100% identity to SEQ ID NO:58, and/or anti-IFNAR1 dsFv comprising a heavy chain amino acid sequence having at least 80%, at least 85%, at least 90%, at least 93%, at least 95%, at least 96%, at least 97%, at least 98%, at least 99%, or 100% identity to SEQ ID NO:59 and a light chain amino acid sequence having at least 80%, at least 85%, at least 90%, at least 93%, at least 95%, at least 96%, at least 97%, at least 98%, at least 99%, or 100% identity to SEQ ID NO:60. Each of $R^1$, $R^2$, $R^3$ and $R^4$ can be one or more bioactive effector moieties comprising an anti-TNF-α Fv comprising a heavy chain of SEQ ID NO:49 and a light chain of SEQ ID NO:50, anti-TNF-α disulfide-stabilized Fv (dsFv) comprising a heavy chain of SEQ ID NO:51 and a light chain of SEQ ID NO:52, anti-IL-23 Fv comprising a heavy chain of SEQ ID NO:53 and a light chain of SEQ ID NO:54, anti-IL-23 dsFv comprising a heavy chain of SEQ ID NO:55 and a light chain of SEQ ID NO:56, anti-IFNAR1 comprising a heavy chain of SEQ ID NO:57 and a light chain of SEQ ID NO:58, and/or anti-IFNAR1 dsFv comprising a heavy chain of SEQ ID NO:59 and a light chain of SEQ ID NO:60.

In some embodiments, each of $R^3$ and $R^4$ can be one or more bioactive effector moieties comprising an anti-TNF-α Fv comprising a heavy chain amino acid sequence having at least 80%, at least 85%, at least 90%, at least 93%, at least 95%, at least 96%, at least 97%, at least 98%, at least 99%, or 100% identity to SEQ ID NO:49 and a light chain amino acid sequence having at least 80%, at least 85%, at least 90%, at least 93%, at least 95%, at least 96%, at least 97%, at least 98%, at least 99%, or 100% identity to SEQ ID NO:50, anti-TNF-α disulfide-stabilized Fv (dsFv) comprising a heavy chain amino acid sequence having at least 80%, at least 85%, at least 90%, at least 93%, at least 95%, at least 96%, at least 97%, at least 98%, at least 99%, or 100% identity to SEQ ID NO:51 and a light chain amino acid sequence having at least 80%, at least 85%, at least 90%, at least 93%, at least 95%, at least 96%, at least 97%, at least 98%, at least 99%, or 100% identity to SEQ ID NO:52, anti-IL-23 Fv comprising a heavy chain amino acid sequence having at least 80%, at least 85%, at least 90%, at least 93%, at least 95%, at least 96%, at least 97%, at least 98%, at least 99%, or 100% identity to SEQ ID NO:53 and a light chain amino acid sequence having at least 80%, at least 85%, at least 90%, at least 93%, at least 95%, at least 96%, at least 97%, at least 98%, at least 99%, or 100% identity to SEQ ID NO:54, anti-IL-23 dsFv comprising a heavy chain amino acid sequence having at least 80%, at least 85%, at least 90%, at least 93%, at least 95%, at least 96%, at least 97%, at least 98%, at least 99%, or 100% identity to SEQ ID NO:55 and a light chain amino acid sequence having at least 80%, at least 85%, at least 90%, at least 93%, at least 95%, at least 96%, at least 97%, at least 98%, at least 99%, or 100% identity to SEQ ID NO:56, anti-IFNAR1 comprising a heavy chain amino acid sequence having at least 80%, at least 85%, at least 90%, at least 93%, at least 95%, at least 96%, at least 97%, at least 98%, at least 99%, or 100% identity to SEQ ID NO:57 and a light chain amino acid sequence having at least 80%, at least 85%, at least 90%, at least 93%, at least 95%, at least 96%, at least 97%, at least 98%, at least 99%, or 100% identity to SEQ ID NO:58, and/or anti-IFNAR1 dsFv comprising a heavy chain amino acid sequence having at least 80%, at least 85%, at least 90%, at least 93%, at least 95%, at least 96%, at least 97%, at least 98%, at least 99%, or 100% identity to SEQ ID NO:59 and a light chain amino acid sequence having at least 80%, at least 85%, at least 90%, at least 93%, at least 95%, at least 96%, at least 97%, at least 98%, at least 99%, or 100% identity to SEQ ID NO:60. Each of $R^3$ and $R^4$ can be one or more bioactive effector moieties comprising an anti-TNF-α Fv comprising a heavy chain of SEQ ID NO:49 and a light chain of SEQ ID NO:50, anti-TNF-α disulfide-stabilized Fv (dsFv) comprising a heavy chain of SEQ ID NO:51 and a light chain of SEQ ID NO:52, anti-IL-23 Fv comprising a heavy chain of SEQ ID NO:53 and a light chain of SEQ ID NO:54, anti-IL-23 dsFv comprising a heavy chain of SEQ ID NO:55 and a light chain of SEQ ID NO:56, anti-IFNAR1 comprising a heavy chain of SEQ ID NO:57 and a light chain of SEQ ID NO:58, and/or anti-IFNAR1 dsFv comprising a heavy chain of SEQ ID NO:59 and a light chain of SEQ ID NO:60.

In some embodiments, the multispecific antibody disclosed herein comprises an anti-HSA Fab (SL335), $R^1$ and $R^2$ that are each anti-CD40L IgG (ruplizumab), and $R^3$ and $R^4$ that are each anti-TNF-α IgG (adalimumab), and/or anti-TNF-α Fab' (certolizumab). In some embodiments, the multispecific antibody disclosed herein comprises anti-HSA Fab (SL335), $R^1$ and $R^2$ that are each anti-CD40L scFv (hu5c8), and m and n of $R^3$m and $R^4$n that are each 0.

In certain aspects, a multispecific antibody described herein can be described by its VL domain alone, or its VH domain alone, or by its 3 VL CDRs alone, or its 3 VH CDRs alone. See, for example, Rader C et al., (1998) PNAS 95: 8910-8915, which is incorporated herein by reference in its entirety, describing the humanization of the mouse anti-avß33 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are multispecific antibodies that specifically bind to serum albumin (e.g., human serum albumin) and comprise the Chothia VL CDRs of a VL. In certain aspects, provided herein are antibodies that specifically bind to serum albumin (e.g., human serum albumin) and comprise the Chothia VH CDRs of a VH. In certain aspects, provided herein are antibodies that specifically bind to serum albumin (e.g., human serum albumin) and comprise the Chothia VL CDRs of a VL and comprise the Chothia VH CDRs of a VH. In certain embodiments, antibodies that specifically bind to serum albumin (e.g., human serum albumin) comprise one or more CDRs, in which the Chothia and Kabat CDRs have the same amino acid sequence. In certain embodiments, provided herein are antibodies that specifically bind to serum albumin (e.g., human serum albumin) and comprise combinations of Kabat CDRs and Chothia CDRs.

In certain aspects, the CDRs of an antibody can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

In certain aspects, the CDRs of an antibody can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001).

In certain aspects, the CDRs of an antibody can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.).

In some embodiments, the position of one or more CDRs along the VH (e.g., CDR1, CDR2, or CDR3) and/or VL (e.g., CDR1, CDR2, or CDR3) region of an antibody described herein can vary by one, two, three, four, five, or six amino acid positions so long as immunospecific binding to an antigen is maintained (e.g., substantially maintained, for example, at least 50%, at least 60%, at least 70%, at least 80%, at least 90%, at least 95%). For example, the position defining a CDR of an antibody described herein can vary by shifting the N-terminal and/or C-terminal boundary of the CDR by one, two, three, four, five, or six amino acids, relative to the CDR position of a multispecific antibody described herein, so long as immunospecific binding to the antigen(s) is maintained (e.g., substantially maintained, for example, at least 50%, at least 60%, at least 70%, at least 80%, at least 90%, at least 95%). In other embodiments, the length of one or more CDRs along the VH (e.g., CDR1, CDR2, or CDR3) and/or VL (e.g., CDR1, CDR2, or CDR3) region of an antibody described herein can vary (e.g., be shorter or longer) by one, two, three, four, five, or more amino acids, so long as immunospecific binding to the antigen(s) is maintained (e.g., substantially maintained, for example, at least 50%, at least 60%, at least 70%, at least 80%, at least 90%, at least 95%).

In some embodiments, a VL CDR1, VL CDR2, VL CDR3, VH CDR1, VH CDR2, and/or VH CDR3 described herein can be one, two, three, four, five or more amino acids shorter than one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, a VL CDR1, VL CDR2, VL CDR3, VH CDR1, VH CDR2, and/or VH CDR3 described herein can be one, two, three, four, five or more amino acids longer than one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the amino terminus of a VL CDR1, VL CDR2, VL CDR3, VH CDR1, VH CDR2, and/or VH CDR3 described herein can be extended by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the carboxy terminus of a VL CDR1, VL CDR2, VL CDR3, VH CDR1, VH CDR2, and/or VH CDR3 described herein can be extended by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the amino terminus of a VL CDR1, VL CDR2, VL CDR3, VH CDR1, VH CDR2, and/or VH CDR3 described herein can be shortened by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In some embodiments, the carboxy terminus of a VL CDR1, VL CDR2, VL CDR3, VH CDR1, VH CDR2, and/or VH CDR3 described herein can be shortened by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). Any method known in the art can be used to ascertain whether immunospecific binding to the antigen(s) is maintained, for example, the binding assays and conditions described in the "Examples" section herein.

The determination of percent identity between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, nonlimiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

A multispecific antibody can be fused or conjugated (e.g., covalently or noncovalently linked) to a detectable label or substance. Examples of detectable labels or substances include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labeled antibodies can be used to detect antigen proteins.

By way of example, in order to suppress a CD40-CD40L interaction, which is a major route of an autoimmune disease or an allograft rejection response, there has been developed a monoclonal antibody targeting CD40 or CD40L, but additional development thereof stopped due to incidence of a side effect, such as thromboembolism, induced by the Fc of IgG1 antibody. To eliminate or reduce side effects, a recombinant antibody (anti-hu5c8 scFv)$_2$-SL335 (termed APB-A1) produced by combining Fab with anti-CD40L scFv was developed. SL335 is an antigen-binding fragment (Fab) that has increased in vivo sustainability by specifically binding to the human serum albumin. See U.S. Pat. No. 9,879,077, incorporated herein by reference in its entirety.

To identify the binding capacity of APB-A1 and its potency of suppressing thromboembolism, binding capacity and the cell-based suppressive potency were evaluated. The binding affinities of APB-A1 to HSA and rhCD40L were identified by bilayer interferometry, and the result showed that the dissociation constants (KD) of APB-A1 for HSA and rhCD40L tended to decrease, compared to each control group. In evaluating the cell-based suppressive potency, when HSA was added, there was no significant difference in the suppressive potency of hu5c8 IgG1, while the binding suppressive potency levels of APB-A1 for rhCD40L antigen and D1.1 cell were increased about 1.6 times and 3 times, respectively. This suggests that a size change caused by the binding of SL335 and HSA leads to a potency level similar to that of the positive control group. That is to say, the suppressive potency was increased in the presence of HSA even with a lower affinity than hu5c8 IgG1.

To investigate whether the thromboembolism side effect due to the removal of an Fc region of IgG1 is solved or not, the rate of platelet aggregation and the level of serotonin secretion of APB-A1 were measured and analyzed. Although platelet aggregation was not observed from the immune complex (IC) formed by APB-A1 and rhCD40L even at a high concentration of 400 ng/mℓ, an aggregation response to the IC of hu5c8 IgG1 and rhCD40L was initiated at a relatively low concentration of 60 ng/mℓ, which was identified by the transmittance and the rate of platelet aggregation. When a serotonin release level were analyzed in dense platelet granules, it was identified that the serotonin release level of APB-A1 IC was statistically significantly lower than that the hu5c8 IgG1 IC. This result suggests that the anti-CD40L antibody of the present disclosure can effectively solve the thromboembolism-related disorder even in vivo.

For assessment of the half-life of APB-A1, pharmacokinetic analysis was conducted. APB-A1 was administered to two test groups of cynomolgus monkeys at a dose of each 5 mg/kg (group 1) or each 20 mg/kg (group 2) through a single intravenous injection. As a result, on the assumption that the 2 groups have an equal renal clearance rate, it was identified that the in vivo half-life of the group 2 was 9.59±0.79 days, which is 1.38 times higher than that of the group 1, that is, 6.94±4.6 days.

In yet another example, to evaluate the immune response to an anti-TT IgG antibody generated when injecting tetanus toxoid (TT), pharmacodynamics analysis was conducted. Cynomolgus monkeys were used as test animals, APB-A1 was administered to two test groups of cynomolgus monkeys at a dose of 5 mg/kg (group 1) or 20 mg/kg (group 2) through a single intravenous injection. As a result, when APB-A1 was intravenously administered at a high concentration (20 mg/kg), the suppressive potency for the IgG antibody immune response was much higher than when DXT as a positive control group was administered, and this suppressive potency was maintained for up to 30 to 40 days. In addition, the CD40-CD40L interaction is also operated by a memory B cell, and a significant suppressive efficacy was identified with APB-A1 on day 27 with TT boosting (on day 20). Therefore, it was confirmed that the APB-A1 of the present disclosure markedly improved the thromboembolism-related disorder, compared to hu5c8 IgG1.

In yet other embodiments, new bispecific antibodies, termed APB-B1a and APB-B1b, respectively, were produced by linking an anti-CD154 (CD40 ligand; CD40L)

single chain variable fragment (scFv) (V$_H$-[peptide linker]-V$_L$) and a tumor necrosis factor-alpha (anti-TNF-α) variable fragment (Fv) or disulfide-stabilized Fv (dsFv). In the experiment using a bio-layer interferometry (BLI), it was confirmed that APB-B1 possessed the capacity of simultaneously binding to three targets, that is, recombinant human CD40L, recombinant human TNF-α and human serum albumin (HSA) proteins, and similar level of antigen-binding affinity to that of anti-CD40L IgG or anti-TNF-α Fab' parental antibody.

In other embodiments related thereto, the melting temperature (Tm) measured in an excipient-free buffered state was 62° C., regardless of the presence or absence of inter-chain disulfide bond in anti-TNF-α Fv, confirming that the inter-chain disulfide bond did not contribute to the structural stability.

In yet other embodiments related thereto, the in vitro cell-based assay showed that the CD40L inhibiting capacity of APB-B1 was similar to that of the parental antibody anti-CD40L IgG1, and the TNF-α inhibiting capacity was slightly reduced, compared to the parental antibody anti-TNF-α Fab'. Nevertheless, APB-B1 demonstrated an inhibitory activity to both of CD40L and TNF-α and a higher inhibitory activity than each of the parental antibodies, anti-CD40L IgG1 and anti-TNF-α Fab'.

Antibody Production

Multispecific antibodies disclosed herein can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In some embodiments, a multispecific antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In some aspects, provided herein is a method of making a multispecific antibody disclosed herein comprising culturing a cell or host cell described herein. In some aspects, provided herein is a method of making a multispecific antibody comprising expressing (e.g., recombinantly expressing) the antibody using a cell or host cell described herein (e.g., a cell or a host cell comprising polynucleotides encoding an antibody described herein). In some embodiments, the cell is an isolated cell. In some embodiments, the exogenous polynucleotides have been introduced into the cell. In some embodiments, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Multispecific antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein.

A "monoclonal antibody," as used herein, is an antibody produced by a single cell (e.g., hybridoma or host cell producing a recombinant antibody), wherein the antibody immunospecifically binds to an antigen (e.g., human serum albumin) as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody can be a Fab fragment or a F(ab')$_2$ fragment. Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the antigen (e.g., human serum albumin)) used for immunization. Alternatively, lymphocytes can be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., human serum albumin)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that can contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against an antigen. The binding specificity of monoclonal antibodies produced by hybridoma cells is determined by methods known in the art, for example, immunoprecipitation or by an in vitro binding assay, such as radioimmunoas say (RIA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of a tetrameric antibody molecule and contains the complete light chain paired with the VH and CH1 domains of the heavy chain. A F(ab')$_2$ fragment contains the two antigen-binding arms of a tetrameric antibody molecule linked by disulfide bonds in the hinge region.

Further, the antibodies described herein can also be generated using various phage display methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antibody that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT/GB91/001134; WO90/02809, WO91/10737, WO92/01047, WO92/18619, WO93/11236, WO95/15982, WO95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate antibodies, including human antibodies, and expressed in any desired host, including mammalian cells, insect cells, plant cells, yeast, and bacteria, e.g., as described below. Techniques to recombinantly produce antibodies such as Fab, Fab' and F(ab')$_2$ fragments can also be employed using methods known in the art such as those disclosed in WO92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In some aspects, to generate antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221;

Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (EP 239400; WO91/09967; and U.S. Pat. Nos. 5,225,539, 5,530,101, and 5,585,089), veneering or resurfacing (EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, WO93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also US 2005/0042664 A1 (Feb. 24, 2005), which is incorporated by reference herein in its entirety.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and WO94/04678, WO94/25591 and WO01/44301.

Further, antibodies that immunospecifically bind to an antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, a multispecific antibody described herein, which binds to the same epitope of an antigen of interest (e.g., human serum albumin) as an antibody described herein, is a human antibody. In particular embodiments, an antibody described herein, which competitively blocks (e.g., in a dose-dependent manner) any one of the antibodies described herein from binding to serum albumin (e.g., human serum albumin), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered nonfunctional separately or simultaneously with the introduction of human immunoglobulin loci by homologous recombination. In particular, homozygous deletion of the hi region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., WO98/24893, WO96/34096 and WO96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which specifically bind to an antigen can be made by a variety of methods known in the art including phage display methods described above using antibody libraries derived from human immunoglobulin sequences. See also U.S. Pat. Nos. 4,444,887, 4,716,111, and 5,885,793; and WO98/46645, WO98/50433, WO98/24893, WO98/16654, WO96/34096, WO96/33735, and WO91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen. Such methods are known and are described in the art, see, e.g., Shinmoto H et al., (2004) Cytotechnology 46: 19-23; Naganawa Y et al., (2005) Human Antibodies 14: 27-31.

Polynucleotides, Vectors, and Cells

In certain aspects, provided herein are polynucleotides comprising a nucleotide sequence encoding an antibody described herein or a fragment thereof (e.g., a variable light chain region and/or variable heavy chain region) that immunospecifically binds to an antigen, and vectors, e.g., vectors comprising such polynucleotides for recombinant expression in host cells (e.g., *E. coli* and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In some embodiments, a nucleic acid molecule(s) encoding an antibody described herein is isolated or purified.

In particular aspects, provided herein are polynucleotides comprising nucleotide sequences encoding antibodies, which immunospecifically bind to an antigen polypeptide (e.g., human serum albumin) and comprises an amino acid sequence as described herein, as well as antibodies that compete with such antibodies for binding to an antigen polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein. The polynucleotides can comprise nucleotide sequences encoding a heavy chain comprising the VH FRs and CDRs of antibodies described herein.

In specific embodiments, provided herein are polynucleotides comprising a nucleotide sequence encoding a multispecific antibody comprising a Fab comprising three VH chain CDRs, e.g., containing VL CDR1, VL CDR2, and VL CDR3 of an antibody to human serum albumin described herein and three VH chain CDRs, e.g., containing VH CDR1, VH CDR2, and VH CDR3 of an antibody to human serum albumin described herein.

In particular embodiments, provided herein are polynucleotides comprising a nucleotide sequence encoding a multispecific antibody or a fragment thereof comprising a VL domain.

In certain embodiments, a polynucleotide described herein comprises a nucleotide sequence encoding a multispecific antibody provided herein comprising a light chain variable region comprising an amino acid sequence described herein (e.g., SEQ ID NO:46), wherein the antibody immunospecifically binds to serum albumin (e.g., human serum albumin).

In certain embodiments, a polynucleotide described herein comprises a nucleotide sequence encoding an antibody provided herein comprising a heavy chain variable region comprising an amino acid sequence described herein (e.g., SEQ ID NO:45), wherein the antibody immunospecifically binds to serum albumin (e.g., human serum albumin).

In specific aspects, provided herein is a polynucleotide comprising a nucleotide sequence encoding an antibody comprising a light chain and a heavy chain, e.g., a separate light chain and heavy chain. With respect to the light chain, in some embodiments, a polynucleotide provided herein comprises a nucleotide sequence encoding a kappa light chain. In other embodiments, a polynucleotide provided herein comprises a nucleotide sequence encoding a lambda light chain. In yet other embodiments, a polynucleotide provided herein comprises a nucleotide sequence encoding an antibody described herein comprising a human kappa light chain or a human lambda light chain. In some embodiments, a polynucleotide provided herein comprises a nucleotide sequence encoding an antibody, which immunospecifically binds to serum albumin (e.g., human serum albumin), wherein the antibody comprises a light chain, and wherein the amino acid sequence of the VL domain can comprise the amino acid sequence set forth in SEQ ID NO:46 and wherein the constant region of the light chain comprises the amino acid sequence of a human kappa light chain constant region. For example, human constant region sequences can be those described in U.S. Pat. No. 5,693,780.

Also provided herein are polynucleotides encoding a multispecific antibody or a fragment thereof that are optimized, e.g., by codon/RNA optimization, replacement with heterologous signal sequences, and elimination of mRNA instability elements. Methods to generate optimized nucleic acids encoding a multispecific antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding a multispecific antibody described herein or a fragment thereof (e.g., VL domain or VH domain) can hybridize to an antisense (e.g., complementary) polynucleotide of an unoptimized polynucleotide sequence encoding a multispecific antibody described herein or a fragment thereof (e.g., VL domain or VH domain). In specific embodiments, an optimized nucleotide sequence encoding a multispecific antibody described herein or a fragment hybridizes under high stringency conditions to antisense polynucleotide of an unoptimized polynucleotide sequence encoding a multispecific antibody described herein or a fragment thereof. In some embodiments, an optimized nucleotide sequence encoding a multispecific antibody described herein or a fragment thereof hybridizes under high stringency, intermediate or lower stringency hybridization conditions to an antisense polynucleotide of an unoptimized nucleotide sequence encoding a multispecific antibody described herein or a fragment thereof. Information regarding hybridization conditions has been described, see, e.g., US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-246), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, such as poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding multispecific antibodies described herein can be readily isolated and sequenced using conventional procedures (e.g., by using oligonucleotide probes that are capable of binding specifically to genes encoding the heavy and light chains of the multispecific antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of multispecific antibodies in the recombinant host cells.

To generate antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6×sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

Further disclosed herein are expression vectors comprising:
(a) a promoter,
(b) a first nucleic acid molecule encoding an antigen binding fragment (Fab) that binds to serum albumin, and
(c) a second nucleic acid molecule encoding a bioactive effector moiety and a linker,
wherein the promoter, the first nucleic acid sequence, and the second nucleic acid molecules are operably linked. The second nucleic acid molecule can encode 2, 3, 4, 5, 6, or more bioactive effector moieties and linkers.

In some embodiments, the first nucleic acid molecule comprises a nucleic acid sequence encoding a Fab comprising a heavy chain variable domain comprising
(a) a heavy chain complementarity determining domain 1 (CDR1) comprising the amino acid sequence of SYGIS (SEQ ID NO:61),
 a heavy chain CDR2 comprising the amino acid sequence of WINTYSGGTKYAQKFQG (SEQ ID NO:62), and
 a heavy chain CDR3 comprising the amino acid sequence of LGHCQRGICSDALDT (SEQ ID NO:63);
(b) a heavy chain complementarity determining domain 1 (CDR1) comprising the amino acid sequence of SYGIS (SEQ ID NO:61),
 a heavy chain CDR2 comprising the amino acid sequence of RINTYNGNTGYAQRLQG (SEQ ID NO:64), and
 a heavy chain CDR3 comprising the amino acid sequence of LGHCQRGICSDALDT (SEQ ID NO:63);

(c) a heavy chain complementarity determining domain 1 (CDR1) comprising the amino acid sequence of NYGIH (SEQ ID NO:65),
a heavy chain CDR2 comprising the amino acid sequence of SISYDGSNKYYADSVKG (SEQ ID NO:66), and
a heavy chain CDR3 comprising the amino acid sequence of DVHYYGSGSYYNAFDI (SEQ ID NO:67);
(d) a heavy chain complementarity determining domain 1 (CDR1) comprising the amino acid sequence of SYAMS (SEQ ID NO:68),
a heavy chain CDR2 comprising the amino acid sequence of VISHDGGFQYYADSVKG (SEQ ID NO:69), and
a heavy chain CDR3 comprising the amino acid sequence of AGWLRQYGMDV (SEQ ID NO:70);
(e) a heavy chain complementarity determining domain 1 (CDR1) comprising the amino acid sequence of AYWIA (SEQ ID NO:71),
a heavy chain CDR2 comprising the amino acid sequence of MIWPPDADARYSPSFQG (SEQ ID NO:72), and
a heavy chain CDR3 comprising the amino acid sequence of LYSGSYSP (SEQ ID NO:73); or
(f) a heavy chain complementarity determining domain 1 (CDR1) comprising the amino acid sequence of AYSMN (SEQ ID NO:74),
a heavy chain CDR2 comprising the amino acid sequence of SISSSGRYIHYADSVKG (SEQ ID NO:75), and
a heavy chain CDR3 comprising the amino acid sequence of ETVMAGKALDY (SEQ ID NO:76).

In some embodiments, the first nucleic acid molecule comprises a nucleic acid sequence encoding a Fab comprising a light chain variable domain comprising (g) a light chain complementarity determining domain 1 (CDR1) comprising the amino acid sequence of RASQSISRYLN (SEQ ID NO:77),
a light chain CDR2 comprising the amino acid sequence of GASRLES (SEQ ID NO:78), and
a light chain CDR3 comprising the amino acid sequence of QQSDSVPVT (SEQ ID NO:79);
(h) a light chain complementarity determining domain 1 (CDR1) comprising the amino acid sequence of RASQSISSYLN (SEQ ID NO:80),
a light chain CDR2 comprising the amino acid sequence of AASSLQS (SEQ ID NO:81), and
a light chain CDR3 comprising the amino acid sequence of QQSYSTPPYT (SEQ ID NO:82);
(i) a light chain complementarity determining domain 1 (CDR1) comprising the amino acid sequence of RASQSIFNYVA (SEQ ID NO:83),
a light chain CDR2 comprising the amino acid sequence of DASNRAT (SEQ ID NO:84), and
a light chain CDR3 comprising the amino acid sequence of QQRSKWPPTWT (SEQ ID NO:85);
(j) a light chain complementarity determining domain 1 (CDR1) comprising the amino acid sequence of RASETVSSRQLA (SEQ ID NO:86),
a light chain CDR2 comprising the amino acid sequence of GASSRAT (SEQ ID NO:87), and
a light chain CDR3 comprising the amino acid sequence of QQYGSSPRT (SEQ ID NO:88);
(k) a light chain complementarity determining domain 1 (CDR1) comprising the amino acid sequence of RASQSVSSSSLA (SEQ ID NO:89),
a light chain CDR2 comprising the amino acid sequence of GASSRAT (SEQ ID NO:87), and
a light chain CDR3 comprising the amino acid sequence of QKYSSYPLT (SEQ ID NO:90); or
(l) a light chain complementarity determining domain 1 (CDR1) comprising the amino acid sequence of RASQSVGSNLA (SEQ ID NO:91),
a light chain CDR2 comprising the amino acid sequence of GASTGAT (SEQ ID NO:92), and
a light chain CDR3 comprising the amino acid sequence of QQYYSFLAKT (SEQ ID NO:93).

For example, the first nucleic acid molecule can comprise a nucleic acid sequence encoding a Fab comprising: a heavy chain variable domain comprising (a) above and a light chain variable domain comprising (g) above; a heavy chain variable domain comprising (b) above and a light chain variable domain comprising (h) above; a heavy chain variable domain comprising (c) above and a light chain variable domain comprising (i) above; a heavy chain variable domain comprising (d) above and a light chain variable domain comprising (j) above; a heavy chain variable domain comprising (e) above and a light chain variable domain comprising (k) above; a heavy chain variable domain comprising (f) above and a light chain variable domain comprising (l) above; or any combination of a heavy chain variable domain above and a light chain variable domain above. In some embodiments, the first nucleic acid molecule comprises a nucleic acid sequence encoding a Fab (SL335) comprising a heavy chain complementarity determining domain 1 (CDR1) comprising the amino acid sequence of AYSMN (SEQ ID NO:74), a heavy chain CDR2 comprising the amino acid sequence of SISSSGRYIHYADSVKG (SEQ ID NO:75), and a heavy chain CDR3 comprising the amino acid sequence of ETVMAGKALDY (SEQ ID NO:76), and a light chain complementarity determining domain 1 (CDR1) comprising the amino acid sequence of RASQSVGSNLA (SEQ ID NO:91), a light chain CDR2 comprising the amino acid sequence of GASTGAT (SEQ ID NO:92), and a light chain CDR3 comprising the amino acid sequence of QQYYSFLAKT (SEQ ID NO:93).

In other embodiments, the first nucleic acid molecule comprises a nucleic acid sequence encoding a Fab comprising a heavy chain variable domain comprising an amino acid sequence having at least 80%, at least 85%, at least 90%, at least 93%, at least 95%, at least 96%, at least 97%, at least 98%, at least 99%, or 100% identity to SEQ ID NO:94, 95, 96, 97, 98, or 99.

In some embodiments, the first nucleic acid molecule comprises a nucleic acid sequence encoding a Fab comprising a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:100, 101, 102, 103, 104, or 105.

In some embodiments, the first nucleic acid molecule comprises a nucleic acid sequence encoding a Fab comprising a heavy chain variable domain comprising an amino acid sequence having at least 80%, at least 85%, at least 90%, at least 93%, at least 95%, at least 96%, at least 97%, at least 98%, at least 99%, or 100% identity to SEQ ID NO:94, 95, 96, 97, 98, or 99, and a light chain variable domain comprising an amino acid sequence having at least 80%, at least 85%, at least 90%, at least 93%, at least 95%, at least 96%, at least 97%, at least 98%, at least 99%, or 100% identity to SEQ ID NO:100, 101, 102, 103, 104, or 105, respectively.

In some embodiments, the first nucleic acid molecule comprises a nucleic acid sequence encoding a Fab (SL335)

comprising a heavy chain domain comprising an amino acid sequence of SEQ ID NO:45 ($V_H$-$C_{H1}$ domain) and a light chain domain comprising an amino acid sequence of SEQ ID NO:46 ($V_L$-$C_L$ domain).

In some embodiments, the bioactive effector moieties are anti-TNF-α Fv, anti-TNF-α dsFv, anti-IL-23 Fv, anti-IL-23 dsFv, anti-IFNAR1 Fv, and/or anti-IFNAR1 dsFv. For example, the second nucleic acid molecule can comprise a nucleotide sequence encoding the amino acid sequence having at least 80%, at least 85%, at least 90%, at least 93%, at least 95%, at least 96%, at least 97%, at least 98%, at least 99%, or 100% identity to one or more of SEQ ID NOs: 49-60. In some embodiments, the second nucleic acid molecule can comprise a nucleotide sequence having at least 80%, at least 85%, at least 90%, at least 93%, at least 95%, at least 96%, at least 97%, at least 98%, at least 99%, or 100% identity to one or more of SEQ ID NOs:6-15, 39, and 40.

In certain aspects, provided herein are cells (e.g., host cells) expressing (e.g., recombinantly) multispecific antibodies described herein which specifically bind to serum albumin (e.g., human serum albumin) and related polynucleotides and expression vectors. Provided herein are vectors (e.g., expression vectors) comprising polynucleotides comprising nucleotide sequences encoding multispecific antibodies or a fragment for recombinant expression in host cells, such as mammalian cells. Also provided herein are host cells comprising such vectors for recombinantly expressing multispecific antibodies described herein (e.g., human or humanized antibody). Also provided herein are methods for producing an antibody described herein, comprising expressing such antibody in a host cell.

Recombinant expression of an antibody or fragment thereof described herein (e.g., a heavy or light chain of an antibody described herein) that specifically binds to involves construction of an expression vector containing a polynucleotide that encodes the antibody or fragment. Once a polynucleotide encoding an antibody or fragment thereof (e.g., heavy or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., WO86/05807 and WO89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein.

A variety of host-expression vector systems can be utilized to express antibody molecules described. Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some embodiments, cells for expressing antibodies described herein (e.g., an antibody comprising the CDRs of any one of antibodies pab1949 or pab2044) are CHO cells, for example CHO cells from the CHO GS System™ (Lonza). In some embodiments, cells for expressing antibodies described herein are human cells, e.g., human cell lines. In some embodiments, a mammalian expression vector is pOptiVEC™ or pcDNA3.3. In some embodiments, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies described herein are produced by CHO cells or NS0 cells. In some embodiments, the expression of nucleotide sequences encoding antibodies described herein is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81: 3655-3659). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol 153: 516-544).

In addition, a host cell strain can be chosen which modulates the expression of the inserted sequences or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, multispecific antibodies described herein (e.g., an antibody comprising the CDRs are produced in mammalian cells, such as CHO cells.

In some embodiments, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of a1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express multispecific antibodies can be engineered. In specific embodiments, a cell provided herein stably expresses a light chain/light chain variable domain and a heavy chain/heavy chain variable domain which associate to form an antibody described herein (e.g., an antibody comprising the CDRs).

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express a multispecific antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) Cell 11(1): 223-232), hypoxanthineguanine phosphoribosyltransferase (Szybalska E H & Szybalski W (1962) PNAS 48(12): 2026-2034) and adenine phosphoribosyltransferase (Lowy I et al., (1980) Cell 22(3): 817-823) genes can be employed in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-3570; O'Hare K et al., (1981) PNAS 78: 1527-1531); gpt, which confers resistance to mycophenolic acid (Mulligan R C & Berg P (1981) PNAS 78(4): 2072-2076); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-215); and hygro, which confers resistance to hygromycin (Santerre R F et al., (1984) Gene 30(1-3): 147-156). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère- Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

The vector can comprise a first nucleic acid molecule encoding an antigen binding fragment (Fab) that bind to serum albumin, and a second nucleic acid molecule encoding a bioactive effector moiety and a linker.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in some embodiments, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the antibody or fragment is recombinantly produced, it is also generally substantially free of culture medium, i.e., culture medium represents less than about 20%, 10%, 2%, 1%, 0.5%, or 0.1% of the volume of the protein preparation. When the antibody or fragment is produced by chemical synthesis, it is generally substantially free of chemical precursors or other chemicals, i.e., it is separated from chemical precursors or other chemicals which are involved in the synthesis of the protein. Accordingly, such preparations of the antibody or fragment have less than about 30%, 20%, 10%, or 5% (by dry weight) of chemical precursors or compounds other than the antibody or fragment of interest. In some embodiments, antibodies described herein are isolated or purified.

Compositions

Provided herein are compositions comprising a multispecific antibody described herein having the desired degree of purity in a physiologically acceptable carrier, excipient or stabilizer (Remington's Pharmaceutical Sciences (1990) Mack Publishing Co., Easton, PA). Also disclosed herein are pharmaceutical compositions comprising a multispecific antibody described herein and a pharmaceutically acceptable excipient. Acceptable carriers, excipients, or stabilizers are nontoxic to recipients at the dosages and concentrations employed.

The pharmaceutical composition of the present disclosure can provide rapid, sustained or delayed release of an active ingredient after being administered to a subject and can be formulated using a method well known to those skilled in the art. The formulations can be in the form of a tablet, pill, powder, sachet, elixir, suspension, emulsion, solution, syrup, aerosol, soft or hard gelatin capsule, sterile injectable solution, sterile powder, or the like. Examples of suitable carriers, excipients, and diluents are lactose, dextrose, sucrose, sorbitol, mannitol, xylitol, erythritol, maltitol, starches, gum acacia, alginate, gelatin, calcium phosphate, calcium silicate, cellulose, microcrystalline cellulose, polyvinyl pyrrolidone, water, methylhydroxybenzoate, propylhydroxybenzoate, talc, magnesium stearate and mineral oil. Further, the formulations can additionally include a filler, an anti-agglutinating agent, a lubricating agent, a wetting agent, a favoring agent, an emulsifier, a preservative, and the like.

Pharmaceutical compositions described herein can be useful in enhancing, inducing, or activating the activities of multispecific antibodies and treating a disease or condition, such as autoimmune conditions or diseases.

The compositions to be used for in vivo administration can be sterile. This is readily accomplished by filtration through, e.g., sterile filtration membranes.

Uses and Methods

Disclosed herein are methods of treating an autoimmune disease or condition in a subject in need thereof, the method comprising administering the multispecific antibodies or pharmaceutical compositions disclosed herein to the subject. Autoimmune diseases or conditions that can be treated include but are not limited to neuromyelitis optica spectrum disorders, rheumatoid arthritis, multiple sclerosis, Sjögren's syndrome, systemic lupus erythematosus, ANCA-associated vasculitis, ulcerative colitis and Crohn's disease.

In some aspects, presented herein are methods for modulating one or more immune functions or responses in a subject, comprising to a subject in need thereof administering a multispecific antibody described herein, or a composition thereof. Disclosed herein are methods for activating, enhancing or inducing one or more immune functions or responses in a subject, comprising to a subject in need thereof administering a multispecific antibody or a composition thereof. In some embodiments, presented herein are methods for preventing and/or treating diseases in which it is desirable to activate or enhance one or more immune functions or responses, comprising administering to a subject in need thereof a multispecific antibody described herein or a composition thereof. In certain embodiments, presented herein are methods of treating an autoimmune disease or condition comprising administering to a subject in need thereof a multispecific antibody or a composition thereof.

Also disclosed herein are uses of the multispecific antibodies or compositions disclosed herein for the treatment of an autoimmune disease or condition; modulating one or more immune functions or responses; activating, enhancing or inducing one or more immune functions or responses; or preventing and/or treating diseases in which it is desirable to activate or enhance one or more immune functions or responses, in subjects. Also disclosed herein are the multispecific antibodies or compositions disclosed herein for use in the treatment of an autoimmune disease or condition; modulating one or more immune functions or responses; activating, enhancing or inducing one or more immune functions or responses; or preventing and/or treating diseases in which it is desirable to activate or enhance one or more immune functions or responses, in subjects. Also disclosed herein are the use of the multispecific antibodies or compositions disclosed herein for the manufacture of a medicament for treatment of an autoimmune disease or condition; modulating one or more immune functions or responses; activating, enhancing or inducing one or more immune functions or responses; or preventing and/or treating diseases in which it is desirable to activate or enhance one or more immune functions or responses, in subjects.

In some embodiments, a multispecific antibody described herein activates or enhances or induces one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the multispecific antibody described herein using assays well known in the art, e.g., ELISPOT, ELISA, and cell proliferation assays.

Routes of Administration & Dosage

The pharmaceutical compositions of the present disclosure can be administered to a subject through a variety of administration routes including oral, transcutaneous, subcutaneous, intravenous, and intramuscular administration routes.

The amount of an antibody or composition which will be effective in the treatment and/or prevention of a condition will depend on the nature of the disease and can be determined by standard clinical techniques.

In the present disclosure, the amount of the multispecific antibody actually administered is determined in light of various relevant factors including the disease to be treated, a selected route of administration, the age, sex and body weight of a patient, and severity of the disease, and the type of a bioactive polypeptide as an active ingredient. Since the multispecific antibody of the present disclosure has a very excellent sustainability in blood, the number and frequency of administration of the peptide preparations comprising the fusion protein of the present disclosure can be noticeably reduced.

The precise dose to be employed in a composition will also depend on the route of administration, and the seriousness of the disease, and should be decided according to the judgment of the practitioner and each subject's circumstances. For example, effective doses can also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In some embodiments, the dosage of the multispecific antibody disclosed herein is 0.1 mg/kg to 100 mg/kg body weight of the subject, 0.1 mg/kg to 80 mg/kg body weight of the subject, 0.1 mg/kg to 60 mg/kg body weight of the subject, 0.1 mg/kg to 50 mg/kg body weight of the subject, 0.1 mg/kg to 40 mg/kg body weight of the subject, 0.1 mg/kg to 30 mg/kg body weight of the subject, 0.1 mg/kg to 20 mg/kg body weight of the subject, 0.1 mg/kg to 10 mg/kg body weight of the subject, 1 mg/kg to 100 mg/kg body weight of the subject, 1 mg/kg to 80 mg/kg body weight of the subject, 1 mg/kg to 60 mg/kg body weight of the subject, 1 mg/kg to 50 mg/kg body weight of the subject, 1 mg/kg to 40 mg/kg body weight of the subject, 1 mg/kg to 30 mg/kg body weight of the subject, 1 mg/kg to 20 mg/kg body weight of the subject, 1 mg/kg to 10 mg/kg body weight of the subject, 5 mg/kg to 100 mg/kg body weight of the subject, 5 mg/kg to 80 mg/kg body weight of the subject, 5 mg/kg to 60 mg/kg body weight of the subject, 5 mg/kg to 50 mg/kg body weight of the subject, 5 mg/kg to 40 mg/kg body weight of the subject, 5 mg/kg to 30 mg/kg body weight of the subject, 5 mg/kg to 20 mg/kg body weight of the subject, 5 mg/kg to 10 mg/kg body weight of the subject, or any dosages or ranges of dosages encompassed herein, such as 0.1, 0.5, 1, 2, 3, 4, 5, 6, 7, 8, 9, or 10 mg/kg body weight of the subject.

In certain embodiments, an in vitro assay is employed to help identify optimal dosage ranges. Effective doses can be extrapolated from dose response curves derived from in vitro or animal model test systems.

Generally, human antibodies have a longer half-life within the human body than antibodies from other species due to the immune response to the foreign polypeptides. Thus, lower dosages of human antibodies and less frequent administration is often possible Kits Provided herein are kits comprising one or more antibodies described herein or conjugates thereof. In some embodiments, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. Optionally associated with such container(s) can be a notice in the form prescribed by a governmental agency regulating the manufacture, use or sale of pharmaceuticals or biological products, which notice reflects approval by the agency of manufacture, use or sale for human administration. Also provided herein are kits that can be used in the above methods. In some embodiments, a kit comprises an antibody described herein, e.g., a purified antibody, in one or more containers. In some embodiments, kits described herein contain a substantially isolated antigen(s) (e.g., human serum albumin) that can be used as a control. In other embodiments, the kits described herein further comprise a control antibody which does not react with a serum albumin antigen. In other embodiments, kits described herein contain one or more elements for detecting the binding of an antibody to a serum albumin antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized serum albumin antigen. The serum albumin antigen provided in the kit can also be attached to a solid support. In some embodiments, the detecting means of the above described kit includes a solid support to which a serum albumin antigen is attached. Such a kit can also include a non-attached reporter-labeled anti-human antibody or anti-mouse/rat antibody. In binding of the antibody to the serum albumin antigen can be detected by binding of the said reporter-labeled antibody.

Hereinafter, the present disclosure will be described with reference to several embodiments and the accompanying drawings. The following embodiments and drawings are provided for illustration purpose only and not for the purpose of limiting the present disclosure as defined by the appended claims.

EXAMPLES

Example 1. Materials and Methods

1. Gene Cloning 1-1. APB-A1 ((Anti-CD40L scFv)₂-Anti-HSA Fab Structure) Cloning

Gene cloning was conducted using a standard gene recombination method. hu5c8 scFv (SEQ ID NO:5) was synthesized through codon optimization suitable for mammalian cells (Cosmo Genetech, Korea). Primers commercially available from Macrogen (Seoul, Korea) were used for cloning, and initial cloning was conducted on pcDNA3.3 and pOptiVEC vector (Thermo Fisher Scientific) through a polymerase chain reaction (PCR) by linking the synthesized hu5c8 scFv to the N-terminals of SL335 heavy and light chains by means of a flexible linker, respectively. Thereafter, the cloning was identified by protein expression on the ExpiCHO-S™ cell line (Thermo Fisher Scientific, Waltham, Massachusetts). Next, to establish a production cell line from a GS null CHO K1 cell line (Horizon Discovery, Cambridge, UK), cloning was performed using animal cell expressing vectors, that is, pd2535nt (Horizon Discovery) for a heavy chain and pd2539 (Horizon Discovery) for a light chain. The PCR was performed under conditions in which a total of 25 cycles are performed at 95° C. for 30 seconds, at 61° C. for 30 seconds, and at 72° C. for 1 minute, and finally for 5 minutes for extension, followed by lowering the temperature to 4° C. Table 1 indicates primer sets for producing recombinant vectors by cloning the APB-A1 heavy-chain and light-chain genes inserted into pcDNA3.3 and pOptiVEC vectors to pd2535nt and pd2539 vectors, respectively. In addition, pGL3c(1b) (Satorius) plasmid vectors were used as additional vectors.

TABLE 1

| Primer | | | Oligonucleotide sequence |
|---|---|---|---|
| APB-A1 Heavy chain | SEQ ID NO: 16 | | (forward) 5'-gatcaactctagagccaccatg gagtggtcctgggtc-3' |
| | SEQ ID NO: 17 | | (reverse) 5'-aggaagacgcttttagaggcggccgctcagga ggacttgggctccaccttcttatc-3' |
| APB-A1 light chain | SEQ ID NO: 18 | | (forward) 5'-gatcaactctagagccaccatg gagacccacagccag-3' |
| | SEQ ID NO: 19 | | (reverse) 5'-aggaagacgcttttagaggcggccgctcagga ctcccccggttaaagctcttggtcac-3' |

In detail, the PCR was performed in such a manner as described above, and a PCR product of APB-A1 heavy and light chains of about 1,600 base pairs (bp) in length were acquired. Ends of the heavy chain of the PCR product and pd2535nt vector were treated with BbsI (Thermo Fisher Scientific); and 5' ends of the light chain of the PCR product and the pd2539 vector were treated with BsrGI (Thermo Fisher Scientific), 3' ends of the light chain of the PCR product and pd2539 vector were treated with a restriction enzyme BbsI, and then treated with T4 DNA ligase (Takara, Japan). Subsequently, E. coli strain, DH5-alpha (RBC, Canada) was transformed with the produced plasmid by applying heat-shock thereto, and then purified by using a midiprep kit (Macherey Nagel™, Germany) in compliance with the manufacturer's protocol, and eluting with nuclease-free water. The heavy and light chains of APB-A1 were allowed to have amino acid sequences of SEQ ID NO:41 and SEQ ID NO:42, respectively, wherein the 104$^{th}$ amino acid from the N-terminal of those amino acid sequences corresponds to glycine (G) or glutamine (Q).

1-2. APB-B1 ((Anti-CD40L scFv)₂-(Anti-HSA Fab)-(Anti-TNF-α Fv)) Cloning (1) A Fab gene of SL335 binding to human serum albumin, a scFv gene of ruplizumab binding to CD40L and a bioactive-effector gene, were synthesized. The bioactive-effector can be an anti-TNF-α Fv (certolizumab having a heavy chain of SEQ ID NO:6 and a light chain of SEQ ID NO:7) or anti-TNF-α dsFv (certolizumab having a heavy chain of SEQ ID NO:8 and a light chain of SEQ ID NO:9), anti-IL-23 Fv (ustekinumab having a heavy chain of SEQ ID NO:10 and a light chain of SEQ ID NO:11) or anti-IL-23 dsFv (ustekinumab having a heavy chain of SEQ ID NO:12 and a light chain of SEQ ID NO:13), or anti-IFNAR1 Fv (anifrolumab having a heavy chain of SEQ ID NO:14 and a light chain of SEQ ID NO:15) or anti-IFNAR1 dsFv (anifrolumab having a heavy chain of SEQ ID NO:39 and a light chain of SEQ ID NO:40. Tables 2, 3 and 4 provide PCR primer sets for producing the APB-B1 (Macrogen, Korea).

TABLE 2

| Construct | Primer | Oligonucleotide sequence |
|---|---|---|
| (anti-CD40L ScFv)$_2$ + anti-HSA Fab + anti-TNF-α Fv | SEQ ID NO: 20 | (forward) 5'-gatcaactctagagccaccatggagtggtcctgggt-3' |
| | SEQ ID NO: 21 | (reverse) 5'-ggaggacttgggctccaccttcttatcgac-3' |
| | SEQ ID NO: 22 | (forward) 5'-gtcgataagaaggtggagcccaagtcctcc-3' |
| | SEQ ID NO: 23 | (reverse) 5'-atcggcggccgcgaagacgcttttagatca-3' |
| | SEQ ID NO: 24 | (forward) 5'-gatcaactctagagccaccatggagacccacagccag-3' |
| | SEQ ID NO: 25 | (reverse) 5'-ggactcccccggttaaagctcttggtcac-3' |
| | SEQ ID NO: 26 | (forward) 5'-gtgaccaagagctttaaccggggggagtcc-3' |
| | SEQ ID NO: 27 | (reverse) 5'-atcggcggccgcgaagacgcttttagatca-3' |
| (anti-CD40L ScFv)$_2$ + anti-HSA Fab + anti-TNF-α dsFv | SEQ ID NO: 20 | (forward) 5'-gatcaactctagagccaccatggagtggtcctgggt-3' |
| | SEQ ID NO: 28 | (reverse) 5'-tttaccggggggcctgccgaacccagttcat-3' |
| | SEQ ID NO: 29 | (forward) 5'-gccccccggtaaatgtctggaatggatgggg-3' |
| | SEQ ID NO: 30 | (reverse) 5'-atcggcggccgcgaagacgcttttagatca-3' |
| | SEQ ID NO: 24 | (forward) 5'-gatcaactctagagccaccatggagacccacagccag-3' |
| | SEQ ID NO: 31 | (reverse) 5'-ttcatgcggccgcgaagacgcttttagatcaccgcttaatctcaacttttgttccacatccaaatgtcag-3' |

TABLE 3

| Construct | Primer | Oligonucleotide sequence |
|---|---|---|
| (anti-CD40L ScFv)$_2$ + anti-HSA Fab + anti-IL-23 Fv | SEQ ID NO: 20 | (forward) 5'-gatcaactctagagccaccatggagtggtcctgggt-3' |
| | SEQ ID NO: 21 | (reverse) 5'-ggaggacttgggctccaccttcttatcgac-3' |
| | SEQ ID NO: 22 | (forward) 5'-gtcgataagaaggtggagcccaagtcctcc-3' |
| | SEQ ID NO: 23 | (reverse) 5'-atcggcggccgcgaagacgcttttagatca-3' |
| | SEQ ID NO: 24 | (forward) 5'-gatcaactctagagccaccatggagacccacagccag-3' |
| | SEQ ID NO: 25 | (reverse) 5'-ggactcccccggttaaagctcttggtcac-3' |
| | SEQ ID NO: 26 | (forward) 5'-gtgaccaagagctttaaccggggggagtcc-3' |
| | SEQ ID NO: 27 | (reverse) 5'-atcggcggccgcgaagacgcttttagatca-3' |
| (anti-CD40L ScFv)$_2$ + anti-HSA Fab + anti-IL-23 dsFv | SEQ ID NO: 20 | (forward) 5'-gatcaactctagagccaccatggagtggtcctgggt-3' |
| | SEQ ID NO: 32 | (reverse) 5'-ttttccgggcatctgccgtacccacccaag-3' |
| | SEQ ID NO: 33 | (forward) 5'-atgcccggaaaatgtctcgattggataggataatg-3' |
| | SEQ ID NO: 30 | (reverse) 5'-atcggcggccgcgaagacgcttttagatca-3' |
| | SEQ ID NO: 24 | (forward) 5'-gatcaactctagagccaccatggagacccacagccag-3' |
| | SEQ ID NO: 34 | (reverse) 5'-ttcatgcggccgcgaagacgcttttagatcaccgctttatctccaattttgttccacacccgaatgtata-3' |

TABLE 4

| Construct | Primer | Oligonucleotide sequence |
|---|---|---|
| (anti-CD40L ScFv)₂ + anti-HSA Fab + anti-IFNAR1 Fv | SEQ ID NO: 20 | (forward) 5'-gatcaactctagagccaccatggagtggtcctgggt-3' |
| | SEQ ID NO: 21 | (reverse) 5'-ggaggacttgggctccaccttcttatcgac-3' |
| | SEQ ID NO: 22 | (forward) 5'-gtcgataagaaggtggagcccaagtcctcc-3' |
| | SEQ ID NO: 23 | (reverse) 5'-atcggcggccgcgaagacgcttttagatca-3' |
| | SEQ ID NO: 24 | (forward) 5'-gatcaactctagagccaccatggagacccacagccag-3' |
| | SEQ ID NO: 25 | (reverse) 5'-ggactcccccccggttaaagctcttggtcac-3' |
| | SEQ ID NO: 26 | (forward) 5'-gtgaccaagagctttaaccgggggagtcc-3' |
| | SEQ ID NO: 27 | (reverse) 5'-atcggcggccgcgaagacgcttttagatca-3' |
| (anti-CD40L ScFv)₂ + anti-HSA Fab + anti-IFNAR1 DsFv | SEQ ID NO: 20 | (forward) 5'-gatcaactctagagccaccatggagtggtcctgggt-3' |
| | SEQ ID NO: 35 | (reverse) 5'-ttttccgggcatctgccgtacccacccaag-3' |
| | SEQ ID NO: 36 | (forward) 5'-atgcccggaaaatgtctcgattggatagggataatg-3' |
| | SEQ ID NO: 30 | (reverse) 5'-atcggcggccgcgaagacgcttttagatca-3' |
| | SEQ ID NO: 24 | (forward) 5'-gatcaactctagagccaccatggagacccacagccag-3' |
| | SEQ ID NO: 37 | (reverse) 5'-Tacatgcggccgcgaagacgcttttagatcaacgtttaatctcaagtcgagtcccacacccgaaagtaat-3' |

For amplification of the respective scFv, Fab, dsFv and Fv genes, PCR was performed for 30 cycles with a T100™ thermal cycler instrument (Bio-Rad, Hercules, California) using a Taq DNA polymerase (Takara, Japan) under conditions of each cycle being performed at 94° C. for 1 minute, at 60° C. for 1 minute, and at 72° C. for 1 minute. Next, to assemble the respective chain reaction products in a (scFv)₂-Fab-Fv or (scFv)₂-Fab-dsFv format, an assembly PCR was performed under conditions of cycling at 94° C. for 1 minute, at 60° C. for 1 minute, and at 72° C. for 1 minute and 30 seconds. The heavy chain assembled product obtained by the PCR and a pD2535NT vector (Horizon Discovery, United Kingdom) were treated with a Bbs I restriction enzyme (Thermo Fisher Scientific, Waltham, Massachusetts); the light chain assembled product and a pd2539 vector (Horizon Discovery) were treated with Bbs I and Bsr GI restriction enzymes (New England Biolabs, Ipswich, Massachusetts). The chain reaction assembled products treated with the respective restriction enzymes and the plasmid vectors were assembled with each other using a T4 DNA ligase (Takara), and the assembled products were put into soluble competent cells treated with $CaCl_2$, followed by applying heat-shock for transformation. Next, the transformed clones were screened using a culture medium containing a Kanamycin antibiotic.

In addition, to produce recombinant human CD40L (rhCD40L-his), cloning assays were conducted in the same manner as described above. The recombinant human CD40L gene (SEQ ID NO:38) synthesized by Cosmo Genetech was used and cloned to pcDNA3.3™® vector (Thermo Fisher Scientific) using restriction enzymes Xba I (Takara) and Not I (Takara).

(2) Proteins were produced by transient expression using a CHO cell. For production of a SAFA-based bispecific antibody and a recombinant human CD40L protein sample, an ExpiCHO cell (Thermo Fisher Scientific) was incubated in a shaking incubator under conditions of 37° C., 140 rpm, 5% $CO_2$, and 80% humidity with ExpiCHO expression media (Thermo Fisher Scientific). For production of transient expression cells, the cells were seeded to a 125 m$\ell$-culture flask under the condition of a concentration of $6.0 \times 10^6$ cells/m$\ell$, and plasmid vectors pD2535NT and pD2539, having 3 sequence-identified genes (certolizumab, ustekinumab and anifrolumab) heavy and light chains inserted thereto, and a recombinant human CD40L gene inserted vector pcDNA3.3-TOP® were transfected to the seeded cells using an ExpiFectamine CHO transfection kit (Thermo Fisher Scientific). The cells incubated in the shaking incubator for 16 hours were treated with ExpiCHO feed and an enhancer, followed by incubating for 3 days in the incubator being under the same conditions. On day 3 of incubation, ExpiCHO feed was additionally treated and incubated under conditions of 32° C., 140 rpm, 5% $CO_2$, and not less than 80% humidity. On day 9 of incubation, the culture medium was collected and then centrifuged under conditions of 4,000 rpm, 15 minutes, and 4° C., thereby isolating cells from the culture medium. The isolated culture medium was filtered through a 0.2 μm-filter sheet, thereby removing impurities.

2. Production of Cell Line 2-1. GS Null CHO K1 Cell Line for APB-A1

A glutamine synthesis (GS)-null CHO K1 cell line (Horizon Discovery) was used. CDfortiCHO (Thermo Fisher Scientific) medium supplemented with 4 mM L-glutamine (Gibco, Thermo Fisher Scientific) was used, and the culture medium was incubated in a shaking incubator at 125 rpm under conditions of 80% humidity, 5% $CO_2$ and 37° C. Transfection was performed using a Freestyle™Max reagent (Invitrogen, Thermo Fisher Scientific) according to the procedure modified from the standard protocol provided by Horizon Discovery. The transfection was performed by co-transfecting light chains and heavy chains in a ratio of 1:1 to 1:3 (pd2539: pd2535nt) using a total of 37.6 µg plasmid vectors. 2 days after transfection, the incubated cells were taken out, transferred to a 50 mℓ conical tube (Nunc, Denmark) for centrifugation, and then dissolved in a CDfortiCHO culture medium not containing L-glutamine, followed by identifying the cell concentration and viability using a COUNTESS II automated cell counter (Invitrogen, Thermo Fisher Scientific). 50 µM methionine sulfoximine (MSX) (Sigma-Aldrich, St. Louis, Missouri) was added, and partial selection was made. Thereafter, after another 2 days, 10 µg/mℓ puromycin (Gibco) was added to MSX-added cells, followed by incubation for 48 hours. Next, the incubated cells were dissolved with a culture medium not containing L-glutamine so as to have a precipitated cell concentration of $0.5 \times 10^6$ cells/mℓ, and MSX and puromycin were then added together for total selection. Then, the cell concentration was maintained so as not to exceed $2.0 \times 10^6$ cells/mℓ, incubation was performed until the cell viability reached 90% or greater, thereby producing a cell line.

2-2. GS Null CHO-K1 Cell Line for APB-B1

HD-BIOP3 GS-null CHO-K1 cell (Horizon Discovery) seeded to a CD FortiCHO (Thermo Fisher Scientific) culture medium supplemented with 4 mM L-glutamine was prepared under the condition of a concentration $3.0 \times 10^5$ cells/mℓ, and seed culture was performed in a shaking incubator being under conditions of 37° C., 5% $CO_2$, and not less than 80% humidity, for 1 day. For transfection, cells were seeded at a concentration of $4.8 \times 10^5$ cells/mℓ, additionally incubated for 1 day, and finally prepared at a concentration of $1.0 \times 10^6$ cells/mℓ. Plasmid vectors (pD2535NT and pD2539) containing heavy and light chain genes of a sequence-identified, certolizumab-related SAFA-based bispecific antibody were transfected to the seeded cells using OptiPRO SFM culture media and a Freestyle max reagent (Invitrogen, Carlsbad, California), and then incubated for 2 days under conditions of 37° C., 5% $CO_2$, and not less than 80% humidity. The incubated cells were all transferred to a CD FortiCHO culture medium not containing L-glutamine and then treated with 50 µm of methionine sulfoximine (MSX) (Sigma-Aldrich, St. Louis, Missouri) and 10 µg/mℓ puromycin (Thermo Fisher Scientific) at 2 day intervals, thereby removing the cells not containing a vector. Then, the pre-existing culture medium was removed using a centrifuge and then replaced by a CD FortiCHO culture medium containing both MSX and puromycin at an interval of 7 to 10 days, and incubation was performed for 21 days so as to maintain the number of cells to be $5.0 \times 10^5$ cells/mℓ. After 21 days, when the cell viability became 70% or greater, culture was performed so as to maintain the number of cells to be $3.0 \times 10^5$ cells/mℓ, and subculture production was started when the cell viability was 90% or higher, yielding a subculture 0 (zero) stock, and continued until a stock 3 was produced.

3. Isolation, Purification and Analysis of Protein 3-1. APB-A1 Protein (1) ELISA rhCD40L, a recombinant hCD40L antigen prepared according to the present disclosure (AprilBio, Chuncheon, South Korea) was coated onto a 96-well MaxiSorp ELISA plate (Nunc) at a concentration of 100 ng/well overnight at 4° C. using a carbonate coating buffer (pH of 9.6). The plate was blocked by treating with a blocking buffer (Starting Block™ (PBS) (Thermo Fisher Scientific) at room temperature for 3 hours. After washing with a wash buffer (phosphate buffered saline+0.1% tween 20; 0.1% PB ST), the supernatant of the recombinant antibody having a structure of anti-CD40L scFv)$_2$-anti-HSA Fab produced from GS null CHOK1 cell, termed APB-A1, was continuously diluted with a dilute buffer (0.1% PBST+0.3% BSA; 0.3% PBA), and was allowed to react at room temperature for 1 hour. A horseradish peroxidase (HRP) conjugated goat-anti-human Fd antibody (Southern Biotechnology, Birmingham, Alabama) was used as a secondary antibody, and a tetramethylbenzidine (TMB) substrate (BD science, Franklin Lakes, New Jersey) was used for luminescence. Absorbance was measured at 450 nm using an ELISA reader (BMG Labtech, Germany). PK ELISA was performed such that the rhCD40L antigen was diluted in PBS (Roman Industries, Japan) at a concentration of 1 µg/mmℓ and then coated on an ELISA plate at a volume of 100 µℓ overnight at 4° C. On the next day, a blocking buffer (0.3% BSA in PBS, 300 µℓ) was added to each well to perform blocking at 25° C. for 3 hours, and standard and QC samples were transferred to each well at a volume of 100 µℓ and were allowed to react at 25° C. for 1.5 hours. After washing 3 times with a wash buffer (300 µℓ/well), the anti-human light chain goat IgG-biotin (monkey absorbed; Immuno-Biological Laboratories, Japan) was seeded to each well at a 100 µℓ/well concentration and were allowed to react at 25° C. for 1 hour. Subsequently, after washing 4 times, Pierce high sensitivity streptavidin-HRP (Thermo Fisher Scientific) was reacted under the same volume and time conditions and then washed. Next, a 1-step ultra TMB-ELISA substrate solution (Thermo Fisher Scientific) was transferred to each well at a volume of 100 µℓ and reacted at room temperature for 5 minutes. Successively, 1 mol/L sulfuric acid (Wako Pure Chemical, Japan; 100 µℓ/well) was added as a stop solution, followed by mixing using a microplate mixer at 600 rpm for 10 seconds, and measuring absorbance at 450 to 650 nm.

(2) Protein Purification

The GS null CHO K1 cell line expressing the produced APB-A1 was incubated in a CDfortiCHO culture medium using a WAVE bioreactor (GE Healthcare) for 11 days, the resulting supernatant and cell pellets were centrifuged at 4° C. at 4,000 rpm for 20 minutes, and the culture supernatant was filtered with a 0.2 µm filter. APB-A1 protein was purified through a 3-step chromatography process. First, an affinity chromatography step was performed using a CaptureSelect IgG-$C_{H1}$ affinity matrix resin (Life Technologies). After washing a matrix with PBS of 5 column volumes (CVs), sample binding was performed at a flow rate of 20 mℓ/min. In order to eliminate proteins other than a target protein, a washing step was performed using 4 CVs of a high-salt wash buffer (PBS, 500 mM NaCl, pH 7.4) and 2 CVs of a low-salt wash buffer (25 mM sodium phosphate, pH 7.6) at a flow rate of 25 mℓ/min. An elution buffer (20 mM citric acid pH 3.0, 150 mM sodium chloride) was passed through the matrix at a flow rate of 20 mf/min, and a protein solution having peaks of UV 50 mAU or greater was collected and then transferred to a 250 mℓ container for cold storage for 1 hour. The collected protein solution was neutralized by adding a 1 M tris-HCl (pH 8.0) solution, and impurities were removed using a 0.2 µm filter, thereby eluting the APB-A1. Next, cation exchange purification was performed using a Capto™ SP ImpRes resin equilibriated by 25 mM of a sodium phosphate (pH 7.6) solution. An affinity chromatography elution sample which was 4× diluted with sterilized distilled water was coupled to a column with a flow rate set to 5 mf/min, and 30%-50%-100% elution steps were performed using an elution buffer (25 mM sodium phosphate, pH 7.6, 1 M sodium chloride). The eluate of each step was collected, and impurities were removed therefrom using a 0.2 µm filter. Successively, anion exchange purification was performed using a POROS-based anion exchange 50 HQ resin. First, a wash buffer (2 M sodium chloride) was passed through at a flow rate of 3 mℓ/min to wash a resin column, 5 CVs of 20 mM sodium phosphate (pH 6.5) solution was passed through the resin column for equilibration. To bind impurities to the resin, a sample was dialyzed with 20 mM of a sodium phosphate pH 6.5 buffer, and the pH level and salt concentration were adjusted. The sample was passed through the resin column at a flow rate of 5 mℓ/min to collect a protein solution, followed by removing impurities using a 0.2 µm filter, and the obtained protein was quantified and analyzed.

(3) Protein Analysis—SDS-PAGE

The purified APB-A1 protein was analyzed through SDS-PAGE. Sample buffer solutions used for analysis were an LDS nonreducing sample buffer (4×; Thermo Fisher Scientific) and a reducing sample buffer (4×) prepared by adding 5% mercaptoethanol to the nonreducing sample buffer, and the respective sample buffer solutions were mixed with samples and placed in a water bath and boiled for 5 minutes, then be analyzed under nonreducing-boiled and reducing conditions. In addition, the nonreducing sample buffer (4×) and the sample were mixed in a ratio of 1:4, and analysis was performed under a not-boiled condition with heat treatment skipped. The protein sample was loaded onto a 4 to 15% gradient gel (Bio-Rad, Hercules, California) at a concentration of 1 µg/well, and then electrophoresed at 150 V for 50 minutes, thereby performing SDS-PAGE analysis. The gel separated after the electrophoresis was stained with an Ez-Gel stain solution (DoGenBio, South Korea) for 1 hour, and then decolorized with water.

(4) Protein Analysis—High-Performance Liquid Chromatography (HPLC)

To assess the size and purity of the purified protein, SE-HPLC (size exclusion high-performance liquid chromatography) was performed using prominence HPLC (Shimadzu, Japan) and a TSK gel Ultra SW aggregate column (Tosoh Bioscience, Japan). The sample was diluted with 100 mM $Na_2HPO_4$, 100 mM $Na_2SO_4$, and 0.05% (w/v) $NaN_3$ (pH 6.7), and 50 µg of the diluted sample was injected by an automatic sample injector at 15° C., and then eluted using a mobile phase (200 mM phosphate, pH 6.7, 0.05% (w/v) $NaN_3$ (flow rate: 0.5 mℓ/min). The UV absorbance was measured at a wavelength of 280 nm.

(5) Protein Analysis—Mass Spectrometry

Molecular weights of reduced and nonreduced APB-A1 were measured using LC-ESI MS spectrometry, and then analyzed in combination with Dionex UHPLC (Thermo Fisher Scientific) and Q-TOF 5600+MS/MS system (AB SCIEX, CA, USA). An Acquity UPLC® BEH1 30 C4, 1.7 µm column was used, and a mobile phase [acetonitrile (ACN; J. T. Baker)] was passed through the column at a flow rate of 300 µℓ/min to measuring masses of the heavy (H) and light (L) chains of APB-A1.

(6) Protein Analysis—Isoelectric Focusing (IEF)

(4) To assess an isoelectric point of the purified protein, the pI value of the isolated protein was measured using an isoelectric focusing gel (pH 3 to 10). After loading 1 µg, 3 µg, and 5 µg of the sample onto the gel at a density of 1 mg/mℓ, isoelectric focusing was performed at 100 V for 1 hour, at 200 V for 1 hour, and at 500 V for 2 hours, and 12% trichloroacetic acid (TCA) staining and coomassie brilliant blue (CBB) staining were performed, followed by analyzing by ImageMaster™ 2D Platinum (GE healthcare, ver 5.0).

(7) Protein Analysis—Charge Variant Analysis

To analyze a charge variant of APB-A1, ion change chromatography was performed using Protein-Pak HiRes CM. 20 µg of the protein sample was injected by an automatic sample injector at 30° C., and then eluted using a mobile phase [25 mM 2-(Nmorpholino) ethanesulfonic (MES), 500 nM NaCl, pH 6.5] with a gradient of 0 to 40% for 30 minutes. The flow rate was 0.3 mℓ/min, and the UV absorbance was measured at a wavelength of 280 nm.

3-2. APB-B1 Protein (1) Isolation and Purification

For purification of a bispecific antibody protein sample present in a CHO cell culture medium, affinity chromatography (AC) was performed using a CaptureSelect IgG-$C_{H1}$ affinity matrix resin (Life Technologies, Carlsbad, California) and an AKTA pure 150 L instrument (GE Healthcare, Chicago, Illinois) in the following manner. A phosphate-buffered saline (PBS) (pH 7.4) buffer was passed through a resin-packed column for equilibration, a culture medium containing a protein expressed from a transient expression cell was isolated and then passed through the resin column at a flow rate of 1.5 mℓ/min. Thereafter, the PBS pH 7.4 buffer containing 500 mM NaCl was passed through the column to wash materials non-specifically binding to the resin. The equilibration and washing steps for each material were performed with 10 column volumes (CVs). To elute the SAFA-based bispecific antibody from the resin, a 20 mM citric acid, pH 3.0 buffer containing 150 mM NaCl was used. The eluted buffer was treated with 1 M Tris-HCl (pH 8.0) to be neutralized to have a neutral pH level, and the concentration of the purified protein was measured using a microplate spectrophotometer (BMG LABTECH, Germany) at a wavelength of A280 nm. For purification of the bispecific antibody protein sample, following the affinity chromatography, anion exchange chromatography (AEX) was performed using a Q sepharose HP resin (GE Healthcare) in the following manner. After equilibrating about 10 CVs of a 20 mM citrate, pH 6.0 buffer without NaCl added thereto was passed through a Q sepharose HP resin, the protein primarily purified through affinity chromatography was passed through the resin, and then the protein not binding to the resin was recovered. The concentration of the recovered protein was measured using a microplate spectrophotometer instrument at a wavelength of A280 nm. To isolate a protein corresponding to a dimer size of $(scFv)_2$-Fab-dsFv, that is, a SAFA-based bispecific antibody containing disulfide bond, and a protein corresponding to a monomer size (intact form), cation exchange chromatography (CEX) was performed by packing a CM sepharose FF resin (GE Healthcare) into a column. Prior to purification, a pre-treatment step was performed by dialyzing the protein purified by affinity chromatography with a 20 mM citric acid, pH 6.0 binding buffer without NaCl added thereto. About 10 CVs of the binding buffer was passed through the resin-packed column at a flow rate of 1.0 mℓ/min for equilibration, and a pre-treated protein was then treated at the same flow rate and was allowed to react with the resin. Next, 5 CVs of the binding buffer was passed through the column at the same flow rate, and 3 CVs of 100 mM NaCl added binding buffer was further treated, thereby washing and removing nonspecifically binding materials. Next, the bispecific antibody protein existing in the form of monomer was eluted from the resin by adding 120 mM of a NaCl added binding buffer. The concentration of the purified protein was measured at A280 nm. For purification of the recombinant human CD40L protein sample, Profinity™ IMAC (Bio-Rad), Hitrap Q HP, 5 mℓ, (GE Healthcare), Hitrap SP HP, 5 mℓ (GE Healthcare) resin and an AKTA pure 150 L instrument were used in performing 3-step chromatography. First, 20 mM of a sodium phosphate pH 7.2 buffer was used in equilibrating and washing three resins. For elution of the protein sample, 20 mM of a sodium phosphate pH 7.2 buffer containing 500 mM imidazole (Sigma) was used in affinity chromatography. The protein sample was purified using 15 mM of a sodium phosphate, pH 7.4 buffer containing 1 M NaCl in anion chromatography and cation chromatography. The concentration of the purified protein was measured using a microplate spectrophotometer at A280 nm.

(2) SDS-PAGE Analysis

First, the purified bispecific antibody protein sample was diluted with a nonreducing 4×SDS sample buffer (Thermo Fisher Scientific) and a reducing sample buffer containing 2-mercaptoethanol. In the case of the nonreducing condition, to compare the protein types and sizes depending on heat treatment, a sample heated at 100° C. for 5 minutes and an unheated sample were prepared, and for size comparison, a protein size marker (SMOBio, Taiwan) and a (scFv)$_2$-Fab protein sample were treated together. The prepared protein samples were loaded onto a 4-15% 15-well Miniprotein TGX precast gel (Bio-Rad) at a density of 2 µg/well, and electrophoresis was performed in a tris-glycine SDS running buffer at 150 V for 1 hour. After completion of the electrophoresis, the SDS-PAGE gel was stained with an EZ-Gel staining solution (DoGenBio, South Korea) for 1 hour, and decolorized in distilled water for one day.

(3) Protein Melting Temperature Analysis

To assess the thermal stability of a bispecific antibody protein sample, the protein melting temperature was analyzed using a hydrophobic dye (5,000×, SYPRO Orange) and Light Cycler 480 II (Roche, Switzerland) as a real time PCR instrument. The protein sample was diluted in a sodium phosphate pH 7.0 buffer at a 300 µg/mℓ concentration, and then placed in an ultraAmp PCR plate (Sorenson Bioscience, Salt Lake City, Utah) with a 5× reagent and a SYPRO Orange dye until the final concentration of each well reached 5.4 µg/well. Next, an excitation filter and an emission filter were set to 465 nm and 580 nm, respectively, and the denaturation of protein was assessed according to the temperature increasing at a rate of 1° C./min within a range from 20° C. to 85° C.

(4) Size Exclusion High-Performance Liquid Chromatography (SE-HPLC)

The purity of the purified bispecific antibody was analyzed using a column T SKgel UltraSW Aggregate 7.8×300 mm (Tosoh Bioscience, Japan) and a 1260 infinity II LC system (Agilent Technologies, Santa Clara, California) as a HPLC instrument. Prior to sample analysis, the column and the HPLC instrument were equilibrated with 100 mM of a 20 mM citric acid (pH 5.5) buffer. The sample to be analyzed was diluted with 20 mM citric acid pH 5.5 buffer, and the sample was loaded onto the column at a density of up to 25 µg. SE-HPLC analysis was performed under conditions of 0.7 mℓ/min in the flow rate and 120 bar in the maximum pressure limit for 30 minutes, and the absorbance was measured at A280 nm.

(5) Enzyme-Linked Immunosorbent Assay (ELISA)

To assess binding reactions of the purified bispecific antibody sample for human serum albumin (Sigma-Aldrich), a recombinant human CD40L protein, and a recombinant human TNF-α protein (BioLegend, San Diego, California), ELISA was performed. Human serum albumin, CD40L and TNF-α protein were diluted in sodium carbonate pH 9.6 buffer at a 1 µg/mℓ concentration, and each 100 µℓ was then seeded to each well of a 96-well maxisorp plate (Nunc, Denmark), followed by coating at 4° C. for one day. The non-coated protein and the buffer were completely removed, and blocking was then performed by adding each 300 µℓ of a PBS pH 7.4 buffer containing 3% bovine serum albumin (BSA) (Sigma-Aldrich) and 0.1% tween-20 to each well. After blocking for 2 hours, washing was performed by repeatedly performing a process of completely removing the added buffer, adding each 300 µℓ of a buffer (PBS-T) containing 0.1% tween-20 PBS (pH 7.4), and then removing the buffer 3 times in total. After removing water remaining after the washing, the respective antibodies were serially diluted 10 folds at concentrations decreasing from 100 nM to $1.0 \times 10^{-4}$ nM in a PBS pH 7.4 buffer (0.3% PBA) containing 0.3% bovine serum albumin and 0.1% tween-20, and each 100 µℓ of the diluted antibody samples were added to each well to be allowed to react at room temperature for 2 hours. After washing in the same manner as described above, HRP-conjugated goat anti-human Fd antibodies (Southern Biotechnology, Birmingham, Alabama) were diluted with a 0.3% PBA buffer in 1:4,000, and each 100 µℓ of the diluted antibody samples were added to each well to then be allowed to react at room temperature for 1 hour. To assess antigen-specific binding of the antibodies reacting after the washing, a TMB substrate (BD Bioscience, Franklin Lakes, New Jersey) was added and reacted, and the absorbance was measured using a microplate spectrophotometer at A450 nm.

(6) Bio-Layer Interferometry (BLI) Assay

Antigen affinities of a bispecific antibody and an individual single specific antibody to human serum albumin, CD40L and TNF-α were assessed by biolayer interferometry (BLI) using an Octet Red instrument (Forte Bio, Fremont, California). First, TNF-α protein (30 µg/mℓ), CD40L protein (10 µg/mℓ) and human serum albumin (20 µg/mℓ) were immobilized to an amine reactive second generation (AR2G) biosensor (Forte Bio) using a pH 5.0 sodium acetate buffer, materials that are not immobilized were removed with 1 M ethanolamine (pH 8.5), and the bispecific antibody was allowed to react at serially diluted concentrations, followed by measuring binding and dissociation constants for the respective antigens. In addition, to assess simultaneous binding capacities of the bispecific antibody to the three antigens, CD40L protein (10 µg/mℓ) was immobilized to the AR2G biosensor using the pH 5.0 sodium acetate buffer, and binding capacities were measured in the order of the bispecific antibody (3.2 µg/d), human serum albumin (13.2 µg/mℓ), human serum albumin (13.2 µg/mℓ) and TNF-α (2 µg/mℓ). The assessment results were analyzed using DataAnalysis8 software.

(7) Flow Cytometry Analysis

To identify binding of a bispecific antibody and a cellular membrane CD40L, flow cytometry analysis was performed using a FACSVerse instrument (BD Biosciences, Franklin Lakes, NJ). D1.1 cells (CRL-10915, ATCC, Manassas, Virginia) expressing cellular membrane CD40L on cell surfaces were incubated in RPMI1640 (Thermo Fisher Scientific) containing 10% fetal bovine serum (Thermo Fisher Scientific) to prepare $3.0 \times 10^5$ cells/tube and washed twice with a 0.3% PBA buffer. A SAFA-based bispecific antibody and control antibody were allowed to react with the washed cells at 4° C. for 30 minutes, respectively and washed twice, and fluorescein isothiocyanate (FITC)-conjugated goat anti-human kappa antibody (LifeSpan BioSciences, Inc., Seattle, Washington) diluted in 1:1,000 was then added thereto, followed by reacting at 4° C. for 30 minutes. Next, washing steps were repeated twice, and the binding reaction of the antibody to the cellular membrane CD40L was assessed using the FACSVerse instrument.

Example 2: APB-A1

1-1: Binding Assay Using Biolayer Interferometry

Real-time binding assays between human serum albumin (HSA) (Sigma-Aldrich) and SL335 and between rhCD40L antigen and APB-A1 were performed using biolayer interferometry equipped with an Octet RED system. To assess the HSA binding affinity, 20 µg/m$\ell$ of HSA and 10 µg/m$\ell$ of rhCD40L were immobilized to the AR2G biosensor (pH 5.0), non-binding molecules were removed from the surface of the biosensor using a kinetics buffer (1 M ethanol amine, pH 8.5). To identify the affinities of APB-A1 binding to HSA and rhCD40L, the experiments were carried out at concentrations ranging from 10 nM to 0.3125 nM. To identify bispecific binding, the rhCD40L antigen was immobilized to the AR2G biosensor, and APB-A1 was primarily reacted at the determined concentration to then bind to HSA. The binding and dissociation kinetics were obtained using Octet QK software. Binding rate constants were calculated such that the observed binding curves are fitted to a 1:1 binding model.

1-2: Determination of Binding or Non-Binding of APB-A1 Protein and CD40L Expression Cell To confirm that the APB-A1 protein binds to a D1.1 cell expressing a CD40L cell, flow cytometry was performed by College of Pharmacy, Kangwon National University. D1.1 cells were centrifuged to remove a supernatant and then resuspended in a MACS buffer (0.5% BSA, 2 mM EDTA in 1×PBS, 0.22 fall filtered) at a concentration of $1.0 \times 10^6$ cells/m$\ell$. After the cells were seeded at each concentration of 100 µ$\ell$ (1.0 $10^5$ cells/test) to a 1.5 me tube, centrifugation was performed for 5 minutes under 4° C., and 500× g conditions, thereby removing the supernatant. APB-A1, hu5c8 IgG1 and SL335 were continuously diluted by one tenth (1/10) at 5 time points each starting from at an amount of 1 µg/m$\ell$, and each 100 µ$\ell$ of the first diluted antibodies were transferred to cell pellets of 1.5 m$\ell$ tubes using a pipette, followed by incubating at 4° C. for 30 minutes. The MACS buffer was added by each 500 µ$\ell$ to the respective tubes, and then washed by centrifuging under conditions of 4° C., 500× g, and 5 minutes. After removing the supernatant, cell pellets were dissolved by adding each 50 µ$\ell$ of the goat-anti-human kappa-FITC samples diluted in 1:1000 to the MACS buffer (Lifespan Biosciences, Washington, Seattle), followed by incubating at 4° C. for 30 minutes, and the washing step was repeated once again. After removing the supernatant, the cell pellets were dissolved by adding 200 µ$\ell$ of 0.4% paraformaldehyde (PFA in PBS) buffer, followed by storage at 4° C. for immobilization, and the cells were analyzed by a BD FACS verse instrument.

1-3: In vitro CD40-CD40L Inhibition Analysis

To analyze CD40-CD40L interaction inhibitory potency of APB-A1, HEKBlue™ CD40L reporter cells (InvivoGen, San Diego, California) were used, and D1.1 cells expressing mCD40L, and rhCD40L, were used as CD40L donors. Buffers with and without 20 M HSA added to a Dulbecco's PBS buffer (Corning) containing 0.2% bovine serum albumin were used, and APB-A1, hu5c8 IgG1 and SL335 were diluted by one third (1/3) starting from a concentration of 200 nM. After seeding the diluted sample by each 20 µ$\ell$ to a 96-well cell culture plate (Corning), the D1.1 cells were added by an equal volume of $1 \times 10^4$ cells/well, and incubated in an incubator being under conditions of 37° C. and 5% $CO_2$, for 3 hours. Next, HEKBlue™ CD40L cells were added at a density of $5 \times 10^4$ cells per well, and then incubated in an incubator being under the same condition for 21 hours. After 24 hours, the supernatant was transferred by each 40 µ$\ell$ from the plate to other 96-well EIA/RIA plates (Corning) using a multi-pipette. Each 160 µ$\ell$ of a QUANTI-Blue™ solution (InvivoGen) was added to each well, which was wrapped with a foil to block light, and was kept in a 37° C. $CO_2$ incubator for 1 hour, followed by measuring the absorbance at 655 nm using a spectrophotometer. Each 70 µ$\ell$ of 300 ng/m$\ell$ rhCD40L antigen was added to a tube containing 70 µ$\ell$ of a diluted sample obtained by diluting the three samples by one third (1/3) at the same concentration starting from 200 nM, and was then allowed to react at 37° C. in a $CO_2$ incubator for 30 minutes. Next, after diluting HEKBlue™ CD40L cells until the final concentration became $3.125 \times 10^5$ cells/m$\ell$, 560 µ$\ell$ of the diluted cells were added to a tube containing the sample mixed with the rhCD40L antigen, followed by inverting, and the cells were then plated to a 96-well cell culture plate at a concentration of 200 µ$\ell$/well. Incubation was performed in the same manner as in the D1.1 cells for 21 hours, and the resulting cells were allowed to react with a substrate, thereby assessing the absorbance.

1-4: Platelet Aggregation Assay

Human platelet-rich-plasma (PRP) was obtained from a normal healthy volunteer after prior consent and was supplied from the Korean Red Cross Blood Centers (KRBC) (Republic of Korea). PRP anticoagulated in an acid-citrate dextrose solution (0.8% citric acid, 2.2% sodium citrate, 2.45% glucose) was centrifuged at 120×g for 10 minutes to eliminate red blood cells, and then centrifuged at 360×g for 15 minutes to obtain plate pellets. Platelets were dissolved in platelet poor plasma (PPP) at a final concentration of $5.0 \times 10^8$/m$\ell$, and all procedures were performed at room temperature (23±2° C.). To evaluate platelet aggregation, light-transmission aggregometry was performed using a Chrono-log aggregometer (CHRONO-LOG®, Havertown, Pennsylvania). The PRP was stimulated under a continuous stirring condition at a sub-optimal concentration of ADP (CHRONO-LOG®) for 5 minutes after placing an immune complex (IC), that is, rhCD40L+hu5c8 IgG1 (30 µg/m$\ell$ +60 ng/m$\ell$), rhCD40L+APB-A1 (30 µg/m$\ell$ +40 ng/m$\ell$), or each of rhCD40L, hu5c8 IgG1 and APB-A1, in 5 to 10 mM CaCl2 at 37° C. for 2 minutes. After completion of the aggregation reaction, the platelet mixture was centrifuged, the release of serotonin was measured from the supernatant using a serotonin EIA kit (Labor Diagnostikallord, Germany) as per manufacturer's instructions.

1-5: Pharmacokinetic (PK) Analysis and Pharmacodynamics (PD) Analysis (1) PK Analysis To assess the serum half-life of APB-A1, pharmacokinetic analysis was performed on cynomolgus monkey models [Shin Nippon Biomedical Laboratories (SNBL, Japan)]. APB-A1 proteins were administered to each 3 cynomolgus monkeys (males) of each group at a dose of 5 mg/kg (group 1) or 20 mg/kg (group 2) through a single intravenous injection. After the administration, blood samples were collected from a total of 17 points in time: 1 point prior to administration; and 16 points; 0.25, 1, 2, 6 and 24 hours and 4, 7, 10, 13, 16, 19, 22, 25, 28, 34 and 40 days after administration. The concentration of APB-A1 present in the platelet of each cynomolgus monkey was measured by ELISA.

(2) PD Analysis

The anti-tetanus-toxoid (TT) antibody response suppressing efficacy of APB-A1 was analyzed (Southern Research, Birmingham, Alabama). A total 4 groups of samples of a vehicle (negative control group: 20 mmol/L sodium phosphate, pH 6.5), dexamethasone (DXT) (positive control group), and APB-A1 (5 mg/kg and 20 mg/kg) were intravenously administered to cynomolgus monkeys (females; n=3/group). First, for induction of anti-TT antibody responses, TT (5 Lf) was firstly intramuscularly administered on day 1 and was secondly intramuscularly administered on day 20 for boosting. DXT was injected a total of 4 times at each dose of 1 mg/kg, that is, 2 days before the first TT injection and on days 1, 5 and 8 after the first TT injection, and APB-A1 was injected once at the time of the first TT injection (on day 1). The blood samples to be analyzed were collected prior to injection, on days 10, 12, 14, 16, 20, 27, 30 and 40, and anti-TT IgG antibody values were measured by ELISA. For analysis of second antibody responses, a variety of B cell immunophenotypes through immunophenotyping. The blood samples were collected a total of 5 times about 2 hours after TT injection, and on days 20, 27, 30 and 40 after TT injection, and the collected blood samples were stored in K2-EDTA containing tubes to prevent blood coagulation from non-injected portions. Immunophenotyping was performed using antibody panels for markers such as CD45, CD20, CD27, Ki67 and IgD, and predetermined portions of four cell groups including CD45+/20+, CD45+/20+/Ki67+, CD45+/20−/27hi/IgD−, and CD45+20+/27+IgD−/Ki67+, were used for immunophenotyping.

Example 3: APB-B1

1-1: Test of Effect of Inhibiting TNF-α Mediated Cytotoxicity Using Mouse L929 Cells For comparison of soluble TNF-α protein inhibiting capacities of a bispecific antibody and a parental antibody (certolizumab Fab'), a L929 mouse cell expressing a TNF receptor on a cell surface and a recombinant soluble TNF-α protein were used. L929 cells (Korean Cell Line Bank) were incubated with an RPMI1640 culture medium containing 10% fetal bovine serum in an incubator being under conditions of 37° C., 5% $CO_2$, and not less than 80% humidity. L929 cells were plated to a 96-well cell culture plate (Corning Inc., New York City, New York) under the condition of a concentration of $5.0\times10^4$ cells/well, and then incubated in an incubator being under the same condition for 24 hours. After 24 hours of incubation, the existing culture medium was removed, actinomycin D (Sigma-Aldrich) diluted with an RPMI1640 culture medium containing 10% fetal bovine serum at a 1 μg/mℓ concentration was treated on each well, and then reacted for 30 minutes in an incubator being under conditions of 37° C., 5% $CO_2$, and not less than 80% humidity. Next, the antibodies serially diluted according to varying concentrations were treated on each well, and recombinant soluble TNF-α proteins were then treated at a 10 ng/mℓ concentration to then be allowed to react for 24 hours in an incubator being under conditions of 37° C., 5% $CO_2$, and not less than 80% humidity. After 24 hours of reaction, 10 μℓ of CCK-8 (Dojindo, Japan) was treated by transferring the same using a multi-channel pipette to the wells containing the respective reactants. After 2 hours of reaction, the supernatant was transferred to another plate using a pipette, and the absorbance was measured at A450 nm wavelength.

1-2: Inhibition of CD40L and TNF-α Using CD40L HEK-Blue™ Reporter Cells

The simultaneously inhibiting capacities of a bispecific antibody and parental antibodies (ruplizumab IgG1 and certolizumab Fab') for either or both of a cellular membrane CD40L and a soluble TNF-α protein, were analyzed. To this end, the analysis was performed using a CD40L HEK-Blue™ reporter cell (InvivoGen, San Diego, California) expressing secreted embryonic alkaline phosphatase (SEAP) by reacting with CD40L and TNF-α, D1.1 cells expressing cellular membrane CD40L on cell surfaces, and recombinant soluble TNF-α proteins. The CD40L HEK-Blue™ cells were incubated with a DMEM (Thermo Fisher Scientific) culture medium containing 10% fetal bovine serum and an antibiotic (Normocin, Blasticidin and Zeocin) in an incubator being under conditions of 37° C., 5% $CO_2$, and not less than 80% humidity. The D1.1 cells were incubated in an incubator being under the same conditions using an RPMI1640 culture medium containing 10% fetal bovine serum. Next, the D1.1 cells were plated to a 96-well cell culture plate under the condition of a $5.0\times10^4$ cells/well concentration, or the recombinant soluble TNF-α proteins were plated to the 96-well cell culture plate at a concentration of 10 ng/mℓ. To assess simultaneous binding reactions for two kinds of samples, D1.1 cells and recombinant soluble TNF-α proteins were plated together to a 96-well cell culture plate. The serially diluted samples (pre-treated with human serum albumin) were treated on the 96-well cell culture plate to which either or both of the cells and the recombinant proteins were plated, and then allowed to react for 3 hours in an incubator being under conditions of 37° C., 5% $CO_2$, and not less than 80% humidity. After the 3 hour reaction, the CD40L HEK-Blue™ cells were treated on all wells of the plate at a concentration of $5\times10^4$ cells/well, and then reacted in an incubator being under the same conditions for 21 hours. Next, each 160 μℓ of a QUANTI-Blue reagent (SEAP detection reagents, InvivoGen), which was reacted in 37° C. water for 30 minutes, was seeded to all wells of a new 96-well cell culture plate, and 40 μℓ of a reaction solution reacted in an incubator for 21 hours was placed to each well containing the Quanti-Blue reagent to then be reacted. After the reacting in a 37° C. incubator for 1 hour, and the absorbance was measured at 655 nm wavelength.

Example 4. Results

1. Experimental Results for APB-A1
(1) Expression and Production of APB-A1

Figure 2A:
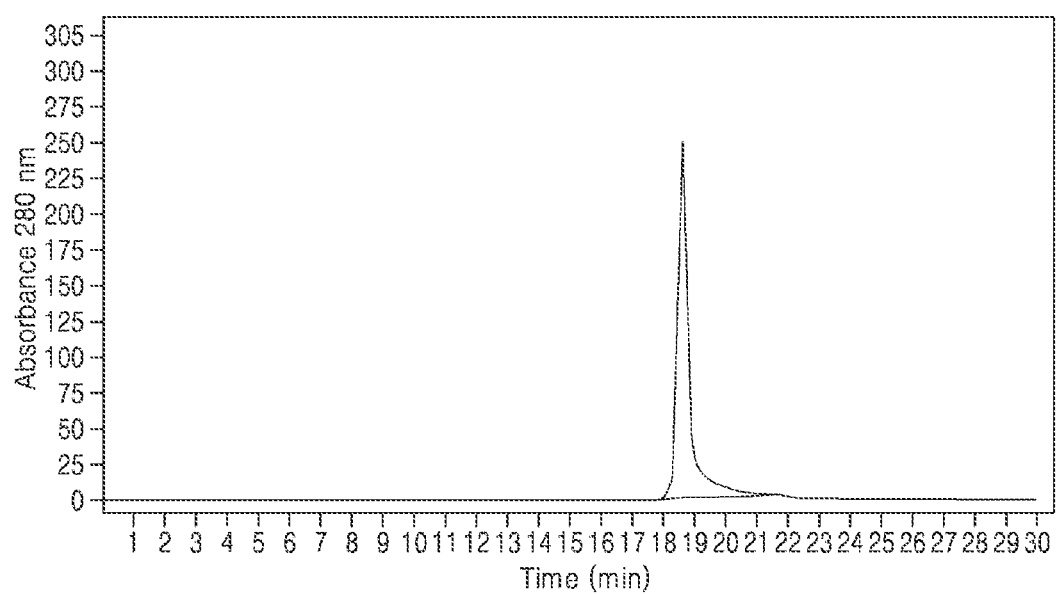
FIGS. 2A and 2B represent the HPLC analysis and SDS-PAGE results for APB-A1.
Figure 2B:
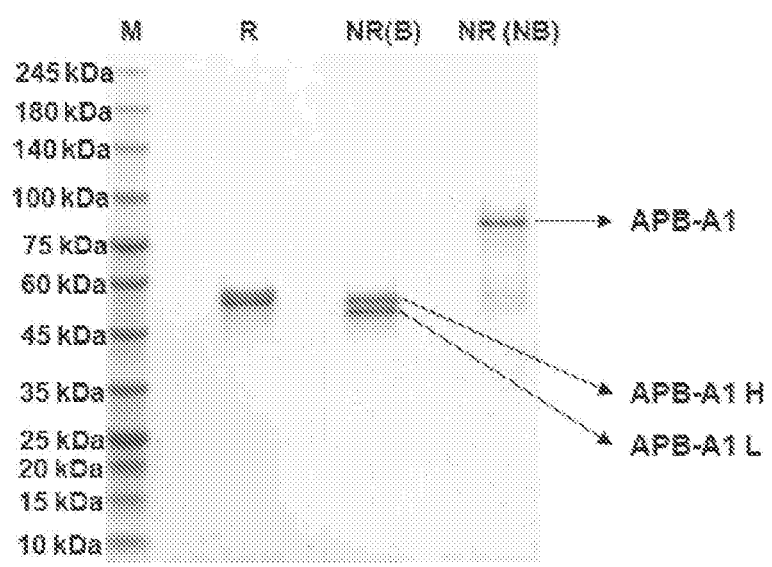

To produce APB-A1, a hu5c8 scFv ($V_L+V_H$)-flexible linker (SEQ ID NO:3-GGGGSGGGGSGGGGS; linker 1)-SL335 Fd ($V_H+C_{H1}$) (termed APB-A1 heavy chain) gene, and a hu5c8 scFv ($V_L+V_H$)-flexible linker (SEQ ID NO:4-GSTSGSGKPGSGEGSTKG; linker 2)-SL335 kappa ($V_L+$CL) (termed APB-A1 L light chain) gene were linked by a linking PCR. After cloning to pcDNA3.3 and pOptiVEC vector, respectively, the genes were transfected to ExpiCHO-S™ cell line for transient expression, and it was identified by Western blotting whether to normally express 101.7 kDa-APBA1 (APB-A1 H chain; 50.7 kDa-483 amino acids and APB-A1 L chain; 50.9 kDa-478 amino acids). Next, for stable expression in the CHO cell, the APB-A1 H and APB-A1 L genes were cloned to pd2535nt and pd2539vector, respectively, to produce recombinant vectors (FIG. 1A), and it was confirmed by amino acid sequencing that no abnormality was found (FIG. 1B). FIG. 1A represents APB-A1 heavy and light chains inserted into pd2535nt and pd2539 vectors. FIG. 1B represents amino acid sequences of APB-A1 H (total of 483 amino acids) and APB-A1 L (total of 478 amino acids), which are SL335 H and SL335 L having hu5c8 scFv linked by a linker 1 and a linker 2. The recombinant vectors were transfected to GS null CHO K1 cells prior to use, and screened using MSX and puromycin, thereby establishing a stable CHO cell line. For production of APB-A1 protein to be used for evaluation of in vitro and in vivo effects, the stable CHO cell line was cultured in a bioreactor, a supernatant was acquired, and purification was performed through a total of three steps including affinity chromatography, cation exchange chromatography and anion exchange chromatography. The APB-A1 protein was acquired with yield of 95% greater through the affinity chromatography as the first step, and the APB-A1 sample was obtained with yield of 82% using the second and third steps of cation and anion exchange chromatography steps for removing impurity and endotoxin. Next, to assess the purity of a protein, SE-HPLC was performed under a native condition, the results of experiments repeated a total of three times confirmed that the perfect APB-A1 sample had purity of 95% or greater, and FIG. 2A represents one of the repeated experiments. To identify the purity and molecular weights of the sample obtained through the purification process, the obtained sample was analyzed by SDS-PAGE under reducing, nonreducing (boiled), and nonreducing (not boiled) conditions (FIG. 2B). As such, FIG. 2A represents the analysis result of APB-A1 characteristics identified by HPLC and FIG. 2B represents the analysis result of APB-A1 characteristics identified by SDS-PAGE. Characteristics of the APB-A1 purified from the supernatant of the purified GS null CHO K1 cell culture medium were identified on a 4 to 15% gradient gel under reducing (R), nonreducing (boiled) (NR (B)) and nonreducing (not boiled) (NR (NB)) conditions by (A) HPLC and (B) SDS-PAGE In the HPLC analysis of FIG. 2A, the protein sample was analyzed by SE-HPLC under a negative condition (without DTT). The purity was 95% or greater. In the SDS-PAGE gel represented in FIG. 2B, protein bands were visualized by an Ez-gel staining solution. As described above, theoretical molecular weights of APB-A1 H (50.7 kDa) and APB-A1 L polypeptide (50.9 kDa) were 50.7 kDa and 50.9 kDa, respectively. Under the reducing (R) condition, two protein bands were identified around 50 kDa in molecular weight size, but it was quite difficult to accurately discriminate two bands from each other because the molecular weights of the APB-A1 H and L polypeptides are very similar to each other (lane R of FIG. 2B). Under the nonreducing (boiled) condition, two bands were identified at positions in little smaller sizes [lane NR(B) of FIG. 2B] than under the reducing condition, and Western blotting confirmed that the APB-A1 H band of the two bands was positioned slightly higher than the APB-A1 L band (data not shown). Under the nonreducing (not boiled) condition, it was confirmed that the identified APB-A1 had a molecular weight size smaller than the theoretical molecular weight size thereof (101.6 kDa) [lane NR(NB) of FIG. 2B].

(2) Molecular Characteristics of APB-A1

Figure 3:
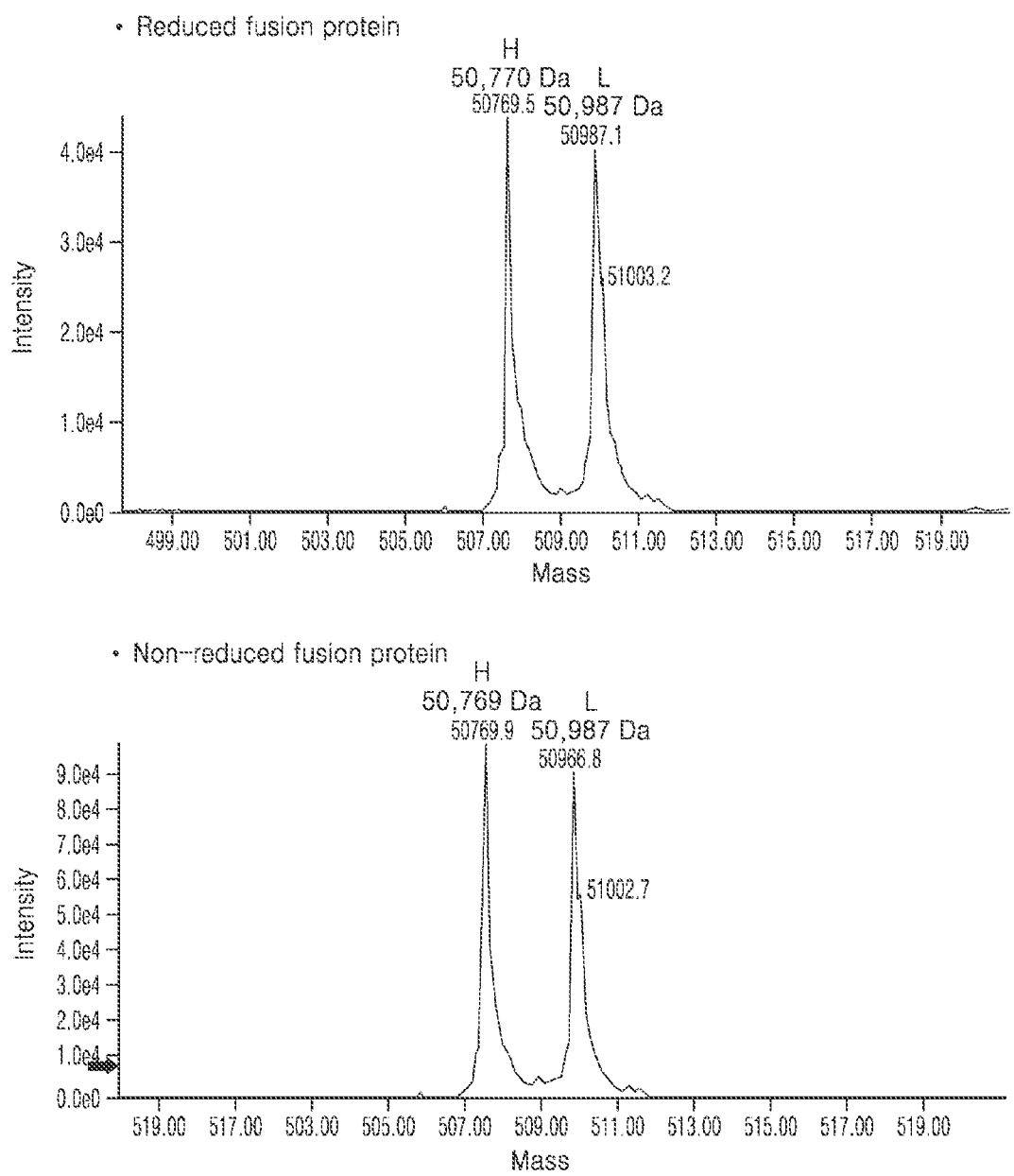
FIG. 3 represents the mass analysis result for APB-A1.
Figure 4A:
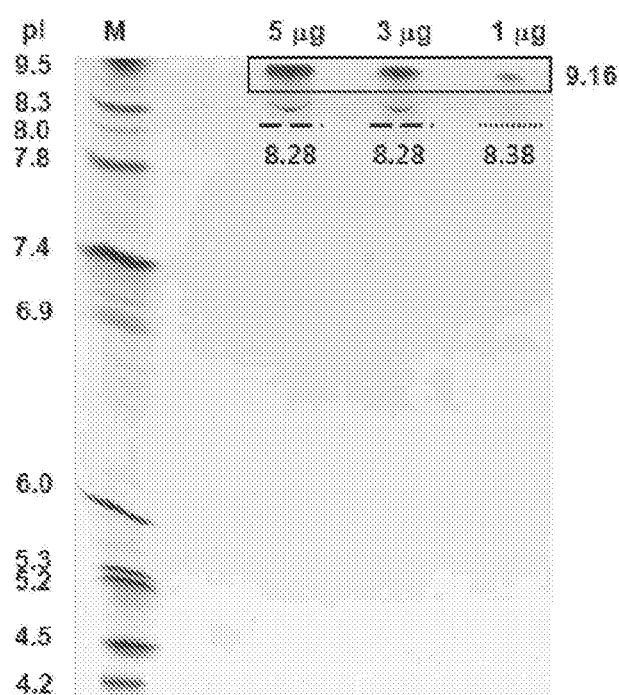
Figure 5:
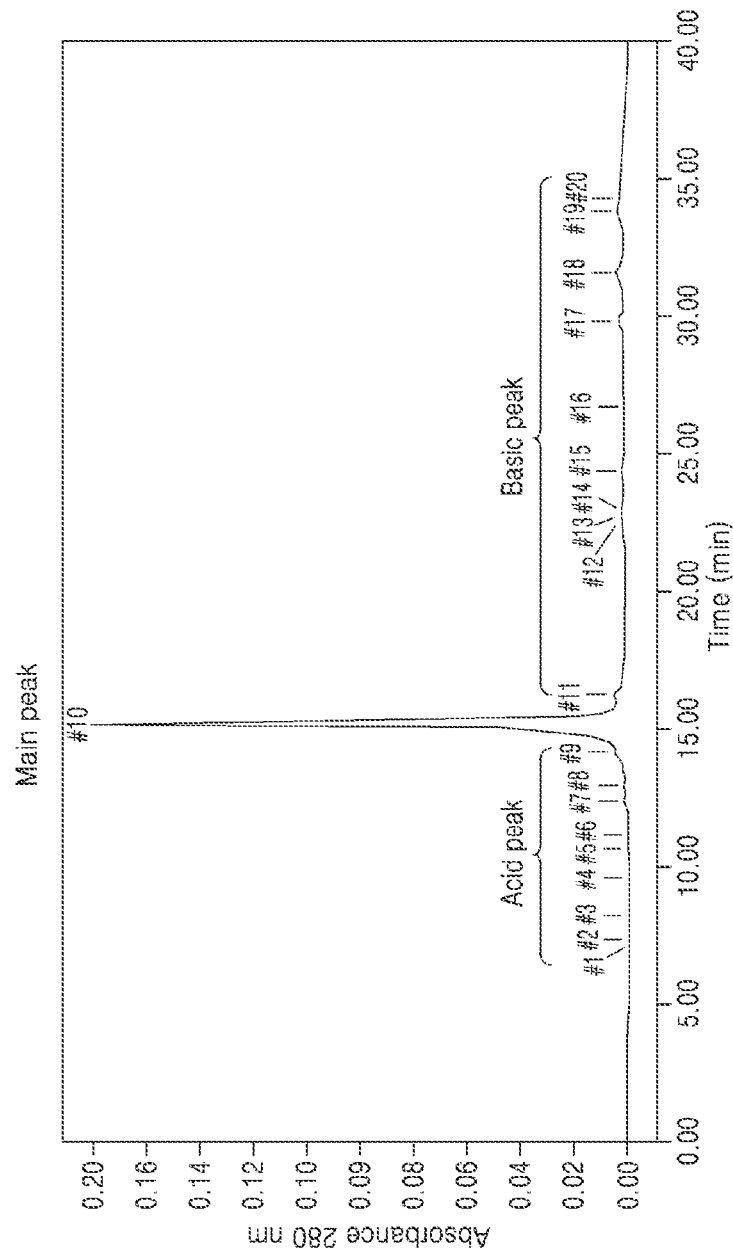
FIG. 5 represents a change in the charge quantity of APB-A1.

To accurately measure the mass of APB-A1 protein, Q-TOF analysis was performed under reducing and nonreducing conditions. The measured masses of the heavy (H) and light (L) chains of APB-A1 were 50.77 kDa and 50.98 kDa (FIG. 3). In FIG. 3, characteristics of the purified APB-A1 protein were identified using a mass spectrometry instrument (ProteomeTech, South Korea). In mass spectrometry, the protein sample was analyzed under reducing and nonreducing conditions. The theoretical molecular weights of the APB-A1 heavy and light chains were 50,777 Da and 50,994 Da, which are substantially identical with the values measured by the mass spectrometry analysis of this example. Considering that the APB-A1 had no N-linked glycosylation site, as confirmed using glycosylation prediction software, and that any peaks other than APB-A1 H and L peaks were not actually observed through Q-TOF analysis, it was predicted that the APB-A1 would not comprise N-linked glycosylation. As confirmed from the analysis result obtained using pI analysis software, the APB-A1 had a theoretical pI value of 8.65, and the actual measurements of isoelectric focusing (IEF) at pH 3-10 and capillary isoelectric focusing (cIEF) were 9.16 and 9.2, respectively (FIGS. 4A and 4B). In FIGS. 4A and 4B, the pI analysis for the purified APB-A1 protein was performed by ProteomeTech. The pI values identified by isoelectric focusing (IEF) gel at pH 3-10, shown in FIG. 4A, and capillary isoelectric focusing (cIEF), shown in FIG. 4B, were 9.16 and 9.2, respectively. To accurately analyze charge variants of APB-A1, charge variant experiments were repeatedly conducted using ultra performance liquid chromatography (UPLC), and the UPLC assay resulted in a peak profile showing that 76.3% of the samples had main peaks with constant charges, 4.6% had acid peaks and 19.1% had basic peaks (FIG. 5).

(3) In Vitro Functional Characteristics of APB-A1

To assess binding affinities of APB-A1 to HSA and rhCD40L antigens, the biolayer interferometry using an Octet Red instrument was performed. The assessment result confirmed that the dissociation constants KD of APB-A1 for the HSA and rhCD40L antigens were 748 pM and 127 pM, respectively. Therefore, it was confirmed that the APB-A1-HSA equilibrium dissociation constant ($K_D$) was about 2.6 times larger than the SL335-HSA $K_D$ (748 pM vs. 286 pM, respectively), and APB-A1-rhCD40L dissociation constant was about 2.6 times larger than the hu5c8 IgG1-rhCD40L $K_D$ (127 pM vs. 49.6 pM, respectively).

To confirm binding affinities of APB-A1 to HSA and rhCD40L antigens, the biolayer interferometry using an Octet Red instrument was performed again. The assessment result confirmed that the equilibrium dissociation constant ($K_D$) of APB-A1 for the HSA and rhCD40L antigens were 628 pM and 186 pM, respectively. The average of the two results are provided in Table 5.

TABLE 5

| Binder | Ligand | $K_D$(M) | $K_{on}$(1/Ms) | $K_{dis}$(1/s) |
|---|---|---|---|---|
| HSA | APB-A1 | 6.88E−10 | 8.04E+05 | 5.60E−04 |
| hCD40L | | 1.57E−10 | 7.44E+05 | 1.15E−04 |

Figure 6:
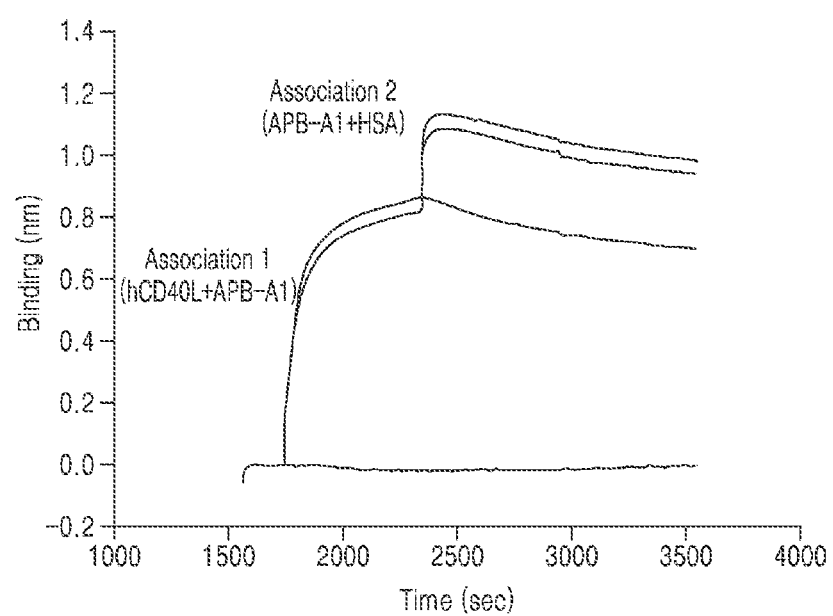
FIG. 6 represents simultaneous binding of rhCD40L-APB-A1-HSA.
Figure 7:
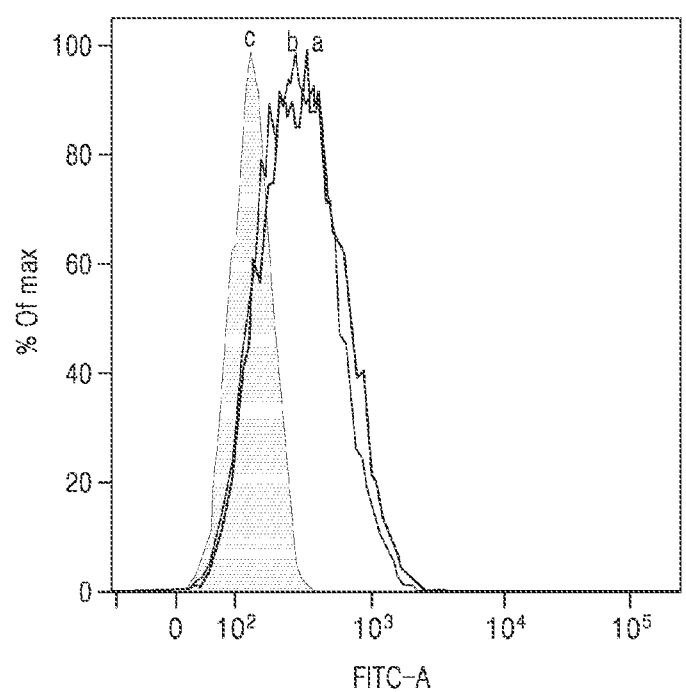
FIG. 7 represents the result of flow cytometry analysis.
Figure 8A:
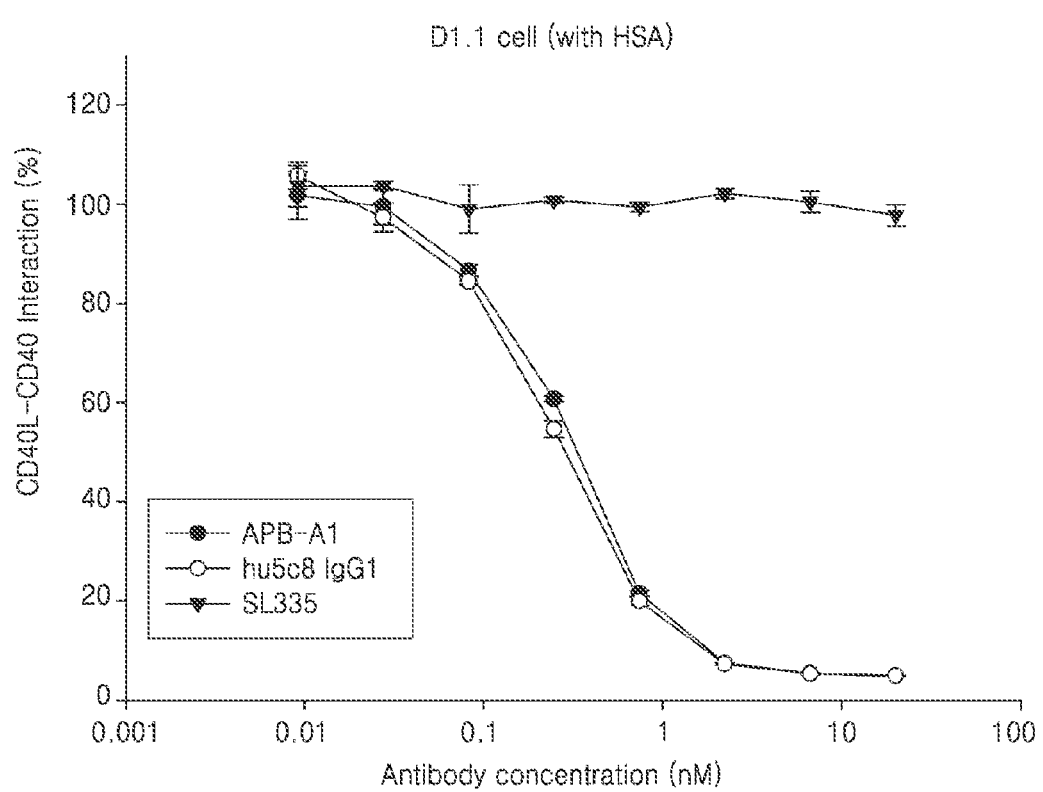
FIGS. 8A to 8D represent the in vitro analysis results for APB-A1.
Figure 8B:
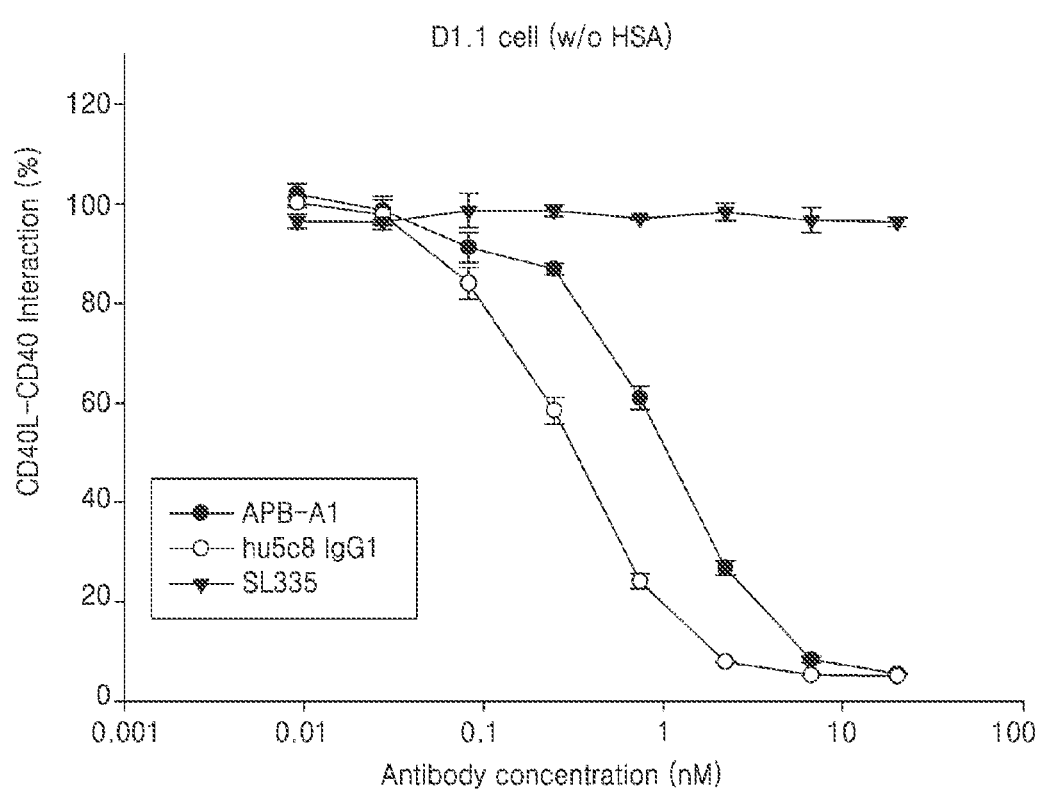
Figure 8C:
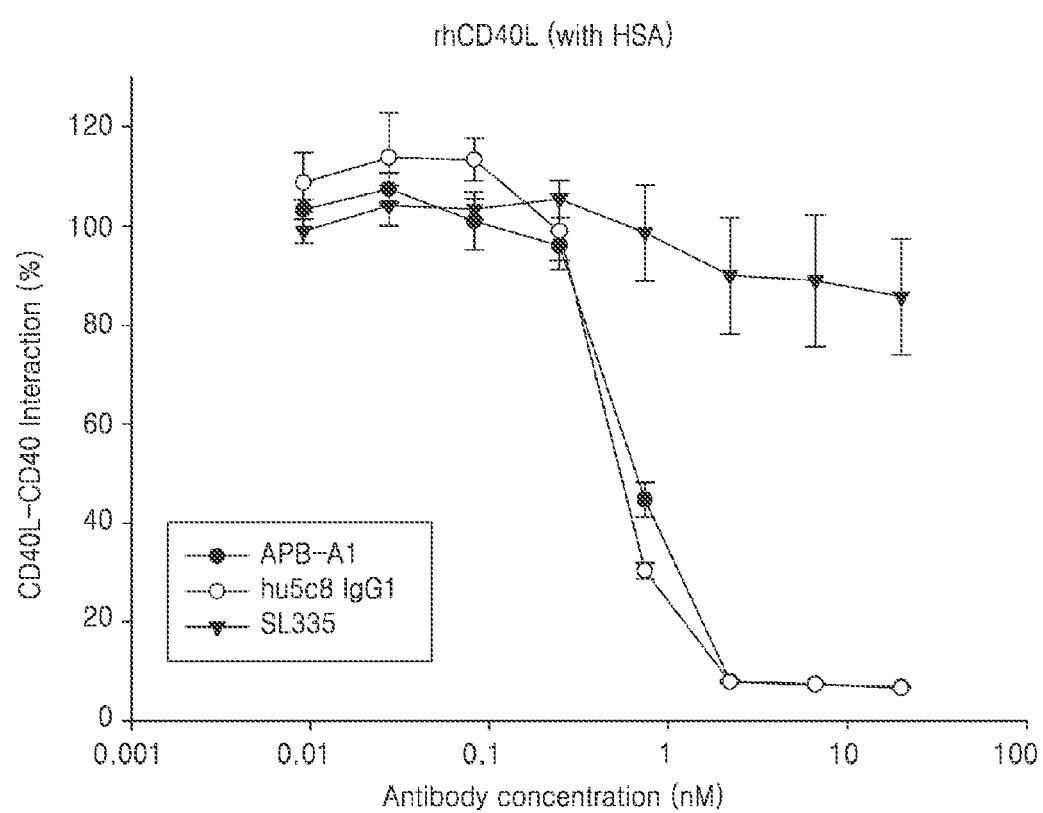
Figure 8D:
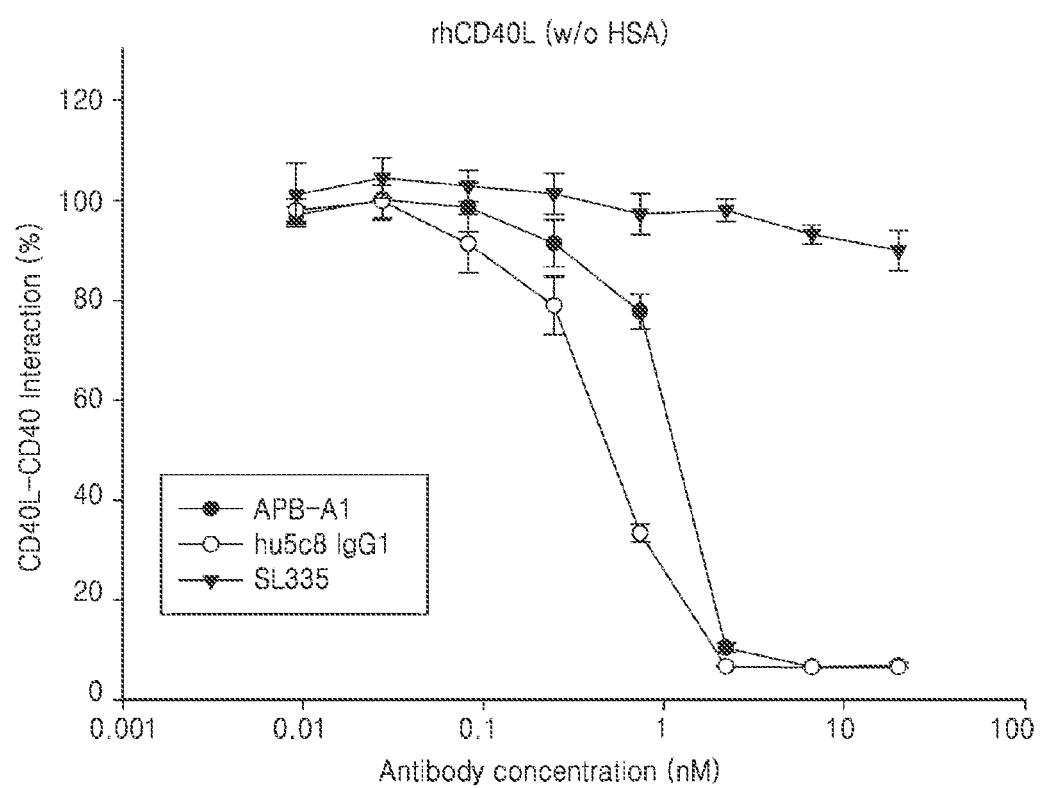

In addition, to identify that APB-A1 simultaneously bind to HSA and rhCD40L antigens, biolayer interferometry was performed such that the rhCD40L antigen was immobilized to an AR2G biosensor and APB-A1 and HSA were allowed to sequentially react therewith. As a result, it was confirmed that APB-A1 was capable of simultaneously binding to HSA and rhCD40L antigens (FIG. 6). For cell-based in vitro evaluation, a D1.1 cell expressing mCD40L was used, and as a preliminary experiment, it was identified by flow cytometry analysis whether APBA1 and hu5c8 IgG1 as a control group bind to the mCD40L expressed by the D1.1 cell. According to the analysis results, it was confirmed that SL335 as a negative control group did not bind to the mCD40L of the D1.1 cell, while APB-A1 and hu5c8 IgG1 were bound (FIG. 7). In FIG. 7, APB-A1 (a) and hu5c8 IgG1 (b) were allowed to bind to the D1.1 cell expressing the mCD40L, and SL335 (c) not binding to the D1.1 cell was used as the negative control group. Next, to identify the potency of APB-A1 for suppressing CD40-CD40L interaction, HEKBlue™ CD40L reporter cell was combined with the D1.1 cell or the rhCD40L antigen with or without HSA and then reacted by adding thereto APB-A1, hu5c8 IgG1 and SL335 (at concentrations ranging from 0.01 to 22.2 nM), followed by measuring alkaline phosphatase (AP) responses of the reporter cell (FIGS. 8A to 8D). In FIGS. 8A to 8D, the capacities of APB-A1 and hu5c8 IgG1 inhibiting the CD40L-CD40 interaction in the absence of HSA were 0.9907 nM and 0.289 nM (FIG. 8B) and 1.031 nM and 0.4729 nM in the presence of HSA (FIG. 8A). The $IC_{50}$ values for the inhibiting capacities of APB-A1 and hu5c8 IgG1 on the interaction between soluble CD40L and CD40 in the absence of HSA were 1.031 nM and 0.4729 nM (FIG. 8D) and 0.6371 nM and 0.501 nM in the presence of HSA (FIG. 8C). In the experiment using a combination of a reporter cell and a D1.1 cell, APB-A1 demonstrated low suppressive potency that is about 3 times lower than that of hu5c8 IgG1 in the absence of HSA, while APB-A1 and hu5c8 IgG1 demonstrated substantially the same suppressive efficacy in the presence of HSA (FIGS. 8A and 8B). Similarly, in the experiment using a combination of a reporter cell and rhCD40L antigen, the suppressive potency of APB-A1 was about 2.1 times lower than that of hu5c8 IgG1 in the absence of HSA, while APB-A1 and hu5c8 IgG1 demonstrated substantially the same suppressive efficacy in the presence of HSA (FIGS. 8C and 8D). Meanwhile, SL335 used as a negative control demonstrated no suppressive efficacy under any condition (FIGS. 8A-8D). In the case of using the D1.1 cell, the $IC_{50}$ values representing the CD40L-CD40 interaction inhibiting capacity, which were derived from the results shown in FIGS. 8A and 8B, were 0.9907 nM in the absence of HSA and 0.2988 nM in the presence of HSA, respectively. The $IC_{50}$ value of hu5c8 IgG1 as a positive control was identified to be about 0.2 to 0.3 nM, indicating that the presence or absence of HSA did not affect the $IC_{50}$ value of hu5c8 IgG1 (FIGS. 8A and 8B). When the rhCD40L antigen was used, the $IC_{50}$ values were 1.031 nM in the absence of HSA and 0.6371 nM in the presence of HSA, and the $IC_{50}$ value of hu5c8 IgG1 was identified to be about 0.47 to 0.5 nM, which was substantially the same result as in the experiment stated above (FIGS. 8C and 8D).

(4) Analysis of APB-A1 Effect on Platelet Aggregation

Figure 9A:
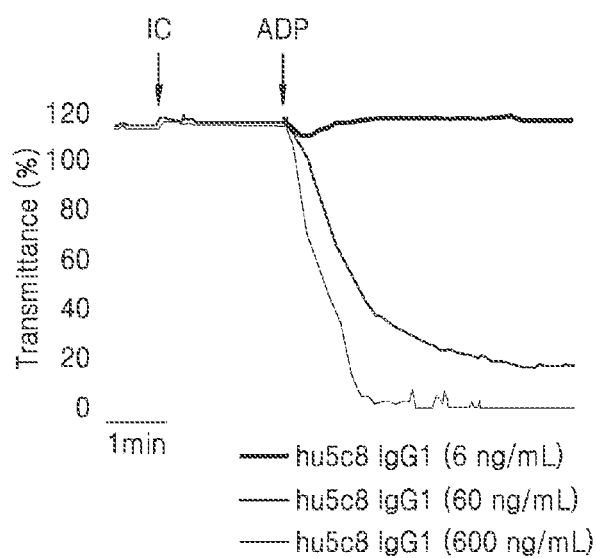
FIGS. 9A to 9D represent various IC effects on platelet aggregation.
Figure 9B:
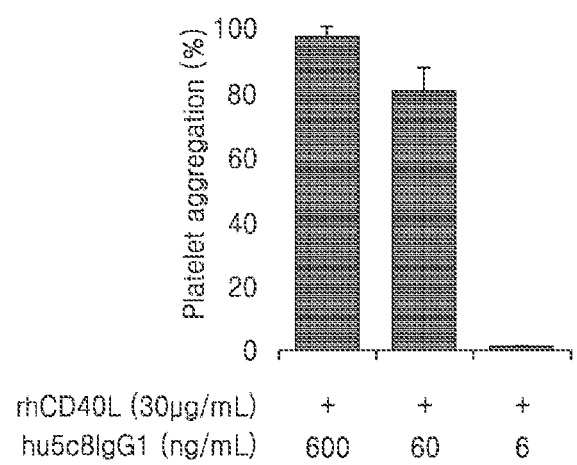
Figure 9C:
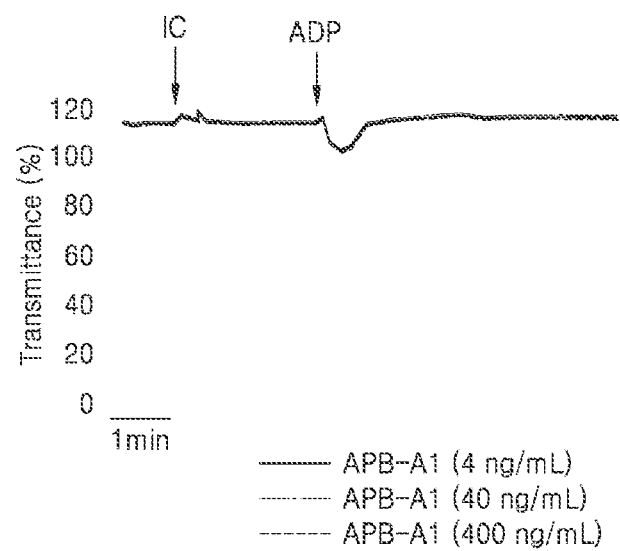
Figure 9D:
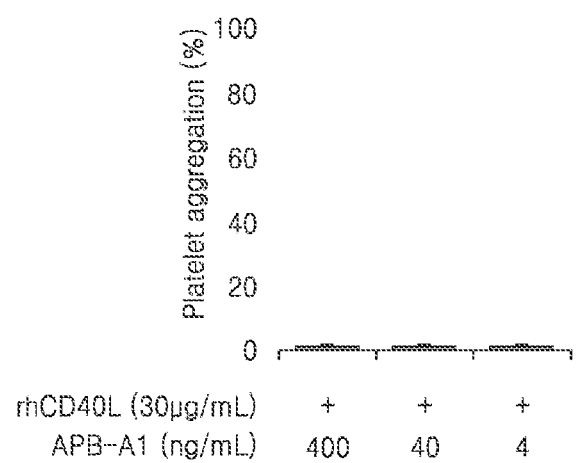
Figure 10:
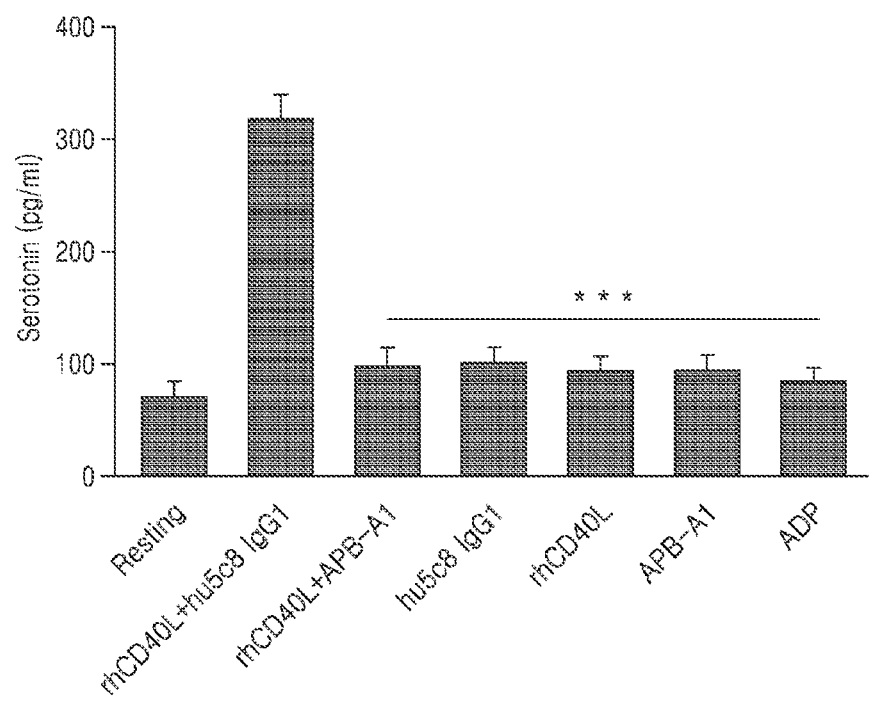
FIG. 10 represent various IC effects on serotonin levels.

It was determined whether the platelet aggregation known as a typical side effect of the conventional anti-CD40L IgG antibody was caused by APB-A1. To this end, rhCD40L hu5c8 IgG1 IC and rhCD40L+APB-A1 IC were produced and then allowed to react with the platelet stimulated by ADP, thereby determining as to occurrence of platelet aggregation by measuring the transmittance. The result showed that only the rhCD40L hu5c8 IgG1 IC intensely stimulated platelet aggregation (FIGS. 9A to 9D). In FIGS. 9A to 9D, PRP was pre-cultured with hCD40L (30 μg/mℓ) and different concentrations (6 ng/mℓ, 60 ng/mℓ and 600 ng/mℓ) of hu5c8 IgG1 or different concentrations (4 ng/mℓ, 40 ng/mℓ and 400 ng/mℓ) of APB-A1, in the presence of 5 to 10 mM $CaCl_2$) at 37° C. for 2 minutes. Next, the platelet was further stimulated by ADP at a concentration less than the optimum concentration, while continuously stirring. In the case of the sample hu5c8 IgG1+rhCD40L IC, the platelet aggregation occurred (FIGS. 9A and 9B), but the rate of platelet aggregation was low in the case of the sample rhCD40L+APB-A1 (FIGS. 9C and 9D). The data represents the standard deviation (SD) of the experiments with at least 6 different donors. To quantitatively analyze the results represented in FIGS. 9A to 9D, platelet aggregation % was calculated, and the calculation result showed that the sample rhCD40L+hu5c8 IgG1 IC demonstrated a response of about 80% or greater at concentrations of 60 ng/mℓ, and 600 ng/mℓ, while the sample rhCD40L+APB-A1 demonstrated less than about 10% of platelet aggregation at a concentration of 400 ng/mℓ (FIG. 9D). In addition, the concentrations of serotonin released when the platelet was activated were measured, and the assessment results showed that the serotonin release levels were not increased with the activation by rhCD40L+APB-A1 and other sample groups while the serotonin release level was increased to about 300 pg/mℓ, with the activation by rhCD40L+hu5c8 IgG1 IC (FIG. 10). In FIG. 10, the amount of serotonin released was increased in the case of recombinant rhCD40L+hu5c8 IgG1, but significant differences were not observed in other groups. The data represents the average value±standard deviation (SD) of four or more independent experiments (***$p<0.001$ compared to the IC (recombinant hCD40L+hu5c8 IgG1) control).

(5) Pharmacokinetics Research for APB-A1

Figure 11:
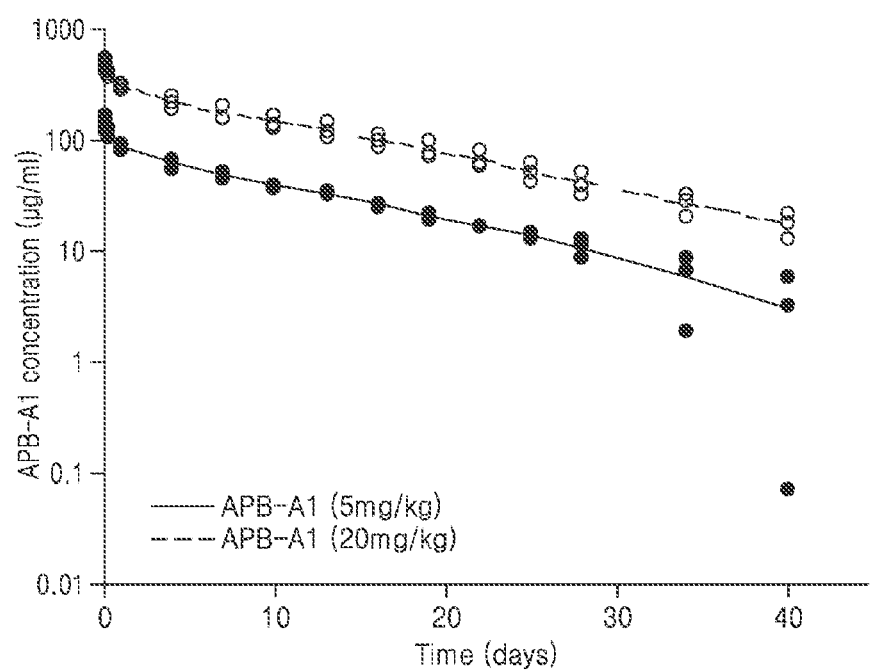
FIG. 11 represents PK values for APB-A1 concentrations measured using cynomolgus monkeys.

To assess in vivo half-lives of APB-A1, pharmacokinetic assay was performed using cynomolgus monkey models (n=3/group). APB-A1 was administered in two dosages of 5 mg/kg and 20 mg/kg through a single intravenous injection. After collecting blood samples at the same points in time as in the Materials and Methods sections, the concentrations of APB-A1 in blood plasma were measured using PK ELISA (FIG. 11). In FIG. 11, purified APB-A1 antibodies were injected to male cynomolgus monkeys (n=3) at various concentrations (5 mg/kg and 20 mg/kg). The experiments were conducted by SNBL. The APB-A1 concentrations of samples at the respective points were measured by ELISA, and the data represents the average of the experiments conducted. Half-lives were calculated using the data based on the ELISA result using Phoenix WinNonlin software (ver 6.4; Certara L P, Princeton, NJ, USA), and the half-lives of 5 mg/kg APB-A1 and 20 mg/kg APB-A1 were identified to be about 7 and 9.6 days, respectively. Therefore, it was understood that the APB-A1 half-life was increased at a dose of 20 mg/kg to be about 1.4 times longer than that at a dose of 5 mg/kg. Cmax values were 143 μg/ml and 509 μg/ml at doses of 5 mg/kg and 20 mg/kg, respectively, and renal clearance ($C_L$) rates were 4.44 ml/day/kg and 4.72 ml/day/kg, which were similar levels regardless of dose (Table 6).

TABLE 6

| Species | Group | Single Dose Level (mg/kg) | $T_{1/2}$ (day) | $C_{max}$ (μg/ml) | $AUC_{inf}$ (μg · day/ml) | CL (ml/day/kg) | $V_{dss}$ (ml/kg) |
|---|---|---|---|---|---|---|---|
| Cynomolgus Monkey | 1 | 5 | 6.94 ± 4.6 | 143 ± 18 | 1130 ± 80 | 4.44 ± 0.32 | 54.1 ± 9.7 |
| | 2 | 20 | 9.59 ± 0.79 | 509 ± 23 | 4290 ± 580 | 4.72 ± 0.6 | 64.1 ± 6.0 |

(6) APB-A1 Pharmacodynamics Assay

Figure 12A:
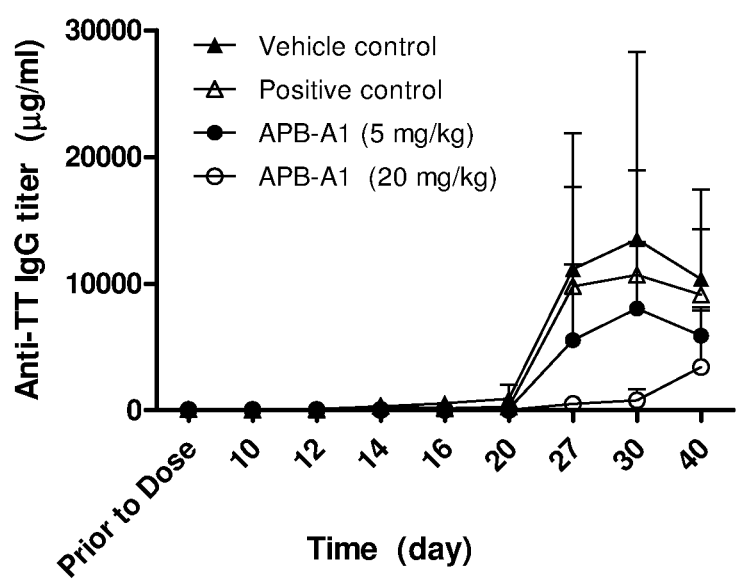
FIGS. 12A and 12B represent the pharmacokinetic analysis results using cynomolgus monkeys.
Figure 12B:
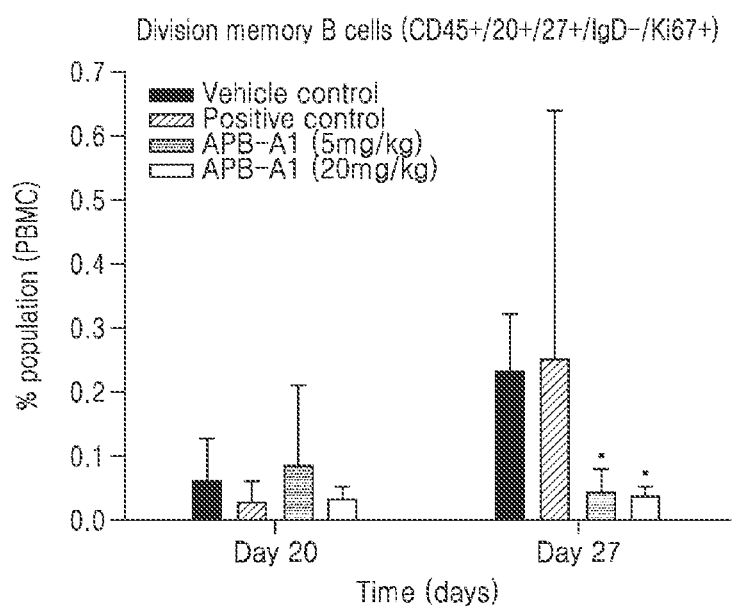

To evaluate the in vivo potency of APB-A1, pharmacodynamics research was performed using cynomolgus monkeys (n=3/group). First, TT was intramuscularly injected twice to animals to induce first and memory anti-TT antibody immune responses, and a vehicle (negative control, one single-dose injection), a positive control (DXT; 1 mg/kg, 4-dose injections), and APBA1 (5 mg/kg or 20 mg/kg, one single-dose injection) were intravenously administered to each animal, and concentrations of anti-TT IgG antibodies produced in serum were measured by ELISA. As a result, although the first anti-TT IgG immune response induced by the single-dose TT injection was not statistically significant, the vehicle control induced a normal first anti-TT IgG immune response, while the first anti-TT IgG immune response was not observed in DXT and APB-A1 injected groups (FIG. 12A). In FIGS. 12A and 12B, to analyze the inhibition of memory antibody responses, tetanus toxoid (TT) was injected to female cynomolgus monkeys (n=3) with vehicle, DXT and APB-A1 (5 mg/kg and 20 mg/kg). The experiments was conducted by SNBL. (A) Anti-TT antibody levels were measured by ELISA. (B) Memory B cell percentages were significantly reduced in both groups of 5 mg/kg APB-A1 and 20 mg/kg APB-A1 (* p<0.03 versus vehicle control by t-test). 20 days after the primary TT injection, to induce a memory anti-TT IgG immune response, second TT injection was performed, and then concentrations of anti-TT IgG antibodies produced in serum were measured. As a result, normal anti-TT IgG immune responses appeared in the vehicle control and DXT group after the second TT injection, APB-A1 injected groups demonstrated statistically significant effects in inhibiting second anti-TT IgG immune responses on day 27 in a dose-dependent manner. It was confirmed from initial CD40-CD40L responses that APB-A1 possessed suppressive potency, and population percentages of the respective groups were compared through immunophenotyping. Memory B cells (CD45+20+/27+IgD−/Ki67+) and dividing populations (CD45+/20+/Ki67+) of B cells demonstrated statistically significant suppressive potencies of APB-A1 up until day 27 after the second TT injection (FIG. 12B). In assays of plasma cells (CD45+20−/27hi/IgD−) and total B cells (CD45+/20+), it was confirmed that there was no difference between groups, and the overall inhibiting effects for the vehicle control were gradually reduced on days 30 and 40 (data not shown).

2. Experimental Results for APB-B1

(1) Production of SAFA-based Bispecific Antibody

Figure 13A:
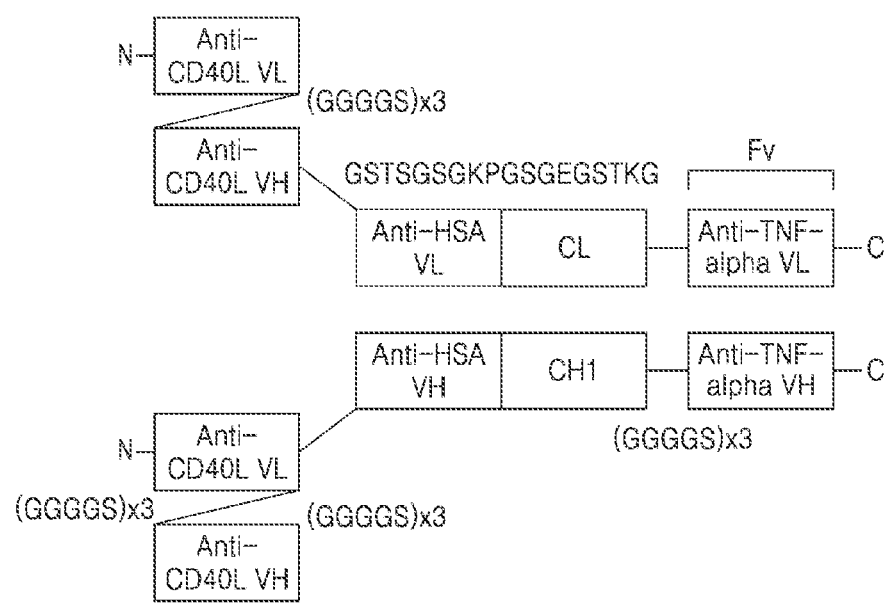
FIGS. 13A to 13C represent SAFA-based bispecific antibodies and mammalian expression vectors.
Figure 13B:
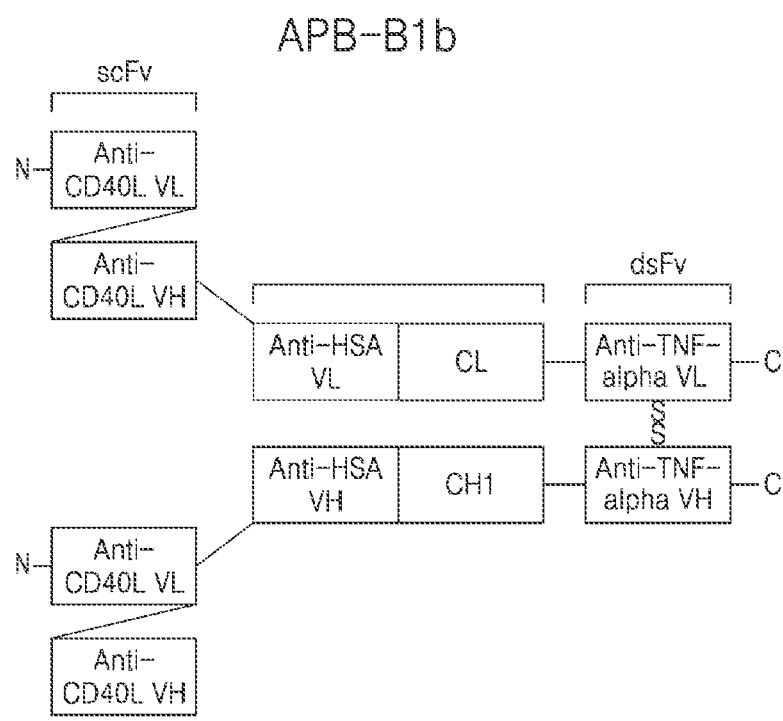
Figure 13C:
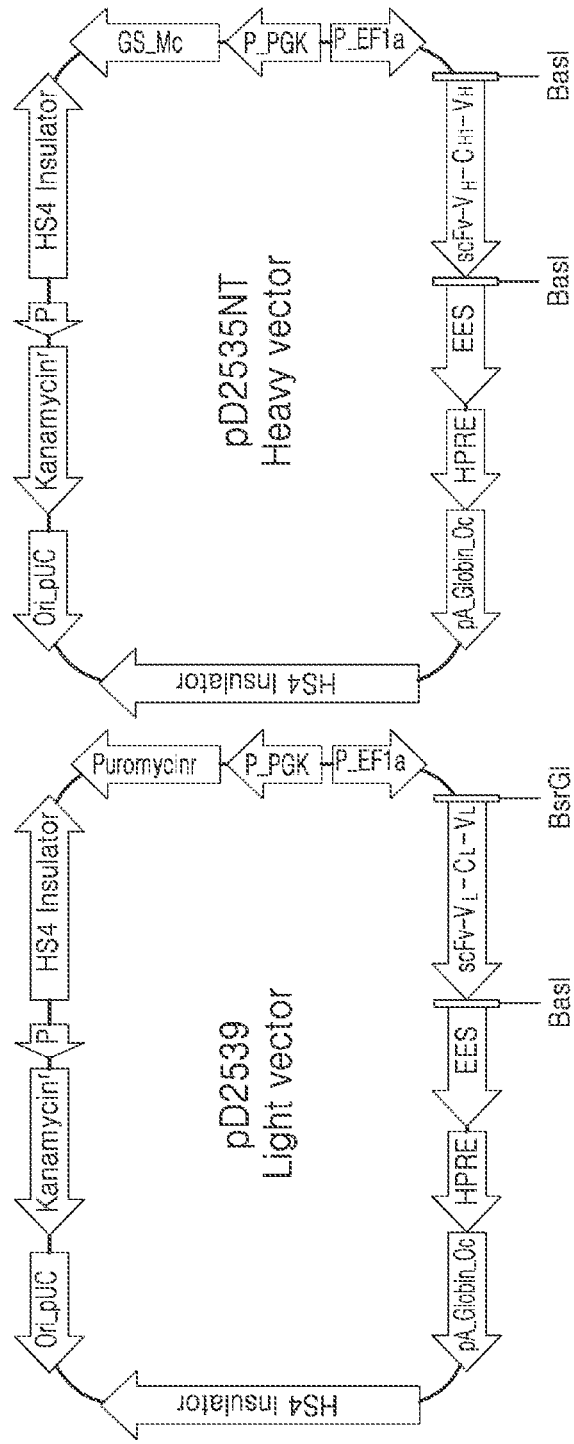
Figure 15A:
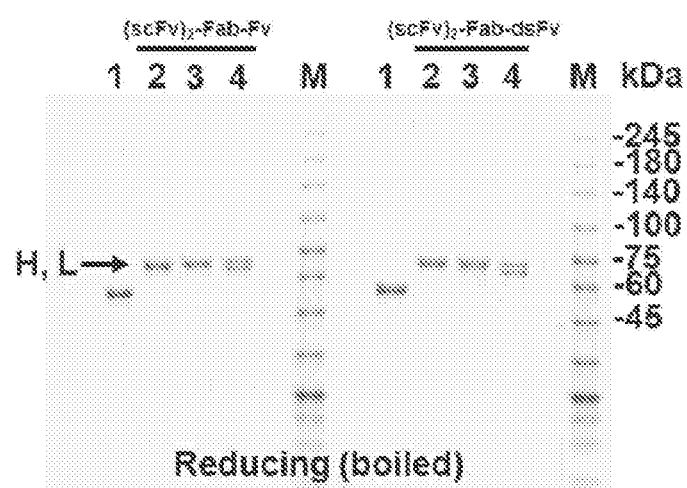
FIGS. 15A to 15D represent bispecific antibody constructs, purified by CaptureSelect IgG-$C_{H1}$ affinity chromatography.
Figure 15B:
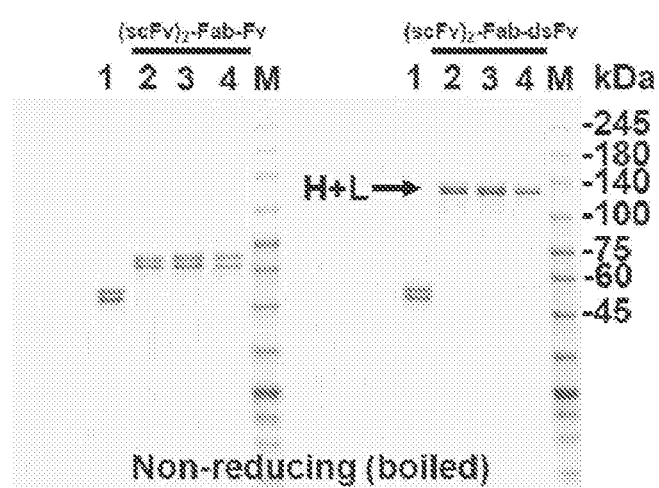
Figure 15C:
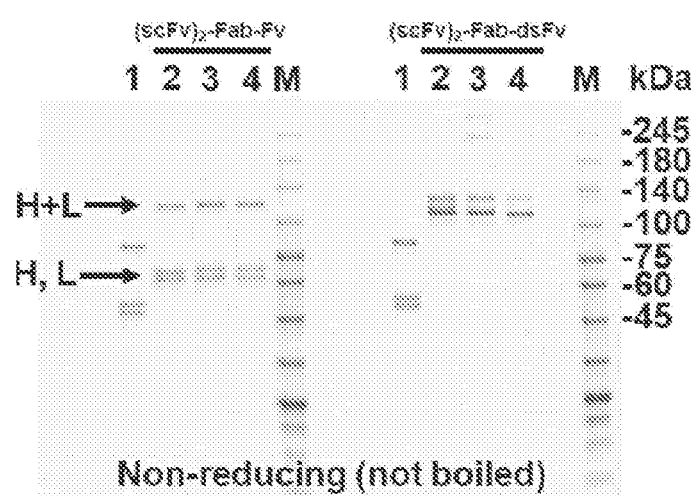
Figure 15D:
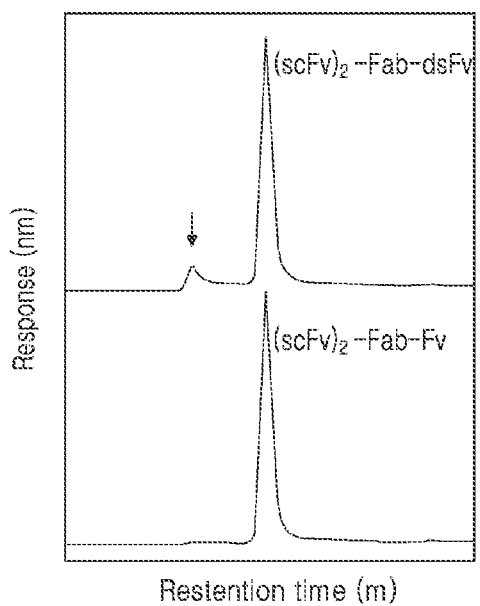

For production of SAFA-based bispecific antibodies, cysteine forming an inter-chain disulfide bond between $C_{H1}$ (hinge region, EPKSC−) of a heavy chain and CL (NRGEC−) of a light chain was substituted with serine (Ser), and resulting mutant forms of SL335 Fab, EPKSS- and NRGES-having two inter-chain disulfide bonds removed therefrom, were used. An scFv antibody fragment [with $V_H$ and $V_L$ gene sequences derived from ruplizumab (or hu5c8)] binding to human CD40L were fused to N-terminals of heavy and light chains of the SL335 Fab using a (GGGGS)3 (SEQ ID NO:3) or GSTSGSGKPGSGEGSTKG (SEQ ID NO:4) peptide linker, and an Fv antibody fragment (with $V_H$ and $V_L$ gene sequences derived certolizumab pegol) binding to TNF-α, an Fv antibody fragment (with $V_H$ and $V_L$ gene sequences derived from ustekinumab) binding to IL-23, and an antibody fragment (with $V_H$ and $V_L$ gene sequences derived from anifrolumab) binding to INFAR1, were fused to the C-terminal of SL335 Fab using peptide linkers, respectively. In the case of Fv fusion, a C-terminal heavy chain $V_H$ fragment and a C-terminal light chain $V_L$ fragment were fused. To compare antibody functions depending on the presence or absence of artificial inter-chain disulfide bond formed between the $V_H$ and $V_L$ fragments of Fv, a (scFv)$_2$-Fab-Fv format without disulfide bond was substituted with G44C of $V_H$ (G542C, FIG. 14) and Q100C of $V_L$ (Q593C, FIG. 13A), thereby producing (scFv)$_2$-Fab-dsFv formats with a disulfide bond, respectively. In FIGS. 13A and 13B, APB-B1a (a), (scFv)$_2$-Fab-Fv construct and APB-B1b (b), (scFv)$_2$-Fab-dsFv construct, having anti-CD40L scFv, anti-HSA Fab and anti-TNF-α Fv (with or without a disulfide bond) are linked by (GGGGS)3 (SEQ ID NO:3) and GSTSGSGKPGSGEGSTKG (SEQ ID NO:4) peptide linkers. The (scFv)$_2$-Fab-dsFv comprises an inter-chain disulfide bond (ss) between variable light chain ($V_L$) and variable heavy chain ($V_H$) of anti-TNF-α dsFv fragment, while the (scFv)$_2$-Fab-Fv does not comprises an inter-chain disulfide bond. FIG. 13C is a diagram representing recombinant pD2539 and recombinant pD2535NT after DNA cloning. Here, bispecific antibodies fused with Fv and dsFv derived from certolizumab were termed APB-B1a and APB-B1b, respectively (FIGS. 13A and 13B).

In FIG. 14, for the inter-chain disulfide bond between heavy and light chains of APB-B1b, a G542C residue in the heavy chain and a Q593C residue in the light chain are represented in bold. The residues of the peptide linkers [(GGGGS)3 (SEQ ID NO:3) and GSTSGSGKPGSGEG-STKG (SEQ ID NO:4)] are underlined. The thus produced SAFA-based bispecific antibody protein has a theoretical size of up to 128 kDa, and in order to utilize a CHO cell expression system, two polypeptide coding genes (N'-anti-CD40L scFv-SL335 H chain-anti-TNF-α $V_H$-C" and N'-anti-CD40L scFv-SL335 L chain-anti-TNF-α $V_L$-C") constructing the APB-B1a or APB-B1b were cloned to pD2535NT and pD2539 vectors, which are mammalian expression vectors, respectively, thereby producing recombinant pD2535NT and recombinant pD2539 vector (FIG. 13C). SAFA-based bispecific antibodies derived from ustekinumab and anifrolumab genes were cloned in the same manner as described above, thereby producing recombinant pD2535NT and recombinant pD2539 vector (data not shown).

To produce SAFA-based bispecific antibody proteins, the produced recombinant pD2535NT and recombinant pD2539 vectors, ExpiCHO cells and HD-BIOP3 GS null CHO-K1 cells were used in transient expression and stable pool production. The recombinant CHO cells were cultured in a flask for 7 to 9 days and then centrifuged, thereby acquiring culture media in 90% cell viability. In view of expression quantity in transient expression, the expression quantity of (scFv)$_2$-Fab-Fv constructs without a disulfide bond was 1.5 to 3 times higher than that of (scFv)$_2$-Fab-dsFv constructs with a disulfide bond in all of three SAFA-based bispecific antibodies derived from certolizumab, ustekinumab and anifrolumab genes. APB-B1a fragments produced with a stable pool were cultured in a flask for 7 days, yielding about 150 mg/L.

(2) Production of SAFA-Based Bispecific Antibody

For comparison of sizes and patterns of SAFA-based bispecific antibodies purified through affinity chromatography, SDS-PAGE analysis was performed under reducing and nonreducing conditions as shown in FIG. 15. Under the reducing condition, protein bands were observed at positions 60 to 75 kDa, which coincides with a theoretical size of each of heavy and light chains scFv-Fab H chain-Fv $V_H$ and (scFv-Fab L chain-Fv $V_L$) of the (scFv)$_2$-Fab-Fv and (scFv)$_2$- Fab-dsFv fragments, that is, 64 kDa (FIG. 15A), and heavy and light chain bands of (scFv)$_2$-Fab were identified at positions of 45 to 60 kDa (FIG. 15A). Meanwhile, under the nonreducing (boiled) condition, two protein bands corresponding to heavy and light chains of (scFv)$_2$-Fab-Fv without an inter-chain disulfide bond formed between the heavy and light chains were observed at positions of 60 to 75 kDa, like in the case of the reducing condition; and in the case of (scFv)$_2$-Fab-dsFv with a disulfide bond formed between its heavy and light chains, a single protein band was observed at a position of 100 to 140 kDa, falling under the range of a theoretical size 128 kDa (FIG. 15B). Under the nonreducing (not boiled) condition, in the case of (scFv)$_2$-Fab-Fv, a band was observed at a position of about 130 kDa in size, which corresponds to a sum of heavy and light chain sizes, and two protein bands for discretely positioned heavy and light chains were also unexpectedly observed at positions in the range of 60 to 75 kDa, like in the case of the nonreducing (boiled) condition (FIG. 15C). FIGS. 15A, 15B and 15C represent the results of SDS-PAGE analysis performed under the reducing, nonreducing and nonreducing (not boiled) conditions, respectively. Four SAFA-based samples, including (1) (scFv)$_2$-Fab, (2) certolizumab-related BsAb (APB-B1), (3) ustekinumab-related BsAb, (4) anifrolumab-related BsAb, were loaded onto each well in varying amounts of up to 2 μg. FIG. 15D represents size exclusion HPLC analysis for purified (scFv)$_2$-Fab-Fv (up to 25 μg) constructs. A dimer of the (scFv) 2-Fab-dsFv is indicated by an arrow. In the case of the (scFv)$_2$-Fab-dsFv construct, discretely positioned bands for heavy and light chains were not visualized, whereas two bands were observed at positions in the range of 100 to 140 kDa, and a protein band was identified at a position similar to or higher than 245 kDa presumably corresponding to a position of the (scFv)$_2$-Fab-dsFv dimer. To identify the SDS-PAGE results for the nonreducing (not boiled) condition, (scFv)$_2$-Fab-Fv and (scFv)$_2$-Fab-dsFv proteins each being under a native condition were analyzed by SE-HPLC, and the analysis results showed that the (scFv)$_2$-Fab-dsFv protein comprised a small amount of (scFv)$_2$-Fab-dsFv dimers, like in SDS-PAGE (arrow indication). In the case of (scFv)$_2$-Fab-Fv, a peak appeared only at a monomer position and the peaks corresponding to the heavy and light chains, which were identified by SDS-PAGE as being discretely positioned, were not observed (FIG. 15D). Therefore, discretely positioned heavy and light chains of the polypeptide, as indicated by the (scFv)$_2$-Fab-Fv protein sample in the SDS-PAGE experiment under the nonreducing (not boiled) condition, are considered to be observed as two bands due to partial cleavage of a non-covalent bond present between the heavy and light chains, which is caused by SDS present in the SDS-PAGE experiment or heat transferred to the protein during the experiment.

(3) Purification of SAFA-based Bispecific Antibody Protein

Figure 16A:
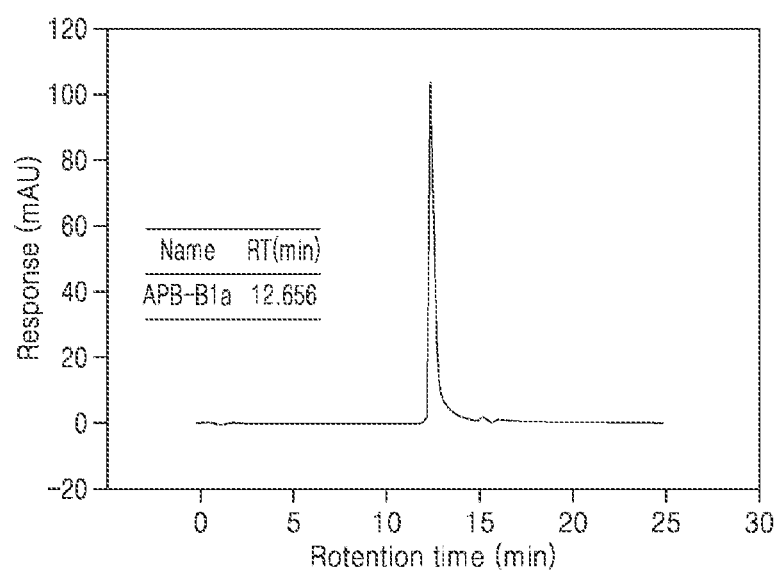
FIGS. 16A and 16B represent APB-B1 constructs, purified by 2-step chromatography.
Figure 16B:
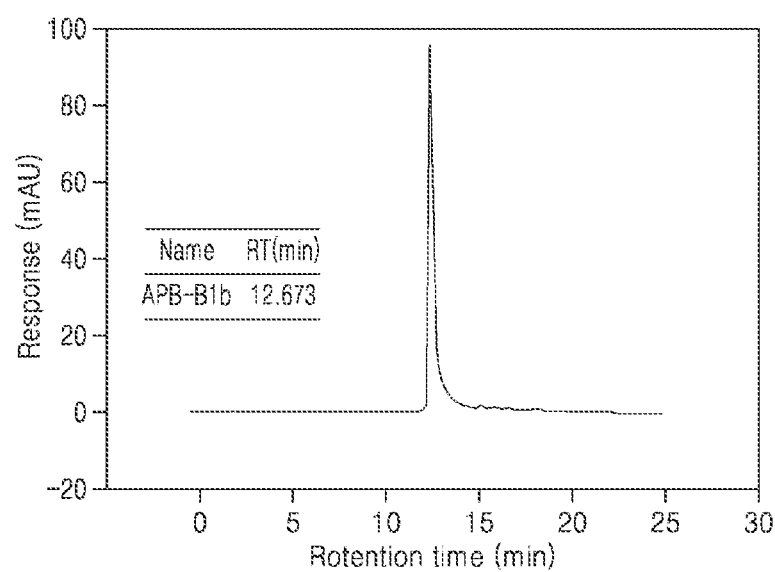

Prior to purification of APB-B1a and APB-B1b proteins isolated through affinity chromatography, the protein samples were analyzed using SDS-PAGE and SE-HPLC (FIGS. 15A to 15D). To remove proteins identified at dimer positions of APB-B1b (up to 245 kDa) (FIGS. 15C and 15D), cation exchange chromatography was performed using a CM sepharose FF resin. For the APB-B1a protein sample identified only by affinity chromatography with high purity, anion exchange chromatography was performed using a Q sepharose HP. The respective purification steps were performed using an AKTA pure 150 L system, and a final purification product was determined by SE-HPLC. The unremoved APB-B1b proteins of dimer positions, resulting after affinity chromatography, were further removed through cation exchange chromatography (FIG. 16B), and a peak was identified at a point in retention time, which is similar to that of APB-B1a (FIG. 16A). In FIGS. 16A and 16B, the SAFA-based construct was analyzed on a TSKgel UltraSW aggregation column (in 20 mM citric acid, pH 5.5 buffer) under a native condition at 280 nm. APB-B1a (a) was purified by CaptureSelect IgG-$C_{H1}$ affinity and Q sepharose HP anion exchange chromatography. APB-B1b (b) was purified by CaptureSelect IgG-$C_{H1}$ affinity and CM sepharose FF cation exchange chromatography.

Figure 17:
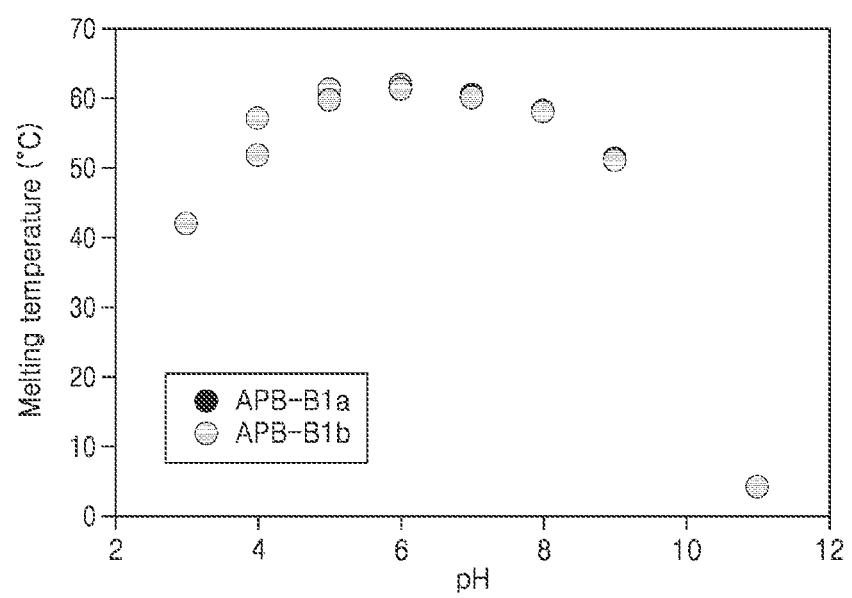
FIG. 17 represents a thermal stability shift assay under various pH and buffer conditions.

(4) Comparison of Protein Stabilities Depending on Presence of Disulfide Bond and Optimum pH Buffer for Protein Stability For comparison of stabilities of (scFv)$_2$-Fab-Fv and (scFv)$_2$-Fab-dsFv protein depending on the presence or absence of inter-chain disulfide bond of Fv, three species of SAFA-based bispecific antibodies derived from certolizumab, ustekinumab and anifrolumab genes, were gradually heat-treated from 20° C. to 90° C. in a sodium phosphate buffer (pH 7.0), and protein denaturation temperatures were measured by a real-time PCR process using a SYPRO Orange dye, coupled to hydrophobic amino acids. The result showed that the protein denaturation temperatures varied according to Fv clones of the three kinds of SAFA-base bispecific antibodies, but it was confirmed that (scFv)$_2$-Fab-Fv and (scFv)$_2$-Fab-dsFv were denatured at the same temperature regardless of the presence of disulfide bond (Table 7a). To detect an optimum buffer, which contributes to the storage stability of a APB-B1 protein, the protein denaturation temperatures were measured in the same manner as described above by thermally treating the protein at gradually increasing melting temperature ranging from 20° C. to 90° C. under the 3.0 to 11.0 pH condition (Table 7b and FIG. 17). In FIG. 17, 1 mg/mℓ of each of the purified APB-B1a and APB-B1b proteins placed in various buffers incubated at 4° C. for one day was taken and analyzed using a light cycler 480 II (RT-PCR) and a SYPRO Orange dye. As a result, under various pH conditions, the proteins demonstrated an equal denaturation temperature regardless of the presence or absence of disulfide bond in Fv. In addition, the denaturation of protein started at a relatively low temperature under conditions of low pH levels (3.0 to 4.0) and high pH levels (9.0 to 11.0). However, under the extremely acidic or basic condition, such as 3.0 or 11.0 in pH level, the denaturation of protein started at a temperature of 4° C. The pH level for the APB-B1 protein sample existing as a structure having highest stability against to heat was 5.0 to 7.0, and the APB-B1 protein exhibited highest thermal stability in all of citric acid, histidine and sodium phosphate buffers under a pH 6.0 condition (Tm=61° C.) (Table 7b).

TABLE 7a

| Buffer (pH) | Clone | Constructs | Tm (° C.) |
|---|---|---|---|
| Sodium phosphate (pH 7.0) | Certolizumab | (scFv)$_2$-Fab-dsFv | 60.3 |
| | | (scFv)$_2$-Fab-Fv | 60.5 |
| | Ustekinumab | (scFv)$_2$-Fab-dsFv | 59.9 |
| | | (scFv)$_2$-Fab-Fv | 59.2 |
| | Anifrolumab | (scFv)$_2$-Fab-dsFv | 54.8 |
| | | (scFv)$_2$-Fab-Fv | 54.8 |

TABLE 7b

| | | Tm (° C.) | |
|---|---|---|---|
| Buffer | pH | APB-B1a | APB-B1b |
| Citric acid | 3.0 | 41.82 | 41.81 |
| | 4.0 | 51.83 | 51.77 |
| | 5.0 | 61.23 | 61.06 |
| | 6.0 | 61.54 | 61.36 |
| Sodium acetate | 4.0 | 57.06 | 57.18 |
| | 5.0 | 61.15 | 61.14 |
| Histidine | 5.0 | 59.69 | 59.71 |
| | 6.0 | 61.16 | 61.19 |
| | 7.0 | 60.04 | 60.51 |
| Sodium phosphate | 6.0 | 61.84 | 61.56 |
| | 7.0 | 60.42 | 60.20 |
| | 8.0 | 58.02 | 58.13 |
| Sodium carbonate | 9.0 | 51.01 | 51.24 |
| | 11.0 | 4.00 | 4.00 |

Figure 18A:
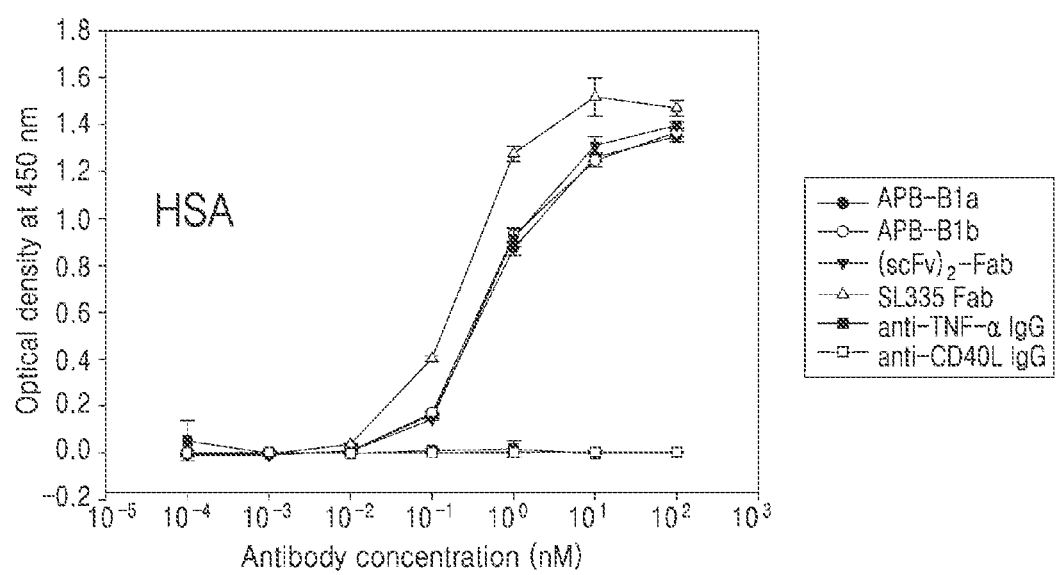
FIGS. 18A to 18C represent the determination results of the binding specificities of APB-B 1 constructs for three different antigens to be compared with parental antibodies, determined by ELISA.
Figure 18B:
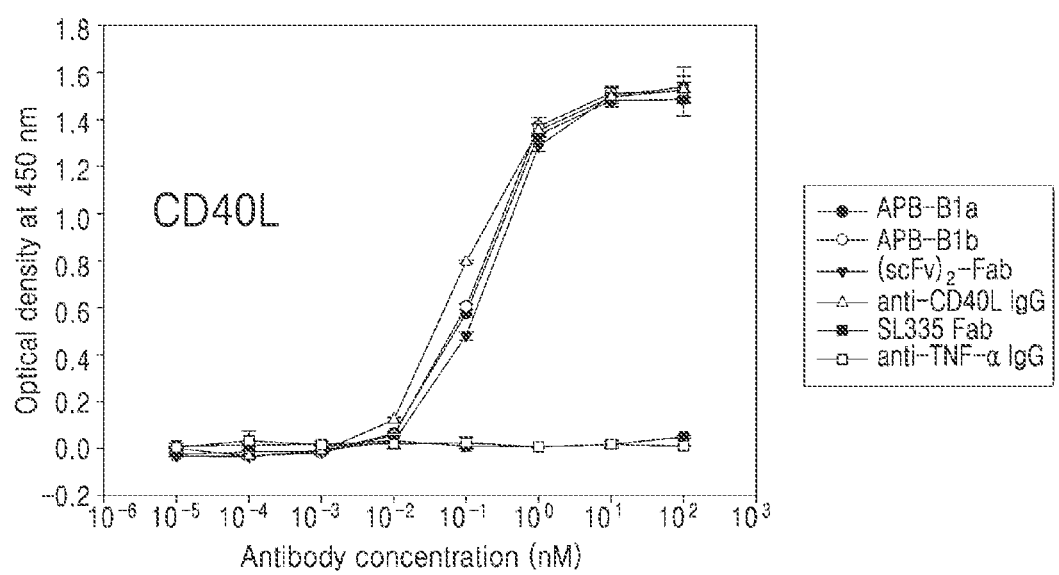
Figure 18C:
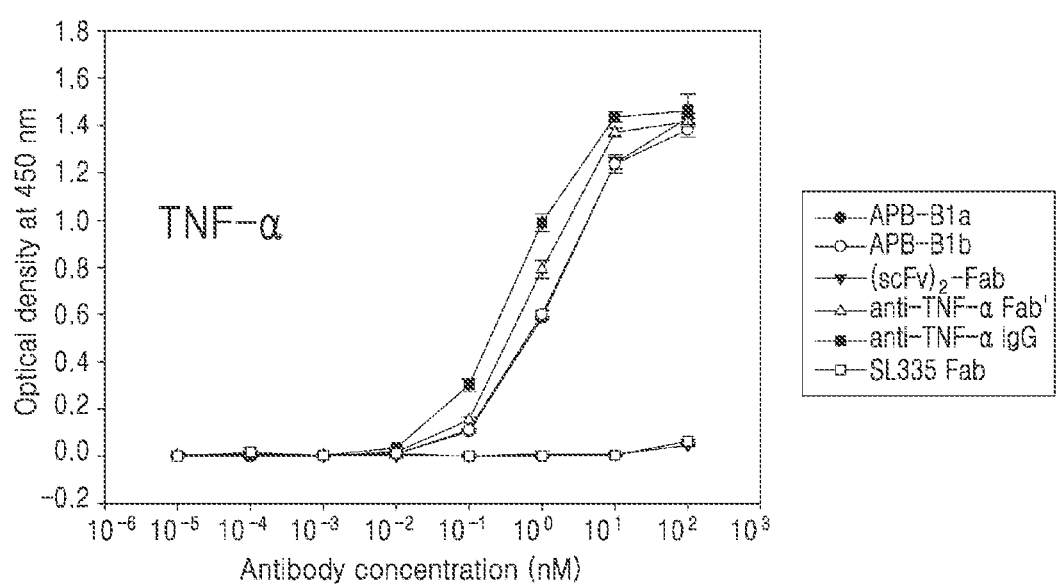

(5) Determination of Antigen Specificity and Affinity of SAFA-based Bispecific Antibody Binding affinities of purified APB-B1a and APB-B1b bispecific antibodies binding to three different antigens, that is, HSA, CD40L and TNF-α, were determined by ELISA and BLI (FIGS. 18A to 18C and Table 8). In FIGS. 18A to 18C, three target proteins, that is, human serum albumin (FIG. 18A), CD40L (FIG. 18B) and TNF-α (FIG. 18C), were coated on a 96-well MaxiSorp plate at a density of 1 µg/ml. APB-B1a, APB-B1b and parental antibody were allowed to bind to the targets at pH 7.4. HRP-conjugated goat anti-human Fd antibodies were used as secondary antibodies. Data was analyzed using an ELISA reader at 450 nm. *parental antibodies: anti-HSA Fab (SL335), anti-CD40L IgG (ruplizumab), anti-TNF-α IgG (adalimumab), and anti-TNF-α Fab (certolizumab). The ELISA result showed that the binding strength of APB-B1a or APB-B1b to human serum albumin was reduced to about 2 to 3 times compared to SL335 Fab used as a control (FIG. 18A), and in assessment of the affinity using BLI, equilibrium dissociation constants (KDs) of APBB1a, APB-B1b and SL335 Fab for human serum albumin were measured, resulting in 765 pM, 809 pM and 286 pM, respectively (Table 8). In assessment of CD40L-binding capacities of APB-B1a and APB-B1b antibodies, these two bispecific antibodies demonstrated binding capacities of about 1.5 times lower than anti-human CD40L IgG1 (ruplizumab) as a parental antibody (FIG. 18B), and binding affinities of APB-B1a, APB-B1b and parental antibody were measured, resulting in KD values of 192 pM, 167 pM and 49 pM, respectively (Table 8). The TNF-α antigen affinities of APB-B1a and APB-B1b, as measured by ELISA, were 1.5 to 2 times lower than the TNF-α antigen affinity of a parental antibody a Fab' (FIG. 18C), and binding affinities of APB-B1a, APB-B1b and parental antibody, as measured by BLI, resulted in KD values of 164 pM, 446 pM and 157 pM, respectively (Table 8), which are similar patterns to those assessed by ELISA and BLI as described above.

Figure 19:
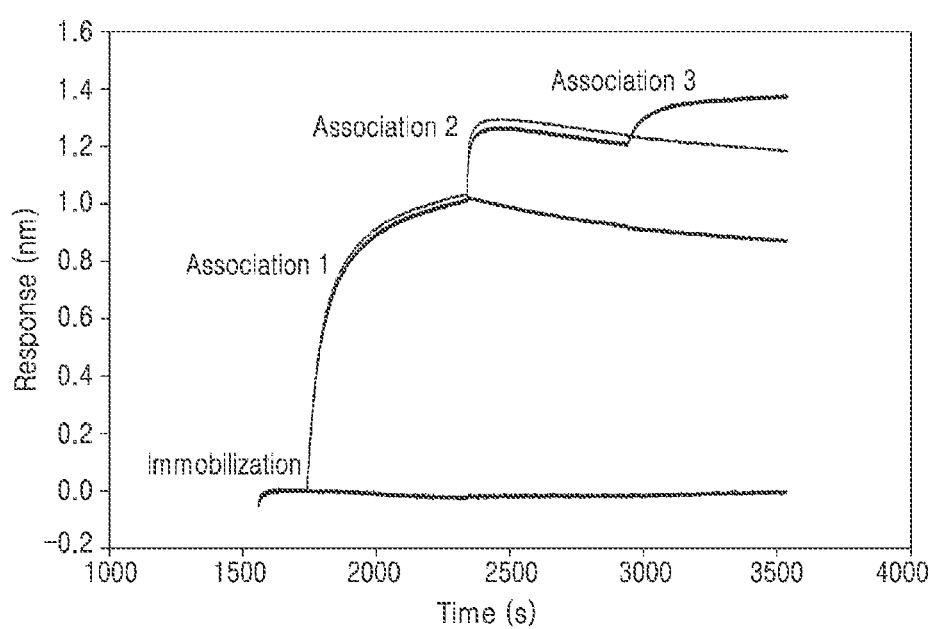
FIG. 19 represents the result of simultaneous binding of APB-B1a to three different antigens, analyzed by bio-layer interferometry.

In addition, to identify the capacity of APB-B1a simultaneously binding to three species of antigens, BLI was performed (Table 8). 500 nM CD40L was reacted in an AR2G biosensor to be immobilized on the sensor, and 25 nM APB-B1a was reacted to be associated with the immobilized CD40L. Next, human serum albumin was allowed to react with APB-1a at a concentration of up to 10 folds higher than APB-1a to allow the albumin binding site of APB-B1a to be saturated, and the identical concentration of human serum albumin was allowed to react with 50 nM TNF-α. The results are represented in FIG. 19. In FIG. 19, recombinant human CD40L was immobilized on the AR2G biosensor in a pH 5.0, 10 µg/ml sodium acetate buffer. APB-B1a was loaded at a concentration of 3.2 µg/ml (Association 1). HSA was loaded at a concentration of 13.2 µg/ml (Association 2), and HSA and TNF-α were loaded at concentrations of 13.2 µg/ml and 2 µg/ml (Association 3). Each association step was performed for 900 seconds. Data was analyzed using Octet DataAnalysis8 software.

TABLE 8

| | APB-B1a | | | APB-B1b | | | Parental antibody* | | |
|---|---|---|---|---|---|---|---|---|---|
| | $K_D$ (M) | Kon (1/Ms) | Kdis (1/s) | $K_D$ (M) | Kon (1/Ms) | Kdis (1/s) | $K_D$ (M) | Kon (1/Ms) | Kdis (1/s) |
| HSA | 7.65E−10 | 5.49E+05 | 4.20E−04 | 8.09E−10 | 5.01E+05 | 4.05E−04 | 2.86E−10 | 1.01E+06 | 2.88E−04 |
| CD40L | 1.92E−10 | 5.90E+05 | 1.13E−04 | 1.67E−10 | 5.55E+05 | 9.27E−05 | 4.96E−11 | 3.26E+05 | 1.62E−05 |
| TNF-α | 1.64E−10 | 2.30E+05 | 3.82E−05 | 4.46E−10 | 2.46E+05 | 1.09E−04 | 1.57E−10 | 4.95E+05 | 7.75E−05 |

In Table 8, binding affinities of purified APB-B1a and APB-B1b were analyzed using an Octet RED instrument. The respective antigens, HSA, CD40L and TNF-α were immobilized onto the amine reactive second-generation (AR2G) biosensor at concentrations of 20 μg/mℓ, 10 μg/mℓ and 30 μg/mℓ in a pH 5.0 sodium acetate buffer. The purified antibodies were continuously treated in a 1× kinetic buffer at pH 7.4 for two-fold dilution. Data was analyzed using Octet Data Analysis8 software. *parental antibodies: anti-HSA Fab (SL335), anti-CD40L IgG1 (ruplizumab), and anti-TNF-α Fab' (certolizumab).

(6) Binding of SAFA-Based Bispecific Antibody to Cell Membrane CD40L Protein

Figure 20:
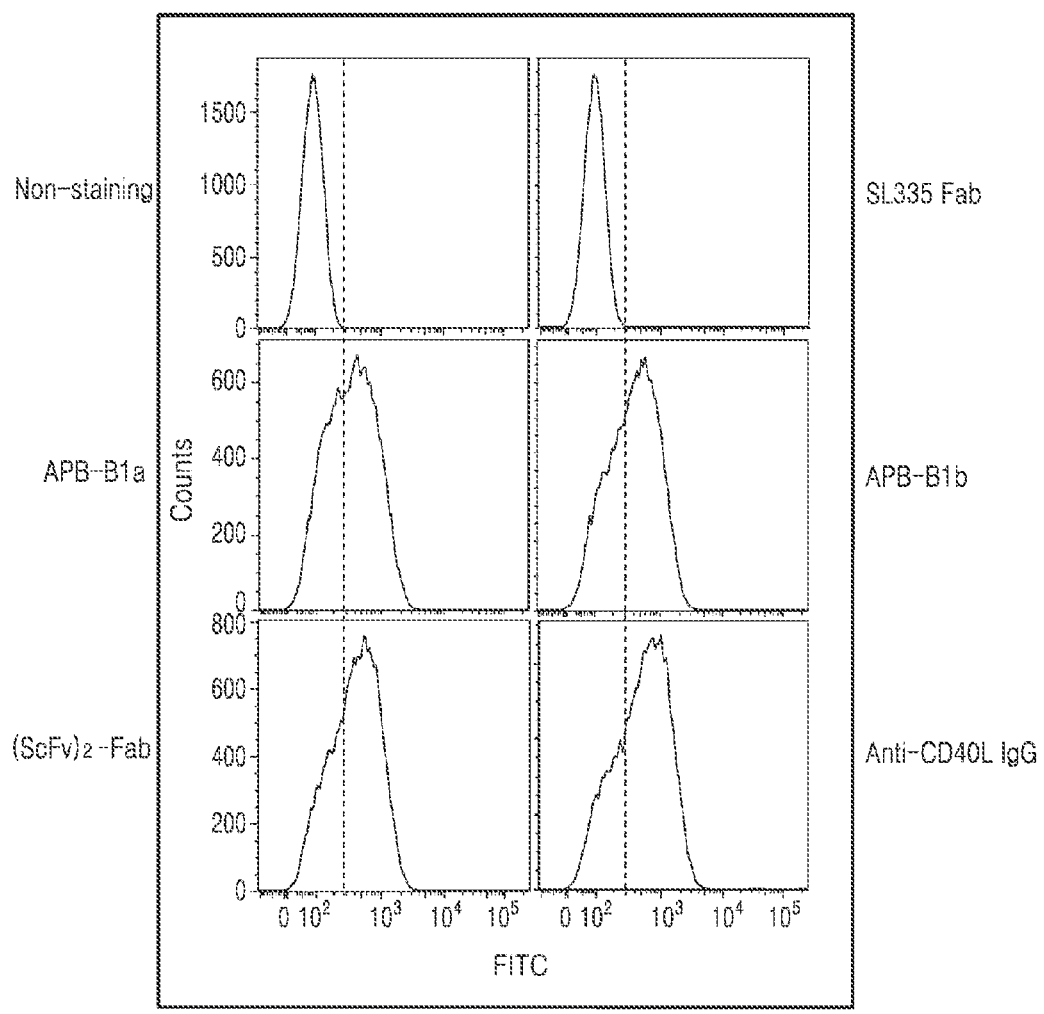
FIG. 20 represents binding of SAFA-based constructs to cellular membranes on D1.1 cells, identified by flow cytometry.

It was identified by FACSVerse whether anti-CD40L scFv of the purified SAFA-based bispecific antibody specifically would bind to a cell membrane CD40L expressed on a cell surface as well as a soluble CD40L. As a result, it was confirmed that the SAFA-based bispecific antibody was capable of binding to the cell membrane CD40L similar to anti-human CD40L IgG1 as a parental antibody (FIG. 20). In FIG. 20, D1.1 cells were prepared at concentration of $3.0 \times 10^5$ cells/reaction, an FITC-conjugated goat anti-human kappa antibody was used as a secondary antibody for detecting SL335-based construct, SL335 Fab (negative control group) and anti-CD40L IgG (positive control group). Binding signals indicated by the cell counts were measured using a FASCVerse flow cytometer.

Figure 21:
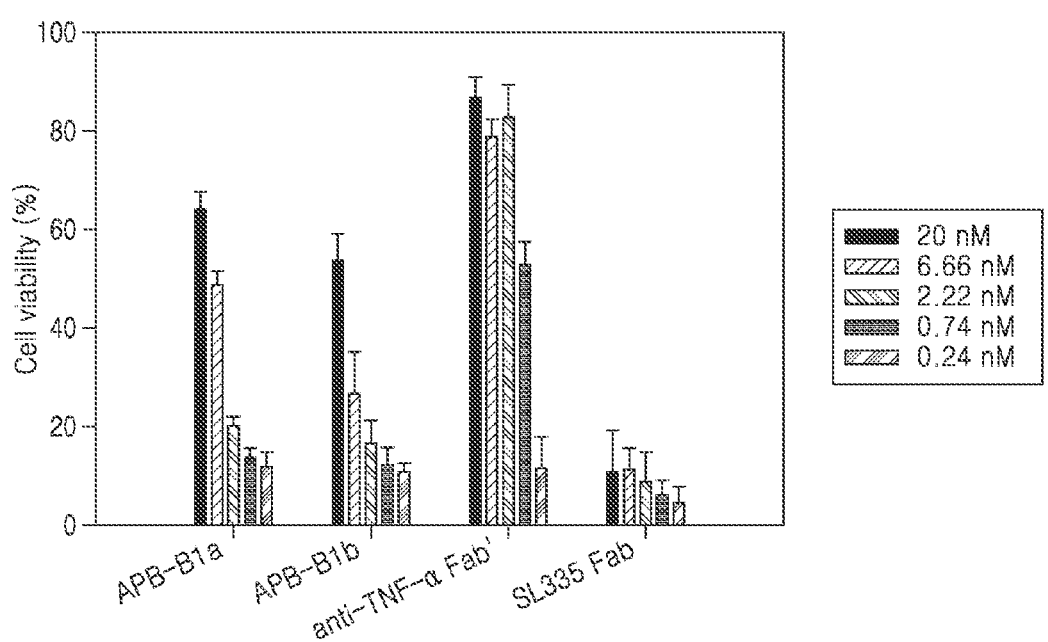
FIG. 21 represents the inhibition of TNF-α mediated cytotoxicity by SAFA-based bispecific antibodies, identified in L929 mouse cells.
Figure 22A:
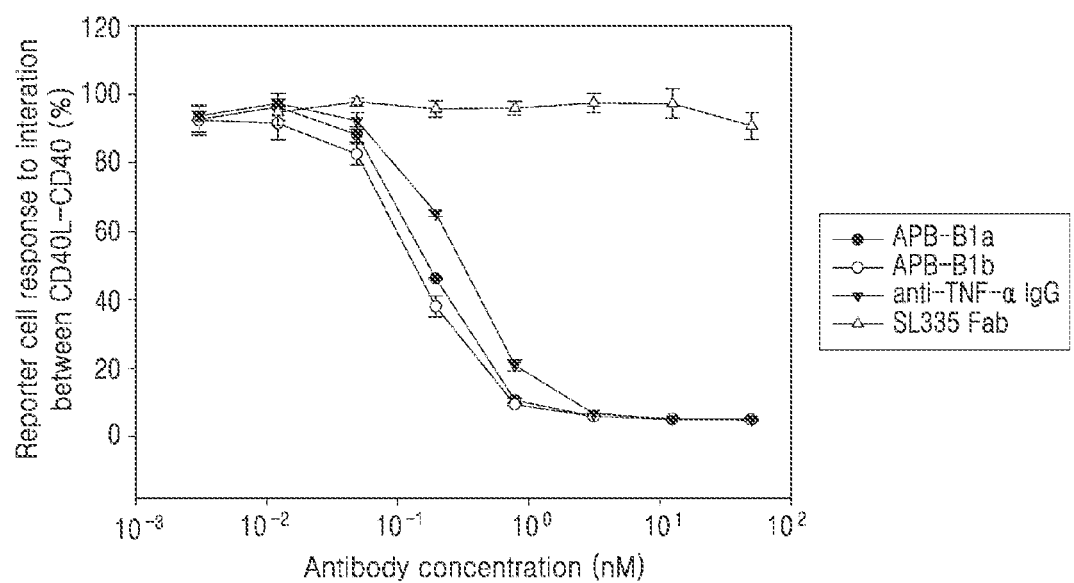
FIGS. 22A to 22C represent the determination of the capacity of APB-B1 inhibiting either or both of a CD40L-CD40 interaction and a TNFα-TNFαR interaction, identified in a HEK-Blue™ reporter cell.
Figure 22B:
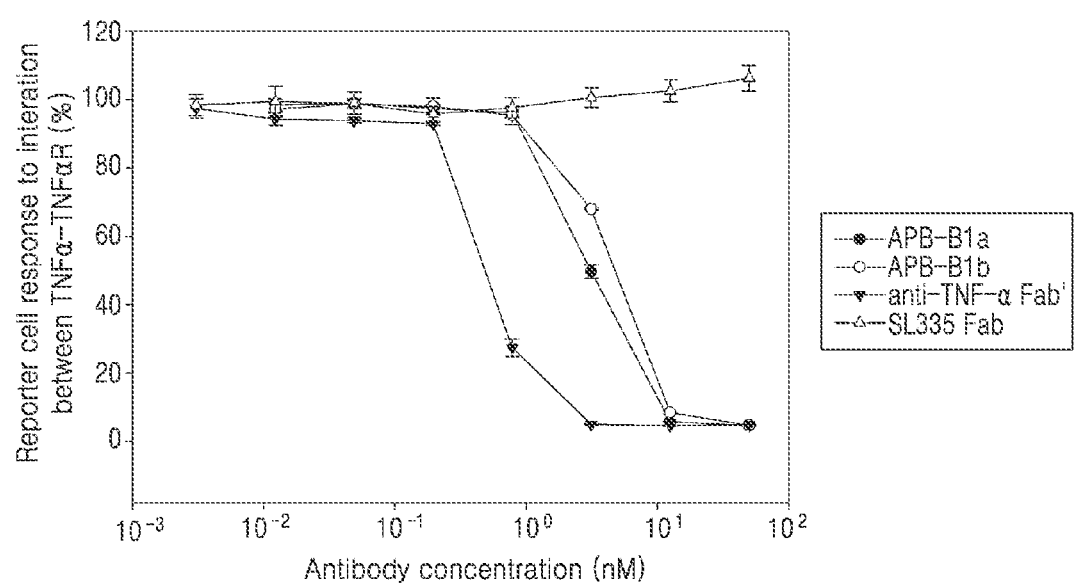
Figure 22C:
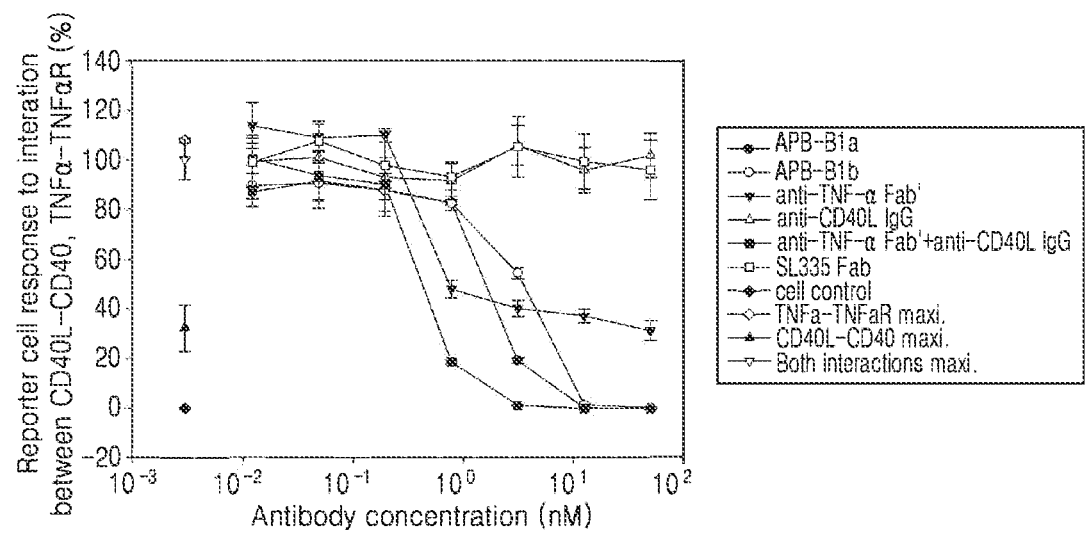

(7) Assessment of Cell-Based Inhibiting Capacity of SAFA-Based Bispecific Antibody To identify whether APB-B1a and APB-B1b are capable of inhibiting biological functions of TNF-α, in vitro inhibiting capacities were assessed using L929 mouse cells expressing cell membrane TNF receptors and exhibiting cell cytotoxicity in a TNF-α dependent manner in the presence of actinomycin D (FIG. 21). In FIG. 21, a TNF-α sample was continuously diluted 3 folds at concentrations decreasing from 20 nM to 0.24 nM and then allowed to react with L929 mouse cells expressing the TNF receptors and TNF-α (10 ng/ml) on the cell membranes in the presence of actinomycin D. An anti-TNF-α-Fab' (certolizumab) was used as a positive control group. Cell viability was measured using a cell counting kit-8. The inhibiting capacities were assessed by adding soluble TNF-α (10 ng/ml) and the serially diluted antibodies, that is, SL335 Fab, APB-B1a, APB-B1b and anti-TNFaFab' as a parental antibody. As a result, in the presence of human serum albumin (HSA), the half maximal inhibitory concentration ($IC_{50}$) value of parental antibody was 0.6259 nM, and $IC_{50}$ values of APB-B1a and APB-B1b were 5.3 nM and 12.7 nM, respectively, which are 8 to 20 times lower than the parental antibody. However, SL335 did not demonstrated inhibiting capacity (FIG. 21). Therefore, it was confirmed that APB-B1a and APB-B1b maintained their capacities of inhibiting the TNFα-TNFR interaction. To determine whether APB-B1a and APB-B1b are capable of simultaneously binding to the cell membrane CD40L expressed on the cell surface and the soluble TNF-α in the presence of human serum albumin to thus simultaneously inhibit CD40L-CD40 and TNF α-TNFR interaction pathways, the simultaneous inhibiting capacities were observed using HEK-Blue™ CD40L reporter cells that express both of the cell membrane CD40 and the cell membrane TNF receptor. In FIGS. 22A to 22C, antibody constructs for CD40L or TNF-α were continuously diluted 4 folds at concentrations from 50 nM to 0.0122 nM. Anti-CD40L IgG1 and anti-TNF-α were both used as control groups for the respective target molecules. The secreted embryonic alkaline phosphatase (SEAP) expressed by the reaction of HEK-Blue™ reporter cell with CD40L or TNF-α was measured using a QUANTI-Blue reagent, and signals were measured at A655 nm. The inhibiting capacities of APB-B1a and APB-B1 were identified by measuring HEK-Blue™ reporter cell responses to various interactions including (a) an interaction between D1.1 cell expressing CD40L and HEK-Blue™ cell expressing CD40 (FIG. 22A) and (b) an interaction between HEK-Blue™ cell expressing TNF receptor and soluble TNF-α (FIG. 22B), (c) and both interactions between D1.1 cell and HEK-Blue™ cell and between HEK-Blue™ cell and soluble TNF-α (FIG. 22C). It was identified that the $IC_{50}$ values of APB-B1a and APB-B1b for the cell membrane CD40L were 0.15 to 0.18 nM, and the $IC_{50}$ value of the parental antibody (ruplizumab, IgG1) was 0.30 nM (FIG. 22A), and the inhibiting capacities of APB-B1a and APB-B1b for the soluble TNF-α (10 ng/ml) were 3.05 nM and 4.13 nM, which are 6 to 8 times lower than the parental antibody (certolizumab, Fab'), i.e., 0.56 nm, similar to the experiments using L929 mouse cells (FIG. 22B). In the assay for simultaneously inhibiting both of the cell membrane CD40L and soluble TNF-α antigens, $IC_{50}$ values of APB-B1a and APB-B1b were 1.98 nM and 3.79 nM, which means that both of the antigens were totally (100%) inhibited by APB-B1a and APB-B1b. However, the parental antibody anti-TNF-α Fab' could inhibit only the TNF-α antigen, which means that only about 60% inhibition of total responses was achieved. In the case of the CD40L IgG1, although the CD40L IgG1 could inhibit CD40L, the anti-CD40L IgG1 could not inhibit any of the responses due to extremely high SEAP activity of the reporter cell for the uninhibited TNF-α, which is similar to a case of the SL335 Fab (negative control). Meanwhile, when two parental antibodies, anti-TNF-α Fab' and anti-CD40L IgG1, were simultaneously treated (combined treatment), the two species of targets were totally (100%) inhibited by the two parental antibodies, like in the case of the bispecific antibody, and the measured $IC_{50}$ value was 0.47 nM, which is 3 to 8 times higher than APB-B1. Consequently, notwithstanding similar inhibiting capacity levels for CD40L, it is considered that the two antibodies had lower inhibiting capacities than in the case of combined treatment due to a difference in the inhibiting capacity for TNF-α between the two antibodies (FIG. 22C).

Example 5. Additional Pharmacokinetic and Pharmacodynamics Analyses (1) PK Analysis To assess the serum half-life of APB-A1 further, pharmacokinetic analysis was performed on cynomolgus monkey models (SNBL, Japan) again. APB-A1 proteins were administered to each of the 3 cynomolgus monkeys (males) of each group at a dose of 10 mg/kg (group 1) or 30 mg/kg (group 2) through a single intravenous injection. After administration, blood samples were collected from a total of 14 time points: time point 1 prior to administration; and the following 13 time points; 0.25, 1, 6, 12 and 24 hours and 4, 8, 13, 19, 26, 33, 40 and 47 days after administration. The concentration of APB-A1 present in the serum of each cynomolgus monkey was measured by ELISA (SNBL, Japan).

(2) PD Analysis

The anti-Keyhole limpet hemocyanin (KLH) antibody response suppressed by efficacy of APB-A1 was analyzed (SNBL, Japan). A total 4 groups of samples of a vehicle (negative control group: 20 mmol/L L-histidine, HCl pH 5.8, 5% sucrose), and APB-A1 (3 mg/kg, 10 mg/kg and 30 mg/kg) were administered intravenously to cynomolgus monkeys (males; n=5/group) once every week (2 doses total). First, for induction of anti-KLH antibody responses, a first subcutaneous injection of KLH (2 mg/kg) was administered on day −28 and a second subcutaneous injection was administered on day 1 (approximately 1 hour after the end of dosing of test and control articles) for boosting. APB-A1 was injected a total of 2 times at the time of the second KLH injection (on day 1) and after a week (on day 8). The blood samples were collected prior to first KLH injection (on day −28), on days −21, −14, −7, 1 (approximately 30 minutes before test and control article dosing), 4, 8 (approximately 30 minutes before test and control article dosing), 11, 15, 22 and 29, and anti-KLH IgG and anti-KLH IgM antibody titers were measured by ELISA. For analysis of immunophenotyping in peripheral blood, the blood samples were collected a total of 6 times, prior to first KLH injection (on day −28), and on days 1 (approximately 30 minutes before test and control article dosing), 4, 11, 22 and 29. Immunophenotyping was performed using antibody panels for markers such as CD45, CD20, CD27, CD38, CD3, CD4, CD8 and Ki-67. For PK analysis, the blood samples were collected on days 1, 4, 8, 11, 15, 22, and 29 (total: 7 points). The concentration of APB-A1 present in the serum of each cynomolgus monkey was measured by ELISA. The organs to be examined immunohistochemically were trimmed on the day after necropsy and processed in an automated embedding system 2 days after gross pathology. Three sections were prepared as serial slice specimens. The first section was stained with hematoxylin-eosin (HE), and the second and third sections were used for Immunohistochemical (IHC) Examination. For IHC, the slice specimens were stained using the immunoenzyme method with the following antibodies: Mouse anti-CD20 antibody (L26, Leica Biosystems, Germany) and Mouse anti-Ki67 antibody (MIB-1, Dako Denmark A/S, Denmark). For statistical analysis, data were analyzed for homogeneity of variance by Bartlett's test. When the variance was homogeneous, Dunnett's test was performed for multiple comparisons between the control group and each test article group. When the variance was heterogeneous by Bartlett's test, a Dunnett-type test (Miller's test) was performed for multiple comparisons between the control group and each test article group.

(3) 2-Week Repeat Dose Toxicology Study

To determine the potential toxicity of APB-A1 for the treatment of autoimmune disease, when given via intravenous (slow bolus) injection on 2 occasions, 1 week apart to cynomolgus monkeys. The following parameters and end points were evaluated in this study: clinical observations, body weights, clinical pathology parameters (haematology, coagulation, clinical chemistry, and urinalysis), bioanalysis and gross necropsy findings, and organ weights.

(4) Results (1) Additional PK Study for APB-A1

Figure 23:
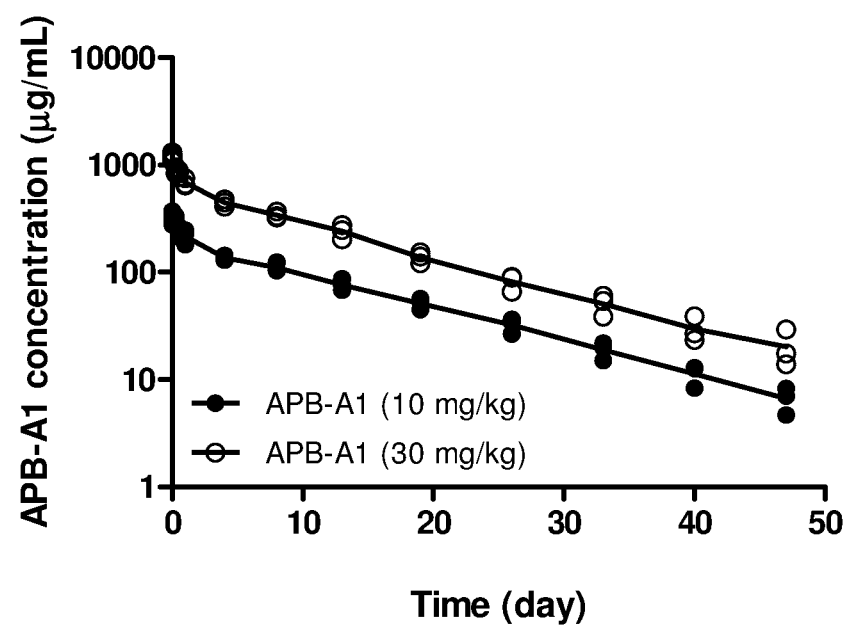
FIG. 23. Monkey P K data. The concentrations of APB-A1 in blood plasma were measured using PK ELISA. The data represents the average of the experiments conducted.

To assess the in vivo half-lives of APB-A1, pharmacokinetic assay was performed using cynomolgus monkey models (males, n=3/group). APB-A1 was administered in two dosages of 10 mg/kg and 30 mg/kg through a single intravenous injection. After collecting blood samples at the same points in time as in the Materials and Methods sections, the concentrations of APB-A1 in blood plasma were measured using PK ELISA (FIG. 23). The data represents the average of the experiments conducted. Half-lives were calculated using the data based on the ELISA result using Phoenix WinNonlin software (ver 6.4; Certara L P, Princeton, NJ, USA), and the half-lives of 10 mg/kg APB-A1 and 30 mg/kg APB-A1 were identified to be about 9.33±1.54 and 10.1±1.8 days, respectively. Cmax values were about 347 µg/mℓ and 1230 µg/mℓ at doses of 10 mg/kg and 30 mg/kg, respectively, and clearance (CL) rates were 3.48 mℓ/day/kg and 3.44 mℓ/day/kg, which were similar levels regardless of dose (Table 9).

TABLE 9

Additional Monkey PK Data

| Species | Group | Single Dose Level (mg/kg) | $T_{1/2}$ (day) | $C_{max}$ (µg/mL) | $AUC_{inf}$ (µg · day/mL) | CL (mL/day/kg) | Vdss (mL/kg) |
| --- | --- | --- | --- | --- | --- | --- | --- |
| Cynomolgus monkey | 1 | 10 | 9.33 ± 1.54 | 347 ± 24 | 2890 ± 240 | 3.48 ± 0.29 | 46.1 ± 4.7 |
| | 2 | 30 | 10.1 ± 1.8 | 1230 ± 70 | 8780 ± 880 | 3.44 ± 0.36 | 43.6 ± 3.5 |

(2) Additional PD Study for APB-A1

Figure 24A:
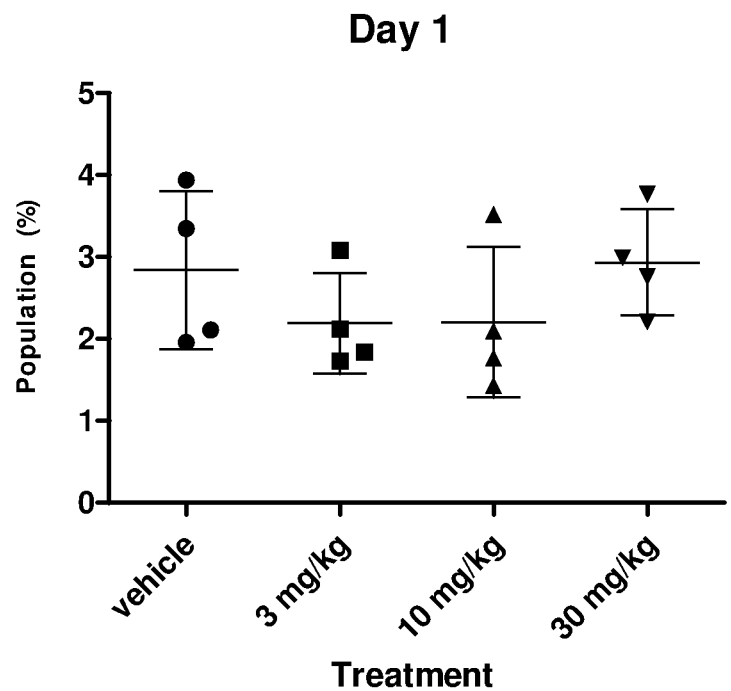
FIGS. 24A and 24B. Immunophenotyping (dividing B cells). In immunophenotyping in peripheral blood, decreased dividing B cells were noted in the 30, 10, and/or 3 mg/kg groups in comparison with those in the control group at Day 1 (FIG. 24A) and Day 11 (FIG. 24B).
Figure 24B:
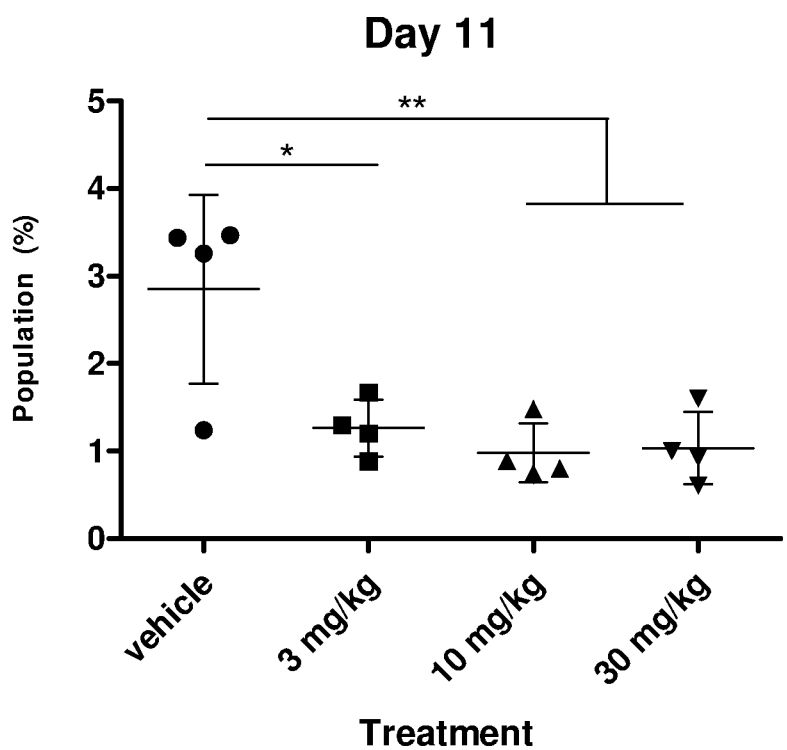
Figure 25:
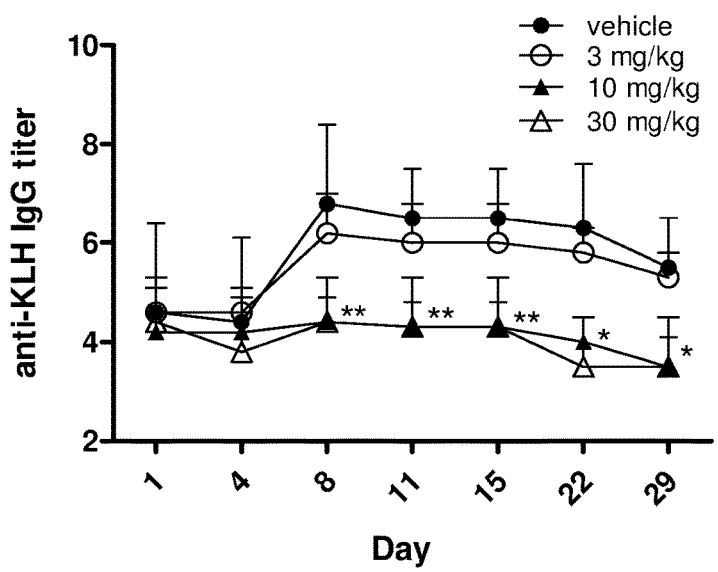
FIG. 25. Titer of anti-KLH IgG in serum. In anti-KLH antibody measurement, decreased IgG antibody titer was noted from Day 8 to 29 in the 10 and 30 mg/kg groups in comparison with those in the control group (*P<0.05, **P<0.01: significantly different from control).
Figure 26:
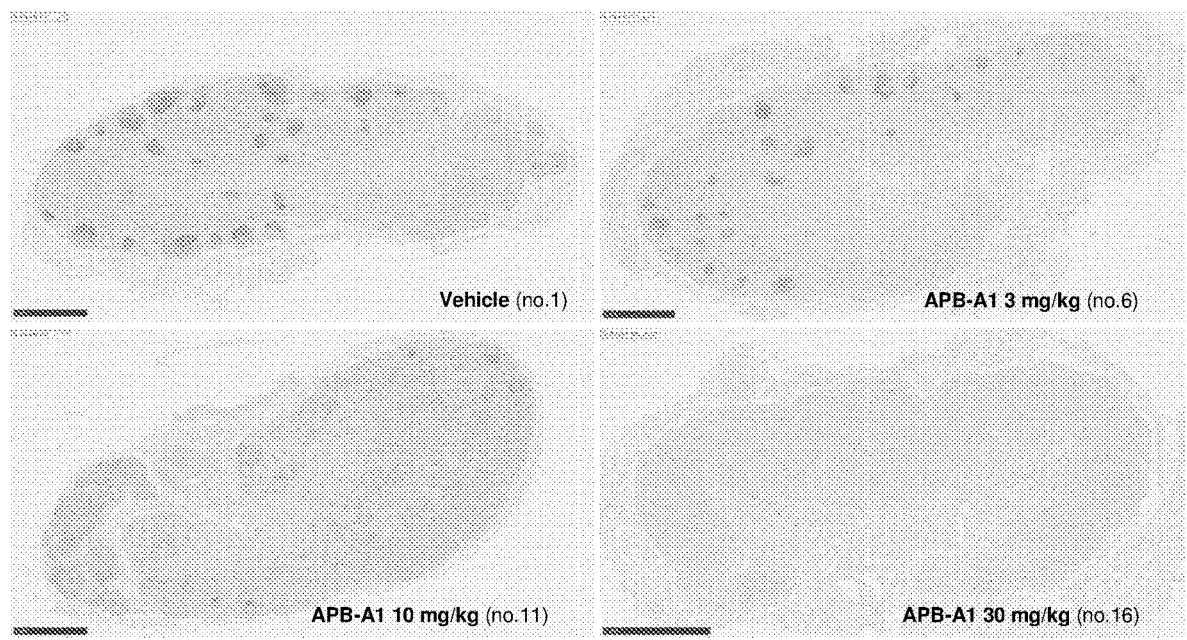
FIG. 26. Ki67 positive cell of axillary lymph node (immunohistochemical examination). In histopathology and immunohistochemical examination, on Day 29, decreased anti-Ki67 positive cell of the germinal center in the axillary lymph nodes were observed in the 10 and/or 30 mg/kg group.
Figure 27:
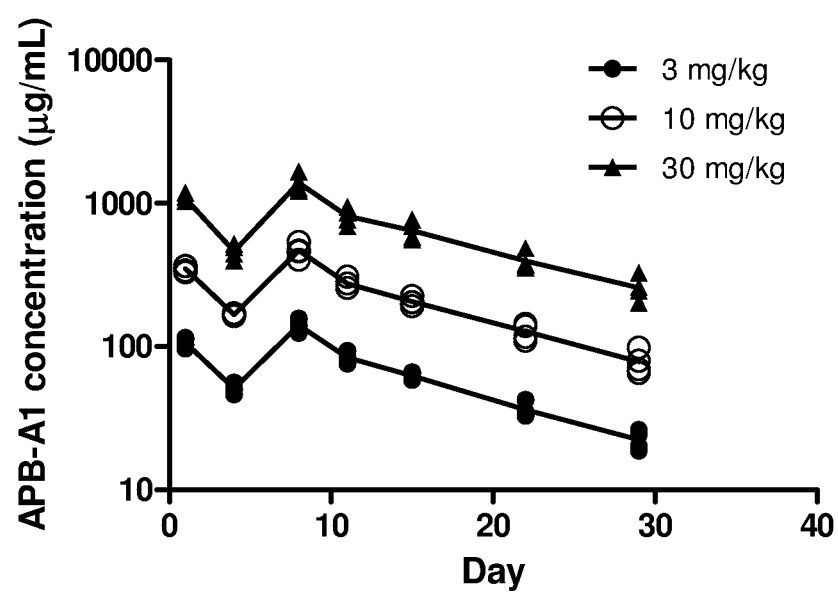
FIG. 27. Concentration of APB-A1 in serum in PD study. In PK, the Cmax and AUC0-t values increased almost dose-proportionally between 3 and 30 mg/kg group in the first and second dosing.

No animal was found dead or euthanized due to moribundity in any group. No test article-related changes were noted in clinical signs, body weight, or gross pathology in any group. In immunophenotyping in peripheral blood, decreased dividing B cells were noted in the 30, 10, and/or 3 mg/kg groups in comparison with those in the control group (FIGS. 24A and 24B). In anti-KLH antibody measurement, decreased IgG antibody titer was noted from Day 8 to 29 in the 10 and 30 mg/kg groups in comparison with those in the control group (*P<0.05, **P<0.01: significantly different from control) (FIG. 25) while no test article-related changes were noted in IgM antibody titer (Data not shown). In histopathology and immunohistochemical examination, on Day 29, decreased cellularity, anti-CD20 positive cell, and anti-Ki67 positive cell of the germinal center in the axillary and submandibular lymph nodes were observed in the 10 and/or 30 mg/kg group (FIG. 26) and Table 10). In PK, the Cmax and AUC0-t values increased almost dose-proportionally between 3 and 30 mg/kg group in the first and second dosing (FIG. 27 and Table 11).

TABLE 10

Histopathology & Immunohistochemical examination
Histopathology & Immunohistochemical examination (Day 29)

| | | | Group | | | | | | | | | | | | | | | |
|---|---|---|---|---|---|---|---|---|---|---|---|---|---|---|---|---|---|---|
| | | | Vehicle | | | | | APB-A1 | | | | | | | | | | |
| | | | Dose | | | | | | | | | | | | | | | |
| | | | 0 | | | | | 3 mg/kg | | | 10 mg/kg | | | | 30 mg/kg | | | |
| | | | Animal No. | | | | | | | | | | | | | | | |
| | | | 1 | 2 | 3 | 4 | 6 | 8 | 9 | 10 | 11 | 12 | 13 | 15 | 16 | 17 | 18 | 20 |
| Decrease, Germinal center | Lymph nodes, axillary | cellularity | – | – | – | – | – | – | – | – | ± | ± | ± | ± | 2+ | + | 2+ | ± |
| | | CD20+ cell | – | – | – | – | – | – | – | – | – | – | ± | ± | 2+ | ± | 2+ | – |
| | | Ki67+ cell | – | – | – | – | – | – | – | – | ± | ± | ± | ± | 2+ | + | 2+ | ± |
| | Lymph nodes, Inguinal | cellularity | – | – | – | – | – | – | – | – | – | – | – | – | – | – | – | – |
| | | CD20+ cell | – | – | – | – | – | – | – | – | – | – | – | – | – | – | – | – |
| | | Ki67+ cell | – | – | – | – | – | – | – | – | – | – | – | – | – | – | – | – |
| | Lymph nodes, submandibular | cellularity | – | – | – | – | – | – | – | – | – | – | – | – | – | – | – | – |
| | | CD20+ cell | – | – | – | – | – | – | – | – | – | – | – | – | ± | ± | ± | – |
| | | Ki67+ cell | – | – | – | – | – | – | – | – | – | – | – | – | + | + | + | ± |

–: No abnormal changes
±: Very slight
+: Slight
2+: Moderate
3+: Marked

TABLE 11

PK results in PD study

| Dose level (mg/kg) | 3 | 10 | 30 |
|---|---|---|---|
| First dosing | | | |
| Cmax (μg/mL) | 112 ± 14 | 355 ± 20 | 1080 ± 70 |
| AUC0-t (μg · day/mL) | 377 ± 48 | 1190 ± 60 | 3560 ± 200 |
| Second dosing | | | |
| Cmax (μg/mL) | 141 ± 13 | 469 ± 55 | 1390 ± 200 |
| AUC0-t (μg · day/mL) | 3990 ± 400 | 13700 ± 2200 | 40900 ± 6300 |

2-Week Repeat Dose Toxicology Study

There were no premature decedents, clinical observations or changes in body weight, haematology, coagulation, clinical chemistry or urinalysis, nor any gross findings noted in the males and females receiving APB-A1. Administration of APB-A1 by intravenous (slow bolus) injection on 2 occasions, 1 week apart was well tolerated in cynomolgus monkeys at dose levels of up to 100 mg/kg/dose.

In the present disclosure, it has been verified that a new format of multispecific antibody construct could be successfully produced based on the existing technique of a bispecific antibody having increased in vivo sustainability, which was developed by the present inventors. Particularly, the multispecific antibody, which is capable of binding to CD40L, TNF-α or other bioactive effectors, can be usefully applied as therapeutic agents for various autoimmune diseases.

The foregoing description of the specific embodiments will so fully reveal the general nature of the invention that others can, by applying knowledge within the skill of the art, readily modify and/or adapt for various applications, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be herein incorporated by reference.

INDUSTRIAL APPLICABILITY

The multispecific antibody of the present disclosure can be used in development of an autoimmune disease therapeutic agent having extended in vivo retention time, while reducing a side effect, such as thromboembolism.

SEQUENCE LISTING

```
Sequence total quantity: 107
SEQ ID NO: 1            moltype = DNA  length = 669
FEATURE                 Location/Qualifiers
misc_feature            1..669
                        note = SL335 Heavy chain DNA
source                  1..669
                        mol_type = other DNA
                        organism = synthetic construct
```

-continued

```
SEQUENCE: 1
caggtgcagc ttgtccagtc cggaggcggc cctgtgaagc ctgggggtc  attgagattg    60
tcctgtgcag catccggatt tatgttcagg gcttactcca tgaactgggt gcgccaggct   120
ccagggaagg ggttggaatg ggtgtccagc atcagcagct ctggaaggta catccactac   180
gccgactccg tgaagggcag gttcaccatt tcccgggaca acgctaagaa cagcctgtac   240
ctccagatga actccctccg ggctgaggac accgccgtgt actactgcgc ccggggagaca  300
gtgatggccg ggaaagccct ggattactgg ggccaaggca ctctggtcac agtcagctca   360
gcctctacaa aaggccctag tgtgtttcct ctggccccat caagtaagag cacctcagag   420
gggaccgccg ccctgggctg cctggtcaaa gattactttc cagagcccgt gacagtgagt   480
tggaacagtg gggctctgac aagcggggtc catacattcc ccgccgtgct gcagagcagc   540
gggctgtata gcctgagcag cgtcgtcact gtgcccagct cttctctcgg cacacagact   600
tacatttgca atgtgaacca caagcccagc aacactaagg tcgataagaa ggtggagccc   660
aagtcctcc                                                           669

SEQ ID NO: 2            moltype = DNA  length = 645
FEATURE                 Location/Qualifiers
misc_feature            1..645
                        note = SL335 Light chain DNA
source                  1..645
                        mol_type = other DNA
                        organism = synthetic construct
SEQUENCE: 2
gacatcgtcc tgacccagag ccccgggaca ctgagcctgt ccccggggga gacagccaca    60
ctgagctgca gggccagcca gtccgtcggc tccaacctgg cctggtacca gcagaagcca   120
gggcaggccc ccaggctgct gatttacggc gccagcacag cgccacagg  ggtgcccgcc   180
aggtttagcg gcagcggagc cggcacagat tttacactga caatcacatc cctgcagccc   240
gaggattttg ccacatacta ctgccagcag tactactcct tcctggccaa gacattcggc   300
cagggcaccc agctggagat caagcggacc gtggccgccc cagcgtgtt  tatttttccc   360
ccagcgatg agcagctgaa gtccggcacc gcctccgtcg tgtgcctgct gaacaacttc   420
tacccccggg aggccaaggt ccagtggaag gtcgataacg ccctgcagag cgggaactcc   480
caggagtccg tgaccgagca ggactccaag gacagcacct actccctgtc caacacccctg  540
accctgagca aggccgacta cgagaagcac aaggtctacg cctgcgaggt gacccaccag   600
ggcctgtcct cccccgtgac caagagcttt aaccgggggg agtcc                   645

SEQ ID NO: 3            moltype = AA  length = 15
FEATURE                 Location/Qualifiers
REGION                  1..15
                        note = linker 1
source                  1..15
                        mol_type = protein
                        organism = synthetic construct
SEQUENCE: 3
GGGGSGGGGS GGGGS                                                     15

SEQ ID NO: 4            moltype = AA  length = 18
FEATURE                 Location/Qualifiers
REGION                  1..18
                        note = linker 2
source                  1..18
                        mol_type = protein
                        organism = synthetic construct
SEQUENCE: 4
GSTSGSGKPG SGEGSTKG                                                  18

SEQ ID NO: 5            moltype = DNA  length = 794
FEATURE                 Location/Qualifiers
misc_feature            1..794
                        note = hu5c8 scFv DNA
source                  1..794
                        mol_type = other DNA
                        organism = synthetic construct
SEQUENCE: 5
atggagtggt cctgggtctt cctcttcttc ctcagcgtga ccaccggagt gctttccgac    60
atcgtcttga ctcaatctcc cgccaccctg tccgtatccc ccggagagcg tgctacaata   120
agttgccgcg caagtcagag agtgtcaagc agtacatact cctacatgca ctggtaccag   180
cagaagccag gccagcctcc aaagttgctt attaaatacg ccagcaatct tgaatccgga   240
gtaccgcccc gcttctcagg atctggttct ggcacagatt ttacactcac aattagctct   300
gtcgagcctg aggacttcgc cacctattac tgccagcact cctgggagat ccccctaca   360
ttcggtcagg gactaaaact tgagataaag cggggaggcg gaggaagtgg ggtggagga   420
agcggcggag ggggagcca  ggtccagctg gtgcagagtc gcgcagaagt agtaaagccc   480
ggcgcatcgg ttaagctgtc ctgtaaagca agcggatata ttttcaccctc ctattacatg   540
tattgggtga acaagcacc  aggccaagga cttaatgga tcggcgaaat aaatcccagc   600
aacggcgata caatttttaa tgagaagttt aagtctaaag ccacattgac tgttgataaa   660
tccgccagca ctgcatatat ggaactctct agcttgagga gtgaagatac cgcagtgtac   720
tactgcactc gtagtgatgg caggaatgac atggactctt ggggccaggg tacattggtt   780
acagtctcct cttg                                                     794
```

```
SEQ ID NO: 6              moltype = DNA  length = 354
FEATURE                   Location/Qualifiers
misc_feature              1..354
                          note = anti-TNF-alpha Fv, VH DNA
source                    1..354
                          mol_type = other DNA
                          organism = synthetic construct
SEQUENCE: 6
gaagtccaac ttgttgagtc cggaggaggg ctcgttcaac caggcgggtc cctgcggctt   60
tcctgtgctg cttcaggcta cgttttaca gattacggca tgaactgggt tcggcaggcc  120
cccggtaaag gtctggaatg gatggggtgg atcaatacat acataggtga acccatatat  180
gcagattcag taaagggtcg cttcacattt tctctcgaca ctagtaagtc aacagcctac  240
ctccagatga actcccttcg tgcagaggat acagctgtgt attactgcgc ccgggggttac  300
agaagctacg caatggatta ttggggggcag ggtacccttg ttaccgtctc aagt        354

SEQ ID NO: 7              moltype = DNA  length = 324
FEATURE                   Location/Qualifiers
misc_feature              1..324
                          note = anti-TNF-alpha Fv, VL DNA
source                    1..324
                          mol_type = other DNA
                          organism = synthetic construct
SEQUENCE: 7
gatatacaga tgacacaaag cccaagcagt ctcagtgctt ccgttggtga ccgggtcacc   60
atcacttgta aagcatccca gaacgtcgga acaaacgtag catggtacca acagaagcca  120
ggaaaggcac caaaggccct tatctactcc gcttcctttc tctactcagg cgtaccatac  180
aggttcagcg gctccggcag tggaaccgat ttcacccta ctatttcctc actgcagcca  240
gaggacttcg ccacttacta ctgtcaacag tataatttt acccccctgac atttggacag  300
ggaacaaaag ttgagattaa gcgg                                         324

SEQ ID NO: 8              moltype = DNA  length = 354
FEATURE                   Location/Qualifiers
misc_feature              1..354
                          note = anti-TNF-alpha dsFv, VH DNA
source                    1..354
                          mol_type = other DNA
                          organism = synthetic construct
SEQUENCE: 8
gaagtccaac ttgttgagtc cggaggaggg ctcgttcaac caggcgggtc cctgcggctt   60
tcctgtgctg cttcaggcta cgttttaca gattacggca tgaactgggt tcggcaggcc  120
cccggtaaat gtctggaatg gatggggtgg atcaatacat acataggtga acccatatat  180
gcagattcag taaagggtcg cttcacattt tctctcgaca ctagtaagtc aacagcctac  240
ctccagatga actcccttcg tgcagaggat acagctgtgt attactgcgc ccgggggttac  300
agaagctacg caatggatta ttggggggcag ggtacccttg ttaccgtctc aagt        354

SEQ ID NO: 9              moltype = DNA  length = 324
FEATURE                   Location/Qualifiers
misc_feature              1..324
                          note = anti-TNF-alpha dsFv, VL DNA
source                    1..324
                          mol_type = other DNA
                          organism = synthetic construct
SEQUENCE: 9
gatatacaga tgacacaaag cccaagcagt ctcagtgctt ccgttggtga ccgggtcacc   60
atcacttgta aagcatccca gaacgtcgga acaaacgtag catggtacca acagaagcca  120
ggaaaggcac caaaggccct tatctactcc gcttcctttc tctactcagg cgtaccatac  180
aggttcagcg gctccggcag tggaaccgat ttcacccta ctatttcctc actgcagcca  240
gaggacttcg ccacttacta ctgtcaacag tataatttt acccccctgac atttggatgt  300
ggaacaaaag ttgagattaa gcgg                                         324

SEQ ID NO: 10             moltype = DNA  length = 357
FEATURE                   Location/Qualifiers
misc_feature              1..357
                          note = anti-IL-23 Fv, VH DNA
source                    1..357
                          mol_type = other DNA
                          organism = synthetic construct
SEQUENCE: 10
gaggtacagc ttgtccaaag tggcgccgag gtcaaaaaac ccggagaaag tctgaaaatt   60
agttgcaaag ctccggcta ctccttcaca acttattggc ttgggtgggt acggcagatg  120
cccggaaaag gcctcgattg gataggggata atgagtcccg tagacagtga catccgctac  180
agcccttctt ttcaaggtca agttacaatg agtgttgaca aatccatcac tacagcatac  240
cttcagtgga cagcctgaa ggcaagcgat actgcaatgt attactgtgc ccgtcgccgc  300
cccgggcagg gctatttcga cttctggggc caggggacac tggtcaccgt ttcatct     357
```

```
SEQ ID NO: 11              moltype = DNA   length = 324
FEATURE                    Location/Qualifiers
misc_feature               1..324
                           note = anti-IL-23 Fv, VL DNA
source                     1..324
                           mol_type = other DNA
                           organism = synthetic construct
SEQUENCE: 11
gacatccaaa tgacacagag tccatctagc ctgagcgcct cagttggcga ccgggtaaca   60
ataacctgcc gggccagtca ggggataagc tcatggctgg catggtatca gcaaaaaccc  120
gaaaaagcac ctaaatcact tatctatgcc gctagcagct tgcaatctgg tgtaccctca  180
cgttttttctg ggagtggtag cggcacagat ttcacactca caatttcctc ccttcagccc  240
gaagatttcg ctacctacta ttgccaacag tataacattt atccttatac attcgggcaa  300
ggaacaaaat tggagataaa gcgg                                         324

SEQ ID NO: 12              moltype = DNA   length = 357
FEATURE                    Location/Qualifiers
misc_feature               1..357
                           note = anti-IL-23 dsFv, VH DNA
source                     1..357
                           mol_type = other DNA
                           organism = synthetic construct
SEQUENCE: 12
gaggtacagc ttgtccaaag tggcgccgag gtcaaaaaac ccggagaaag tctgaaaatt   60
agttgcaaag gctccggcta ctccttcaca acttattggc ttgggtgggt acggcagatg  120
cccggaaaat gtctcgattg gataggggata atgagtcccg tagacagtga catccgctac  180
agccttctt ttcaaggtca agttacaatg agtgttgaca aatccatcac tacagcatac  240
cttcagtgga acagcctgaa ggcaagcgat actgcaatgt attactgtgc ccgtcgccgc  300
cccgggcagg gctatttcga cttctggggc caggggacac tggtcaccgt ttcatct    357

SEQ ID NO: 13              moltype = DNA   length = 324
FEATURE                    Location/Qualifiers
misc_feature               1..324
                           note = anti-IL-23 dsFv, VL DNA
source                     1..324
                           mol_type = other DNA
                           organism = synthetic construct
SEQUENCE: 13
gacatccaaa tgacacagag tccatctagc ctgagcgcct cagttggcga ccgggtaaca   60
ataacctgcc gggccagtca ggggataagc tcatggctgg catggtatca gcaaaaaccc  120
gaaaaagcac ctaaatcact tatctatgcc gctagcagct tgcaatctgg tgtaccctca  180
cgttttttctg ggagtggtag cggcacagat ttcacactca caatttcctc ccttcagccc  240
gaagatttcg ctacctacta ttgccaacag tataacattt atccttatac attcgggtgt  300
ggaacaaaat tggagataaa gcgg                                         324

SEQ ID NO: 14              moltype = DNA   length = 351
FEATURE                    Location/Qualifiers
misc_feature               1..351
                           note = anti-IFNAR1 Fv, VH DNA
source                     1..351
                           mol_type = other DNA
                           organism = synthetic construct
SEQUENCE: 14
gaagttcagc tggtacaatc aggagccgaa gtaaagaagc caggcgaatc ccttaaaatc   60
tcttgcaagg gaagcggcta catatttact aattactgga tcgcatgggt tcgacagatg  120
ccaggcaaag gtctggagtc catggggata atataccctg agacagtgaa catacgctat  180
tccccaagtt tccaaggaca agtgaccatt tctgctgata aaagcatcac aacagcctac  240
cttcaatggt catctcttaa ggcctctgac accgcaatgt actactgtgc tcgccacgat  300
attgaggggt tcgattactg ggggcgggc accccttgtta cagttagcag t           351

SEQ ID NO: 15              moltype = DNA   length = 327
FEATURE                    Location/Qualifiers
misc_feature               1..327
                           note = anti-IFNAR1 Fv, VL DNA
source                     1..327
                           mol_type = other DNA
                           organism = synthetic construct
SEQUENCE: 15
gagattgtac ttacccagtc tcctggcact ctgagtttga gtcccggcga gcgcgctacc   60
ctgagttgcc gagcttcaca gtccgtcagc tcttccattct tcgcttggta ccagcaaaaa  120
cctgggcagg cccccaagatt gcttatatat ggagcctcct cccagcaac aggcatcccc  180
gaccgactca gcgggttctgg atctggcacc gatttcactc tgacaattac ccggcttgag  240
cccgaggact ttgccgtata ttattgtcaa caatacgata gcagcgcaat tactttcggg  300
caagggactc gacttgagat taaacgt                                      327
```

```
SEQ ID NO: 16              moltype = DNA  length = 37
FEATURE                    Location/Qualifiers
misc_feature               1..37
                           note = forward primer APB-A1 H DNA
source                     1..37
                           mol_type = other DNA
                           organism = synthetic construct
SEQUENCE: 16
gatcaactct agagccacca tggagtggtc ctgggtc                                37

SEQ ID NO: 17              moltype = DNA  length = 56
FEATURE                    Location/Qualifiers
misc_feature               1..56
                           note = reverse primer APB-A1 H DNA
source                     1..56
                           mol_type = other DNA
                           organism = synthetic construct
SEQUENCE: 17
aggaagacgc ttttagaggc ggccgctcag gaggacttgg gctccacctt cttatc           56

SEQ ID NO: 18              moltype = DNA  length = 37
FEATURE                    Location/Qualifiers
misc_feature               1..37
                           note = forward primer APB-A1 L DNA
source                     1..37
                           mol_type = other DNA
                           organism = synthetic construct
SEQUENCE: 18
gatcaactct agagccacca tggagaccca cagccag                                37

SEQ ID NO: 19              moltype = DNA  length = 59
FEATURE                    Location/Qualifiers
misc_feature               1..59
                           note = reverse primer APB-A1 L DNA
source                     1..59
                           mol_type = other DNA
                           organism = synthetic construct
SEQUENCE: 19
aggaagacgc ttttagaggc ggccgctcag gactcccccc ggttaaagct cttggtcac        59

SEQ ID NO: 20              moltype = DNA  length = 36
FEATURE                    Location/Qualifiers
misc_feature               1..36
                           note = primer 1
source                     1..36
                           mol_type = other DNA
                           organism = synthetic construct
SEQUENCE: 20
gatcaactct agagccacca tggagtggtc ctgggt                                 36

SEQ ID NO: 21              moltype = DNA  length = 30
FEATURE                    Location/Qualifiers
misc_feature               1..30
                           note = primer 2
source                     1..30
                           mol_type = other DNA
                           organism = synthetic construct
SEQUENCE: 21
ggaggacttg ggctccacct tcttatcgac                                        30

SEQ ID NO: 22              moltype = DNA  length = 30
FEATURE                    Location/Qualifiers
misc_feature               1..30
                           note = primer 3
source                     1..30
                           mol_type = other DNA
                           organism = synthetic construct
SEQUENCE: 22
gtcgataaga aggtggagcc caagtcctcc                                        30

SEQ ID NO: 23              moltype = DNA  length = 30
FEATURE                    Location/Qualifiers
misc_feature               1..30
                           note = primer 4
source                     1..30
                           mol_type = other DNA
                           organism = synthetic construct
```

```
SEQUENCE: 23
atcggcggcc gcgaagacgc ttttagatca                                                30

SEQ ID NO: 24           moltype = DNA   length = 37
FEATURE                 Location/Qualifiers
misc_feature            1..37
                        note = primer 5
source                  1..37
                        mol_type = other DNA
                        organism = synthetic construct
SEQUENCE: 24
gatcaactct agagccacca tggagaccca cagccag                                        37

SEQ ID NO: 25           moltype = DNA   length = 30
FEATURE                 Location/Qualifiers
misc_feature            1..30
                        note = primer 6
source                  1..30
                        mol_type = other DNA
                        organism = synthetic construct
SEQUENCE: 25
ggactccccc cggttaaagc tcttggtcac                                                30

SEQ ID NO: 26           moltype = DNA   length = 30
FEATURE                 Location/Qualifiers
misc_feature            1..30
                        note = primer 7
source                  1..30
                        mol_type = other DNA
                        organism = synthetic construct
SEQUENCE: 26
gtgaccaaga gctttaaccg gggggagtcc                                                30

SEQ ID NO: 27           moltype = DNA   length = 30
FEATURE                 Location/Qualifiers
misc_feature            1..30
                        note = primer 8
source                  1..30
                        mol_type = other DNA
                        organism = synthetic construct
SEQUENCE: 27
atcggcggcc gcgaagacgc ttttagatca                                                30

SEQ ID NO: 28           moltype = DNA   length = 30
FEATURE                 Location/Qualifiers
misc_feature            1..30
                        note = primer 9
source                  1..30
                        mol_type = other DNA
                        organism = synthetic construct
SEQUENCE: 28
tttaccgggg gcctgccgaa cccagttcat                                                30

SEQ ID NO: 29           moltype = DNA   length = 30
FEATURE                 Location/Qualifiers
misc_feature            1..30
                        note = primer 10
source                  1..30
                        mol_type = other DNA
                        organism = synthetic construct
SEQUENCE: 29
gcccccggta aatgtctgga atggatgggg                                                30

SEQ ID NO: 30           moltype = DNA   length = 30
FEATURE                 Location/Qualifiers
misc_feature            1..30
                        note = primer 11
source                  1..30
                        mol_type = other DNA
                        organism = synthetic construct
SEQUENCE: 30
atcggcggcc gcgaagacgc ttttagatca                                                30

SEQ ID NO: 31           moltype = DNA   length = 70
FEATURE                 Location/Qualifiers
misc_feature            1..70
                        note = primer 12
```

```
source                    1..70
                          mol_type = other DNA
                          organism = synthetic construct
SEQUENCE: 31
ttcatgcggc cgcgaagacg cttttagatc accgcttaat ctcaactttt gttccacatc    60
caaatgtcag                                                           70

SEQ ID NO: 32             moltype = DNA  length = 30
FEATURE                   Location/Qualifiers
misc_feature              1..30
                          note = primer 13
source                    1..30
                          mol_type = other DNA
                          organism = synthetic construct
SEQUENCE: 32
ttttccgggc atctgccgta cccacccaag                                     30

SEQ ID NO: 33             moltype = DNA  length = 36
FEATURE                   Location/Qualifiers
misc_feature              1..36
                          note = primer 14
source                    1..36
                          mol_type = other DNA
                          organism = synthetic construct
SEQUENCE: 33
atgcccggaa aatgtctcga ttggatagggg ataatg                             36

SEQ ID NO: 34             moltype = DNA  length = 70
FEATURE                   Location/Qualifiers
misc_feature              1..70
                          note = primer 15
source                    1..70
                          mol_type = other DNA
                          organism = synthetic construct
SEQUENCE: 34
ttcatgcggc cgcgaagacg cttttagatc accgctttat ctccaatttt gttccacacc    60
cgaatgtata                                                           70

SEQ ID NO: 35             moltype = DNA  length = 30
FEATURE                   Location/Qualifiers
misc_feature              1..30
                          note = primer 16
source                    1..30
                          mol_type = other DNA
                          organism = synthetic construct
SEQUENCE: 35
tttgcctggc atctgtcgaa cccatgcgat                                     30

SEQ ID NO: 36             moltype = DNA  length = 30
FEATURE                   Location/Qualifiers
misc_feature              1..30
                          note = primer 17
source                    1..30
                          mol_type = other DNA
                          organism = synthetic construct
SEQUENCE: 36
atgccaggca aatgtctgga gtccatgggg                                     30

SEQ ID NO: 37             moltype = DNA  length = 70
FEATURE                   Location/Qualifiers
misc_feature              1..70
                          note = primer 18
source                    1..70
                          mol_type = other DNA
                          organism = synthetic construct
SEQUENCE: 37
tacatgcggc cgcgaagacg cttttagatc aacgtttaat ctcaagtcga gtcccacacc    60
cgaaagtaat                                                           70

SEQ ID NO: 38             moltype = DNA  length = 465
FEATURE                   Location/Qualifiers
misc_feature              1..465
                          note = rhCD40L-his DNA
source                    1..465
                          mol_type = other DNA
                          organism = synthetic construct
SEQUENCE: 38
ggggatcaaa atcctcaaat cgctgctcac gtaattagtg aggcatcaag taagactacc    60
agcgtacttc aatgggccga gaagggctat tacactatgt caaacaacct cgtgaccctt    120
```

```
gagaacggca agcagctcac tgtaaagcgc cagggacttt attacattta tgcacaggtc    180
acattctgct caaaccggga ggcaagttca caggctccat ttatcgctag ttttgtgtttg   240
aagagcccag ggagatttga gaggatactt ctccgagccg caaacaccca ttccagtgcc    300
aagccatgcg ggcagcagag catacatttg ggtggcgtgt tgagctgca gcctggggca    360
tctgtattcg taaatgttac cgatccttct caagtttcac atggaacagg cttcacatct    420
ttcggccttc tgaaactggg ccaccaccat catcaccacc accat                    465

SEQ ID NO: 39           moltype = DNA  length = 351
FEATURE                 Location/Qualifiers
misc_feature            1..351
                        note = anti-IFNAR1 dsFv, VH DNA
source                  1..351
                        mol_type = other DNA
                        organism = synthetic construct
SEQUENCE: 39
gaagttcagc tggtacaatc aggagccgaa gtaaagaagc caggcgaatc ccttaaaatc    60
tcttgcaagg gaagcggcta catatttact aattactgga tcgcatgggt tcgacagatg    120
ccaggcaaat gtctggagtc catgggata atatacccgt gagacagtga catacgctat    180
tccccaagtt tccaaggaca agtgaccatt tctgctgata aaagcatcac aacagcctac    240
cttcaatggt catctcttaa ggcctctgac accgcaatgt actactgtgc tcgccacgat    300
attgaggggt tcgattactg ggggcggggc accttgtta cagttagcag t              351

SEQ ID NO: 40           moltype = DNA  length = 327
FEATURE                 Location/Qualifiers
misc_feature            1..327
                        note = anti-IFNAR1 dsFv, VL DNA
source                  1..327
                        mol_type = other DNA
                        organism = synthetic construct
SEQUENCE: 40
gagattgtac ttacccagtc tcctggcact ctgagtttga gtcccggcga gcgcgctacc    60
ctgagttgcc gagcttcaca gtccgtcagc tcttcattct tcgcttggta ccagcaaaaa    120
cctgggcagg ccccaagatt gcttatatat ggagcctcct cccgagcaac aggcatcccc    180
gaccgactca gcggttctgg atctggcacc gatttcactt tgacaattac ccggcttgag    240
cccgaggact tgccgtata ttattgtcaa caatacgata gcagcgcaat tactttcggg    300
tgtgggactc gacttgagat taaacgt                                        327

SEQ ID NO: 41           moltype = AA   length = 483
FEATURE                 Location/Qualifiers
REGION                  1..483
                        note = APB-A1 Heavy chain
source                  1..483
                        mol_type = protein
                        organism = synthetic construct
SEQUENCE: 41
DIVLTQSPAT LSVSPGERAT ISCRASQRVS SSTYSYMHWY QQKPGQPPKL LIKYASNLES    60
GVPARFSGSG SGTDFTLTIS SVEPEDFATY YCQHSWEIPP TFGGGTKLEI KRGGGGSGGG    120
GSGGGGSQVQ LVQSGAEVVK PGASVKLSCK ASGYIFTSYY MYWVKQAPGQ GLEWIGEINP    180
SNGDTNFNEK FKSKATLTVD KSASTAYMEL SSLRSEDTAV YYCTRSDGRN DMDSWGQGTL    240
VTVSSGGGGS GGGGSGGGGS QVQLVQSGGG PVKPGGSLRL SCAASGFMFR AYSMNWVRQA    300
PGKGLEWVSS ISSSGRYIHY ADSVKGRFTI SRDNAKNSLY LQMNSLRAED TAVYYCARET    360
VMAGKALDYW GQGTLVTVSS ASTKGPSVFP LAPSSKSTSE GTAALGCLVK DYFPEPVTVS    420
WNSGALTSGV HTFPAVLQSS GLYSLSSVVT VPSSSLGTQT YICNVNHKPS NTKVDKKVEP    480
KSS                                                                  483

SEQ ID NO: 42           moltype = AA   length = 478
FEATURE                 Location/Qualifiers
REGION                  1..478
                        note = APB-A1 Light chain
source                  1..478
                        mol_type = protein
                        organism = synthetic construct
SEQUENCE: 42
DIVLTQSPAT LSVSPGERAT ISCRASQRVS SSTYSYMHWY QQKPGQPPKL LIKYASNLES    60
GVPARFSGSG SGTDFTLTIS SVEPEDFATY YCQHSWEIPP TFGGGTKLEI KRGGGGSGGG    120
GSGGGGSQVQ LVQSGAEVVK PGASVKLSCK ASGYIFTSYY MYWVKQAPGQ GLEWIGEINP    180
SNGDTNFNEK FKSKATLTVD KSASTAYMEL SSLRSEDTAV YYCTRSDGRN DMDSWGQGTL    240
VTVSSGSTSG SGKPGSGEGS TKGDIVLTQS PGTLSLSPGE TATLSCRASQ SVGSNLAWYQ    300
QKPGQAPRLL IYGASTGATG VPARFSGSRS GTDFTLTITS LQPEDFATYY CQQYYSFLAK    360
TFGQGTQLEI KRTVAAPSVF IFPPSDEQLK SGTASVVCLL NNFYPREAKV QWKVDNALQS    420
GNSQESVTEQ DSKDSTYSLS NTLTLSKADY EKHKVYACEV THQGLSSPVT KSFNRGES      478

SEQ ID NO: 43           moltype = DNA  length = 735
FEATURE                 Location/Qualifiers
misc_feature            1..735
                        note = hu5c8 scFv DNA linked to N term of variable heavy
                         chain of SL335
```

```
source                  1..735
                        mol_type = other DNA
                        organism = synthetic construct
SEQUENCE: 43
gatatcgtgc tgacccagtc tcctgccaca ctgagtgtgt ctccaggcga gagagccacc    60
atctcttgca gagcttccca gagagtgtcc tcctccacct actcctacat gcactggtat   120
cagcagaagc ccggccagcc tcctaagctg ctgattaagt acgcctccaa cctggaatcc   180
ggcgtgccag ccagattttc tggctctgga tctggcaccg acttcaccct gaccatcagc   240
tctgtggaac ctgaggactt cgccacctac tactgccagc actcttggga gatcccacct   300
acctttggcg gaggcaccaa gctggaaatc aaaagaggtg gcggaggatc tggcggtggt   360
ggttcaggcg gaggcggatc tcaggttcag ttggttcagt ctggcgccga ggttgtgaaa   420
cctggcgctt ctgtgaagct gtcctgcaag gcctccggct acatcttcac cagctactac   480
atgtactggg tcaagcaggc ccctggacag ggacttgagt ggatcggcga gatcaaccct   540
tccaacggcg acaccaactt caacgagaag ttcaagtcca aggctaccct gaccgtggac   600
aagtctgcct ccaccgctta catggaactg tctagcctga aagcgagga caccgccgtg   660
tactactgca ccagatccga cggcagaaac gacatggatt cttggggcca gggcaccctg   720
gttacagttt cttct                                                     735

SEQ ID NO: 44           moltype = DNA  length = 735
FEATURE                 Location/Qualifiers
misc_feature            1..735
                        note = hu5c8 scFv DNA linked to N term of variable light
                         chain of SL335
source                  1..735
                        mol_type = other DNA
                        organism = synthetic construct
SEQUENCE: 44
gatatcgtgc tgacccagtc tcctgccaca ctgagtgtgt ctccaggcga gagagccacc    60
atctcttgca gagcttccca gagagtgtcc tcctccacct actcctacat gcactggtat   120
cagcagaagc ccggccagcc tcctaagctg ctgattaagt acgcctccaa cctggaatcc   180
ggcgtgccag ccagattttc tggctctgga tctggcaccg acttcaccct gaccatcagc   240
tctgtggaac ctgaggactt cgccacctac tactgccagc actcttggga gatcccacct   300
acctttggcg gaggcaccaa gctggaaatc aaaagaggtg gcggaggatc tggcggtggt   360
ggttcaggcg gaggcggatc tcaggttcag ttggttcagt ctggcgccga ggttgtgaaa   420
cctggcgctt ctgtgaagct gtcctgcaag gcctccggct acatcttcac cagctactac   480
atgtactggg tcaagcaggc ccctggacag ggacttgagt ggatcggcga gatcaaccct   540
tccaacggcg acaccaactt caacgagaag ttcaagtcca aggctaccct gaccgtggac   600
aagtctgcct ccaccgctta catggaactg tctagcctga aagcgagga caccgccgtg   660
tactactgca ccagatccga cggcagaaac gacatggatt cttggggcca gggcaccctg   720
gttacagtgt ccagt                                                     735

SEQ ID NO: 45           moltype = AA  length = 223
FEATURE                 Location/Qualifiers
REGION                  1..223
                        note = SL335 Heavy chain
source                  1..223
                        mol_type = protein
                        organism = synthetic construct
SEQUENCE: 45
QVQLVQSGGG PVKPGGSLRL SCAASGFMFR AYSMNWVRQA PGKGLEWVSS ISSSGRYIHY    60
ADSVKGRFTI SRDNAKNSLY LQMNSLRAED TAVYYCARET VMAGKALDYW GQGTLVTVSS   120
ASTKGPSVFP LAPSSKSTSE GTAALGCLVK DYFPEPVTVS WNSGALTSGV HTFPAVLQSS   180
GLYSLSSVVT VPSSSLGTQT YICNVNHKPS NTKVDKKVEP KSS                     223

SEQ ID NO: 46           moltype = AA  length = 215
FEATURE                 Location/Qualifiers
REGION                  1..215
                        note = SL335 Light chain
source                  1..215
                        mol_type = protein
                        organism = synthetic construct
SEQUENCE: 46
DIVLTQSPGT LSLSPGETAT LSCRASQSVG SNLAWYQQKP GQAPRLLIYG ASTGATGVPA    60
RFSGSRSGTD FTLTITSLQP EDFATYYCQQ YYSFLAKTFG QGTQLEIKRT VAAPSVFIFP   120
PSDEQLKSGT ASVVCLLNNF YPREAKVQWK VDNALQSGNS QESVTEQDSK DSTYSLSNTL   180
TLSKADYEKH KVYACEVTHQ GLSSPVTKSF NRGES                              215

SEQ ID NO: 47           moltype = AA  length = 245
FEATURE                 Location/Qualifiers
REGION                  1..245
                        note = hu5c8 scFv
source                  1..245
                        mol_type = protein
                        organism = synthetic construct
SEQUENCE: 47
DIVLTQSPAT LSVSPGERAT ISCRASQRVS SSTYSYMHWY QQKPGQPPKL LIKYASNLES    60
GVPARFSGSG SGTDFTLTIS SVEPEDFATY YCQHSWEIPP TFGQGTKLEI KRGGGGSGGG   120
```

```
GSGGGGSQVQ LVQSGAEVVK PGASVKLSCK ASGYIFTSYY MYWVKQAPGQ GLEWIGEINP     180
SNGDTNFNEK FKSKATLTVD KSASTAYMEL SSLRSEDTAV YYCTRSDGRN DMDSWGQGTL     240
VTVSS                                                                245

SEQ ID NO: 48           moltype = AA  length = 245
FEATURE                 Location/Qualifiers
REGION                  1..245
                        note = hu5c8 scFv linked to N term of variable heavy chain
                         of SL335
source                  1..245
                        mol_type = protein
                        organism = synthetic construct
SEQUENCE: 48
DIVLTQSPAT LSVSPGERAT ISCRASQRVS SSTYSMHWY QQKPGQPPKL LIKYASNLES      60
GVPARFSGSG SGTDFTLTIS SVEPEDFATY YCQHSWEIPP TFGGGTKLEI KRGGGGSGGG     120
GSGGGGSQVQ LVQSGAEVVK PGASVKLSCK ASGYIFTSYY MYWVKQAPGQ GLEWIGEINP     180
SNGDTNFNEK FKSKATLTVD KSASTAYMEL SSLRSEDTAV YYCTRSDGRN DMDSWGQGTL     240
VTVSS                                                                245

SEQ ID NO: 49           moltype = AA  length = 118
FEATURE                 Location/Qualifiers
REGION                  1..118
                        note = anti-TNF-alpha Fv, VH
source                  1..118
                        mol_type = protein
                        organism = synthetic construct
SEQUENCE: 49
EVQLVESGGG LVQPGGSLRL SCAASGYVFT DYGMNWVRQA PGKGLEWMGW INTYIGEPIY     60
ADSVKGRFTF SLDTSKSTAY LQMNSLRAED TAVYYCARGY RSYAMDYWGQ GTLVTVSS      118

SEQ ID NO: 50           moltype = AA  length = 108
FEATURE                 Location/Qualifiers
REGION                  1..108
                        note = anti-TNF-alpha Fv, VL
source                  1..108
                        mol_type = protein
                        organism = synthetic construct
SEQUENCE: 50
DIQMTQSPSS LSASVGDRVT ITCKASQNVG TNVAWYQQKP GKAPKALIYS ASFLYSGVPY     60
RFSGSGSGTD FTLTISSLQP EDFATYYCQQ YNIYPLTFGQ GTKVEIKR                 108

SEQ ID NO: 51           moltype = AA  length = 118
FEATURE                 Location/Qualifiers
REGION                  1..118
                        note = anti-TNF-alpha dsFv, VH
source                  1..118
                        mol_type = protein
                        organism = synthetic construct
SEQUENCE: 51
EVQLVESGGG LVQPGGSLRL SCAASGYVFT DYGMNWVRQA PGKCLEWMGW INTYIGEPIY     60
ADSVKGRFTF SLDTSKSTAY LQMNSLRAED TAVYYCARGY RSYAMDYWGQ GTLVTVSS      118

SEQ ID NO: 52           moltype = AA  length = 108
FEATURE                 Location/Qualifiers
REGION                  1..108
                        note = anti-TNF-alpha dsFv, VL
source                  1..108
                        mol_type = protein
                        organism = synthetic construct
SEQUENCE: 52
DIQMTQSPSS LSASVGDRVT ITCKASQNVG TNVAWYQQKP GKAPKALIYS ASFLYSGVPY     60
RFSGSGSGTD FTLTISSLQP EDFATYYCQQ YNIYPLTFGC GTKVEIKR                 108

SEQ ID NO: 53           moltype = AA  length = 119
FEATURE                 Location/Qualifiers
REGION                  1..119
                        note = anti-IL-23 Fv, VH
source                  1..119
                        mol_type = protein
                        organism = synthetic construct
SEQUENCE: 53
EVQLVQSGAE VKKPGESLKI SCKGSGYSFT TYWLGWVRQM PGKGLDWIGI MSPVDSDIRY     60
SPSFQGQVTM SVDKSITTAY LQWNSLKASD TAMYYCARRR PGQGYFDFWG QGTLVTVSS     119

SEQ ID NO: 54           moltype = AA  length = 108
FEATURE                 Location/Qualifiers
REGION                  1..108
                        note = anti-IL-23 Fv, VL
```

```
source                     1..108
                           mol_type = protein
                           organism = synthetic construct
SEQUENCE: 54
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNIYPYTFGQ GTKLEIKR                108

SEQ ID NO: 55              moltype = AA  length = 119
FEATURE                    Location/Qualifiers
REGION                     1..119
                           note = anti-IL-23 dsFv, VH
source                     1..119
                           mol_type = protein
                           organism = synthetic construct
SEQUENCE: 55
EVQLVQSGAE VKKPGESLKI SCKGSGYSFT TYWLGWVRQM PGKCLDWIGI MSPVDSDIRY    60
SPSFQGQVTM SVDKSITTAY LQWNSLKASD TAMYYCARRR PGQGYFDFWG QGTLVTVSS    119

SEQ ID NO: 56              moltype = AA  length = 108
FEATURE                    Location/Qualifiers
REGION                     1..108
                           note = anti-IL-23 dsFv, VL
source                     1..108
                           mol_type = protein
                           organism = synthetic construct
SEQUENCE: 56
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNIYPYTFGC GTKLEIKR                108

SEQ ID NO: 57              moltype = AA  length = 117
FEATURE                    Location/Qualifiers
REGION                     1..117
                           note = anti-IFNAR1 Fv, VH
source                     1..117
                           mol_type = protein
                           organism = synthetic construct
SEQUENCE: 57
EVQLVQSGAE VKKPGESLKI SCKGSGYIFT NYWIAWVRQM PGKGLESMGI IYPGDSDIRY    60
SPSFQGQVTI SADKSITTAY LQWSSLKASD TAMYYCARHD IEGFDYWGRG TLVTVSS      117

SEQ ID NO: 58              moltype = AA  length = 109
FEATURE                    Location/Qualifiers
REGION                     1..109
                           note = anti-IFNAR1 Fv, VL
source                     1..109
                           mol_type = protein
                           organism = synthetic construct
SEQUENCE: 58
EIVLTQSPGT LSLSPGERAT LSCRASQSVS SSFFAWYQQK PGQAPRLLIY GASSRATGIP    60
DRLSGSGSGT DFTLTITRLE PEDFAVYYCQ QYDSSAITFG QGTRLEIKR               109

SEQ ID NO: 59              moltype = AA  length = 117
FEATURE                    Location/Qualifiers
REGION                     1..117
                           note = anti-IFNAR1 dsFv, VH
source                     1..117
                           mol_type = protein
                           organism = synthetic construct
SEQUENCE: 59
EVQLVQSGAE VKKPGESLKI SCKGSGYIFT NYWIAWVRQM PGKCLESMGI IYPGDSDIRY    60
SPSFQGQVTI SADKSITTAY LQWSSLKASD TAMYYCARHD IEGFDYWGRG TLVTVSS      117

SEQ ID NO: 60              moltype = AA  length = 109
FEATURE                    Location/Qualifiers
REGION                     1..109
                           note = anti-IFNAR1 dsFv, VL
source                     1..109
                           mol_type = protein
                           organism = synthetic construct
SEQUENCE: 60
EIVLTQSPGT LSLSPGERAT LSCRASQSVS SSFFAWYQQK PGQAPRLLIY GASSRATGIP    60
DRLSGSGSGT DFTLTITRLE PEDFAVYYCQ QYDSSAITFG CGTRLEIKR               109

SEQ ID NO: 61              moltype = AA  length = 5
FEATURE                    Location/Qualifiers
REGION                     1..5
                           note = Anti-serum albumin VH CDR1
```

```
source                    1..5
                          mol_type = protein
                          organism = synthetic construct
SEQUENCE: 61
SYGIS                                                                  5

SEQ ID NO: 62             moltype = AA  length = 17
FEATURE                   Location/Qualifiers
REGION                    1..17
                          note = Anti-serum albumin VH CDR2
source                    1..17
                          mol_type = protein
                          organism = synthetic construct
SEQUENCE: 62
WINTYSGGTK YAQKFQG                                                    17

SEQ ID NO: 63             moltype = AA  length = 15
FEATURE                   Location/Qualifiers
REGION                    1..15
                          note = Anti-serum albumin VH CDR3
source                    1..15
                          mol_type = protein
                          organism = synthetic construct
SEQUENCE: 63
LGHCQRGICS DALDT                                                      15

SEQ ID NO: 64             moltype = AA  length = 17
FEATURE                   Location/Qualifiers
REGION                    1..17
                          note = Anti-serum albumin VH CDR2
source                    1..17
                          mol_type = protein
                          organism = synthetic construct
SEQUENCE: 64
RINTYNGNTG YAQRLQG                                                    17

SEQ ID NO: 65             moltype = AA  length = 5
FEATURE                   Location/Qualifiers
REGION                    1..5
                          note = Anti-serum albumin VH CDR1
source                    1..5
                          mol_type = protein
                          organism = synthetic construct
SEQUENCE: 65
NYGIH                                                                  5

SEQ ID NO: 66             moltype = AA  length = 17
FEATURE                   Location/Qualifiers
REGION                    1..17
                          note = Anti-serum albumin VH CDR2
source                    1..17
                          mol_type = protein
                          organism = synthetic construct
SEQUENCE: 66
SISYDGSNKY YADSVKG                                                    17

SEQ ID NO: 67             moltype = AA  length = 16
FEATURE                   Location/Qualifiers
REGION                    1..16
                          note = Anti-serum albumin VH CDR3
source                    1..16
                          mol_type = protein
                          organism = synthetic construct
SEQUENCE: 67
DVHYYGSGSY YNAFDI                                                     16

SEQ ID NO: 68             moltype = AA  length = 5
FEATURE                   Location/Qualifiers
REGION                    1..5
                          note = Anti-serum albumin VH CDR1
source                    1..5
                          mol_type = protein
                          organism = synthetic construct
SEQUENCE: 68
SYAMS                                                                  5
```

```
SEQ ID NO: 69           moltype = AA  length = 17
FEATURE                 Location/Qualifiers
REGION                  1..17
                        note = Anti-serum albumin VH CDR2
source                  1..17
                        mol_type = protein
                        organism = synthetic construct
SEQUENCE: 69
VISHDGGFQY YADSVKG                                                    17

SEQ ID NO: 70           moltype = AA  length = 11
FEATURE                 Location/Qualifiers
REGION                  1..11
                        note = Anti-serum albumin VH CDR3
source                  1..11
                        mol_type = protein
                        organism = synthetic construct
SEQUENCE: 70
AGWLRQYGMD V                                                          11

SEQ ID NO: 71           moltype = AA  length = 5
FEATURE                 Location/Qualifiers
REGION                  1..5
                        note = Anti-serum albumin VH CDR1
source                  1..5
                        mol_type = protein
                        organism = synthetic construct
SEQUENCE: 71
AYWIA                                                                  5

SEQ ID NO: 72           moltype = AA  length = 17
FEATURE                 Location/Qualifiers
REGION                  1..17
                        note = Anti-serum albumin VH CDR2
source                  1..17
                        mol_type = protein
                        organism = synthetic construct
SEQUENCE: 72
MIWPPDADAR YSPSFQG                                                    17

SEQ ID NO: 73           moltype = AA  length = 8
FEATURE                 Location/Qualifiers
REGION                  1..8
                        note = Anti-serum albumin VH CDR3
source                  1..8
                        mol_type = protein
                        organism = synthetic construct
SEQUENCE: 73
LYSGSYSP                                                               8

SEQ ID NO: 74           moltype = AA  length = 5
FEATURE                 Location/Qualifiers
REGION                  1..5
                        note = Anti-serum albumin VH CDR1
source                  1..5
                        mol_type = protein
                        organism = synthetic construct
SEQUENCE: 74
AYSMN                                                                  5

SEQ ID NO: 75           moltype = AA  length = 17
FEATURE                 Location/Qualifiers
REGION                  1..17
                        note = Anti-serum albumin VH CDR2
source                  1..17
                        mol_type = protein
                        organism = synthetic construct
SEQUENCE: 75
SISSSGRYIH YADSVKG                                                    17

SEQ ID NO: 76           moltype = AA  length = 11
FEATURE                 Location/Qualifiers
REGION                  1..11
                        note = Anti-serum albumin VH CDR3
source                  1..11
                        mol_type = protein
                        organism = synthetic construct
```

```
SEQUENCE: 76
ETVMAGKALD Y                                                                    11

SEQ ID NO: 77         moltype = AA  length = 11
FEATURE               Location/Qualifiers
REGION                1..11
                      note = Anti-serum albumin VL CDR1
source                1..11
                      mol_type = protein
                      organism = synthetic construct
SEQUENCE: 77
RASQSISRYL N                                                                    11

SEQ ID NO: 78         moltype = AA  length = 7
FEATURE               Location/Qualifiers
REGION                1..7
                      note = Anti-serum albumin VL CDR2
source                1..7
                      mol_type = protein
                      organism = synthetic construct
SEQUENCE: 78
GASRLES                                                                          7

SEQ ID NO: 79         moltype = AA  length = 9
FEATURE               Location/Qualifiers
REGION                1..9
                      note = Anti-serum albumin VL CDR3
source                1..9
                      mol_type = protein
                      organism = synthetic construct
SEQUENCE: 79
QQSDSVPVT                                                                        9

SEQ ID NO: 80         moltype = AA  length = 11
FEATURE               Location/Qualifiers
REGION                1..11
                      note = Anti-serum albumin VL CDR1
source                1..11
                      mol_type = protein
                      organism = synthetic construct
SEQUENCE: 80
RASQSISSYL N                                                                    11

SEQ ID NO: 81         moltype = AA  length = 7
FEATURE               Location/Qualifiers
REGION                1..7
                      note = Anti-serum albumin VL CDR2
source                1..7
                      mol_type = protein
                      organism = synthetic construct
SEQUENCE: 81
AASSLQS                                                                          7

SEQ ID NO: 82         moltype = AA  length = 10
FEATURE               Location/Qualifiers
REGION                1..10
                      note = Anti-serum albumin VL CDR3
source                1..10
                      mol_type = protein
                      organism = synthetic construct
SEQUENCE: 82
QQSYSTPPYT                                                                      10

SEQ ID NO: 83         moltype = AA  length = 11
FEATURE               Location/Qualifiers
REGION                1..11
                      note = Anti-serum albumin VL CDR1
source                1..11
                      mol_type = protein
                      organism = synthetic construct
SEQUENCE: 83
RASQSIFNYV A                                                                    11

SEQ ID NO: 84         moltype = AA  length = 7
FEATURE               Location/Qualifiers
REGION                1..7
                      note = Anti-serum albumin VL CDR2
```

```
source                  1..7
                        mol_type = protein
                        organism = synthetic construct
SEQUENCE: 84
DASNRAT                                                                 7

SEQ ID NO: 85           moltype = AA   length = 11
FEATURE                 Location/Qualifiers
REGION                  1..11
                        note = Anti-serum albumin VL CDR3
source                  1..11
                        mol_type = protein
                        organism = synthetic construct
SEQUENCE: 85
QQRSKWPPTW T                                                           11

SEQ ID NO: 86           moltype = AA   length = 12
FEATURE                 Location/Qualifiers
REGION                  1..12
                        note = Anti-serum albumin VL CDR1
source                  1..12
                        mol_type = protein
                        organism = synthetic construct
SEQUENCE: 86
RASETVSSRQ LA                                                          12

SEQ ID NO: 87           moltype = AA   length = 7
FEATURE                 Location/Qualifiers
REGION                  1..7
                        note = Anti-serum albumin VL CDR2
source                  1..7
                        mol_type = protein
                        organism = synthetic construct
SEQUENCE: 87
GASSRAT                                                                 7

SEQ ID NO: 88           moltype = AA   length = 9
FEATURE                 Location/Qualifiers
REGION                  1..9
                        note = Anti-serum albumin VL CDR3
source                  1..9
                        mol_type = protein
                        organism = synthetic construct
SEQUENCE: 88
QQYGSSPRT                                                               9

SEQ ID NO: 89           moltype = AA   length = 12
FEATURE                 Location/Qualifiers
REGION                  1..12
                        note = Anti-serum albumin VL CDR1
source                  1..12
                        mol_type = protein
                        organism = synthetic construct
SEQUENCE: 89
RASQSVSSSS LA                                                          12

SEQ ID NO: 90           moltype = AA   length = 9
FEATURE                 Location/Qualifiers
REGION                  1..9
                        note = Anti-serum albumin VL CDR3
source                  1..9
                        mol_type = protein
                        organism = synthetic construct
SEQUENCE: 90
QKYSSYPLT                                                               9

SEQ ID NO: 91           moltype = AA   length = 11
FEATURE                 Location/Qualifiers
REGION                  1..11
                        note = Anti-serum albumin VL CDR1
source                  1..11
                        mol_type = protein
                        organism = synthetic construct
SEQUENCE: 91
RASQSVGSNL A                                                           11
```

```
SEQ ID NO: 92            moltype = AA  length = 7
FEATURE                  Location/Qualifiers
REGION                   1..7
                         note = Anti-serum albumin VL CDR2
source                   1..7
                         mol_type = protein
                         organism = synthetic construct
SEQUENCE: 92
GASTGAT                                                                    7

SEQ ID NO: 93            moltype = AA  length = 10
FEATURE                  Location/Qualifiers
REGION                   1..10
                         note = Anti-serum albumin VL CDR3
source                   1..10
                         mol_type = protein
                         organism = synthetic construct
SEQUENCE: 93
QQYYSFLAKT                                                                10

SEQ ID NO: 94            moltype = AA  length = 124
FEATURE                  Location/Qualifiers
REGION                   1..124
                         note = Anti-serum albumin, heavy chain variable domain (VH
                         domain)
source                   1..124
                         mol_type = protein
                         organism = synthetic construct
SEQUENCE: 94
QVQLLQSGAE VKKPGASVKV SCKASGYTFT SYGISWVRQA PGQGLEWVGW INTYSGGTKY          60
AQKFQGRVTM TRDTSISTVY MELSGLKSDD TAVYYCARLG HCQRGICSDA LDTWGQGTLV        120
TVSS                                                                    124

SEQ ID NO: 95            moltype = AA  length = 124
FEATURE                  Location/Qualifiers
REGION                   1..124
                         note = Anti-serum albumin, heavy chain variable domain (VH
                         domain)
source                   1..124
                         mol_type = protein
                         organism = synthetic construct
SEQUENCE: 95
EVQLLQSGAE VKEPGASVKV SCKASGYTFS SYGISWVRQA PGQGLEWVGR INTYNGNTGY          60
AQRLQGRVTM TTDTSTSIAY MEVRSLRSDD TAVYYCARLG HCQRGICSDA LDTWGQGTMV        120
TVSS                                                                    124

SEQ ID NO: 96            moltype = AA  length = 125
FEATURE                  Location/Qualifiers
REGION                   1..125
                         note = Anti-serum albumin, heavy chain variable domain (VH
                         domain)
source                   1..125
                         mol_type = protein
                         organism = synthetic construct
SEQUENCE: 96
QVQLVQSGGG VVQTGGSLRL SCAASGFTFR NYGIHWVRQA PGKGLEWVAS ISYDGSNKYY          60
ADSVKGRFTI SRDNSRNTVH VQMDSLRGGD TAVYYCARDV HYYGSGSYYN AFDIWGQGTL        120
VTVSS                                                                   125

SEQ ID NO: 97            moltype = AA  length = 120
FEATURE                  Location/Qualifiers
REGION                   1..120
                         note = Anti-serum albumin, heavy chain variable domain (VH
                         domain)
source                   1..120
                         mol_type = protein
                         organism = synthetic construct
SEQUENCE: 97
QVQLVQSGGG LVQPGGSLRL SCAASGFTFS SYAMSWVRQA PGKGLEWLSV ISHDGGFQYY          60
ADSVKGRFTV SRDNSKNTLY LQMNSLRAED TAVYYCARAG WLRQYGMDVW GQGTLVTVSS        120

SEQ ID NO: 98            moltype = AA  length = 117
FEATURE                  Location/Qualifiers
REGION                   1..117
                         note = Anti-serum albumin, heavy chain variable domain (VH
                         domain)
```

```
source                  1..117
                        mol_type = protein
                        organism = synthetic construct
SEQUENCE: 98
EVQLVQSGTE VKKPGESLKI SCKISGYSFT AYWIAWVRQM PGKGLEWMGM IWPPDADARY    60
SPSFQGQVTF SVDKSISTAY LQWHSLKTSD TAVYYCARLY SGSYSPWGQG TLVTVSS      117

SEQ ID NO: 99           moltype = AA  length = 120
FEATURE                 Location/Qualifiers
REGION                  1..120
                        note = Anti-serum albumin, heavy chain variable domain (VH
                        domain)
source                  1..120
                        mol_type = protein
                        organism = synthetic construct
SEQUENCE: 99
QVQLVQSGGG PVKPGGSLRL SCAASGFMFR AYSMNWVRQA PGKGLEWVSS ISSSGRYIHY    60
ADSVKGRFTI SRDNAKNSLY LQMNSLRAED TAVYYCARET VMAGKALDYW GQGTLVTVSS   120

SEQ ID NO: 100          moltype = AA  length = 108
FEATURE                 Location/Qualifiers
REGION                  1..108
                        note = Anti-serum albumin, light chain variable domain (VL
                        domain)
source                  1..108
                        mol_type = protein
                        organism = synthetic construct
SEQUENCE: 100
ELVLTQSPSS LSASVGDRVT ITCRASQSIS RYLNWYQQKP GKAPKLLIYG ASRLESGVPS    60
RFSGSGSGTD FTLTISSLQP EDFATYYCQQ SDSVPVTFGQ GTRLEIKR                108

SEQ ID NO: 101          moltype = AA  length = 109
FEATURE                 Location/Qualifiers
REGION                  1..109
                        note = Anti-serum albumin, light chain variable domain (VL
                        domain)
source                  1..109
                        mol_type = protein
                        organism = synthetic construct
SEQUENCE: 101
DIVLTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPYTFG QGTKLEIKR               109

SEQ ID NO: 102          moltype = AA  length = 110
FEATURE                 Location/Qualifiers
REGION                  1..110
                        note = Anti-serum albumin, light chain variable domain (VL
                        domain)
source                  1..110
                        mol_type = protein
                        organism = synthetic construct
SEQUENCE: 102
ELVLTQSPGT LSLSPGERAT LSCRASQSIF NYVAWYQQKP GQAPRLLIYD ASNRATGIPA    60
RFSGSGSGTD FTLTISSLEP EDFAVYYCQQ RSKWPPTWTF GQGTRVDIKR              110

SEQ ID NO: 103          moltype = AA  length = 109
FEATURE                 Location/Qualifiers
REGION                  1..109
                        note = Anti-serum albumin, light chain variable domain (VL
                        domain)
source                  1..109
                        mol_type = protein
                        organism = synthetic construct
SEQUENCE: 103
ELVLTQSPGT LSLSPGERAT LSCRASETVS SRQLAWYQQK PGQAPRLLIY GASSRATGIP    60
DRFSGSGSGT DFTLTISRLE PEDSAVFYCQ QYGSSPRTFG GGTKLEIKR               109

SEQ ID NO: 104          moltype = AA  length = 109
FEATURE                 Location/Qualifiers
REGION                  1..109
                        note = Anti-serum albumin, light chain variable domain (VL
                        domain)
source                  1..109
                        mol_type = protein
                        organism = synthetic construct
SEQUENCE: 104
ELVLTQSPGT LSLSPGERAT LSCRASQSVS SSSLAWYQQK PGQAPRLLIY GASSRATGIP    60
DRFSGSGSGT DFTLTISSLQ PEDAATYYCQ KYSSYPLTFG QGTKLEIKR               109
```

```
SEQ ID NO: 105          moltype = AA   length = 109
FEATURE                 Location/Qualifiers
REGION                  1..109
                        note = Anti-serum albumin, light chain variable domain (VL
                         domain)
source                  1..109
                        mol_type = protein
                        organism = synthetic construct
SEQUENCE: 105
ELVLTQSPGT LSLSPGETAT LSCRASQSVG SNLAWYQQKP GQAPRLLIYG ASTGATGVPA   60
RFSGSRSGTD FTLTITSLQP EDFATYYCQQ YYSFLAKTFG QGTQLEIKR              109

SEQ ID NO: 106          moltype = AA   length = 616
FEATURE                 Location/Qualifiers
REGION                  1..616
                        note = APB-B1 heavy chain
source                  1..616
                        mol_type = protein
                        organism = synthetic construct
SEQUENCE: 106
DIVLTQSPAT LSVSPGERAT ISCRASQRVS SSTYSYMHWY QQKPGQPPKL LIKYASNLES   60
GVPARFSGSG SGTDFTLTIS SVEPEDFATY YCQHSWEIPP TFGQGTKLEI KRGGGGSGGG   120
GSGGGGSQVQ LVQSGAEVVK PGASVKLSCK ASGYIFTSYY MYWVKQAPGQ GLEWIGEINP   180
SNGDTNFNEK FKSKATLTVD KSASTAYMEL SSLRSEDTAV YYCTRSDGRN DMDSWGQGTL   240
VTVSSGGGGS GGGGSGGGGS QVQLVQSGGG PVKPGGSLRL SCAASGFMFR AYSMNWVRQA   300
PGKGLEWVSS ISSSGRYIHY ADSVKGRFTI SRDNAKNSLY LQMNSLRAED TAVYYCARET   360
VMAGKALDYW GQGTLVTVSS ASTKGPSVFP LAPSSKSTSE GTAALGCLVK DYFPEPVTVS   420
WNSGALTSGV HTFPAVLQSS GLYSLSSVVT VPSSSLGTQT YICNVNHKPS NTKVDKKVEP   480
KSSGGGGSGG GGSGGGGSEV QLVESGGGLV QPGGSLRLSC AASGYVFTDY GMNWVRQAPG   540
KGLEWMGWIN TYIGEPIYAD SVKGRFTFSL DTSKSTAYLQ MNSLRAEDTA VYYCARGYRS   600
YAMDYWGQGT LVTVSS                                                   616

SEQ ID NO: 107          moltype = AA   length = 601
FEATURE                 Location/Qualifiers
REGION                  1..601
                        note = APB-B1 light chain
source                  1..601
                        mol_type = protein
                        organism = synthetic construct
SEQUENCE: 107
DIVLTQSPAT LSVSPGERAT ISCRASQRVS SSTYSYMHWY QQKPGQPPKL LIKYASNLES   60
GVPARFSGSG SGTDFTLTIS SVEPEDFATY YCQHSWEIPP TFGQGTKLEI KRGGGGSGGG   120
GSGGGGSQVQ LVQSGAEVVK PGASVKLSCK ASGYIFTSYY MYWVKQAPGQ GLEWIGEINP   180
SNGDTNFNEK FKSKATLTVD KSASTAYMEL SSLRSEDTAV YYCTRSDGRN DMDSWGQGTL   240
VTVSSGGSTSG SGKPGSGEGS TKGDIVLTQS PGTLSLSPGE TATLSCRASQ SVGSNLAWYQ   300
QKPGQAPRLL IYGASTGATG VPARFSGSRS GTDFTLTITS LQPEDFATYY CQQYYSFLAK   360
TFGQGTQLEI KRTVAAPSVF IFPPSDEQLK SGTASVVCLL NNFYPREAKV QWKVDNALQS   420
GNSQESVTEQ DSKDSTYSLS NTLTLSKADY EKHKVYACEV THQGLSSPVT KSFNRGESGG   480
GGSGGGGSGG GGSDIQMTQS PSSLSASVGD RVTITCKASQ NVGTNVAWYQ QKPGKAPKAL   540
IYSASFLYSG VPYRFSGSGS GTDFTLTISS LQPEDFATYY CQQYNIYPLT FGQGTKVEIK   600
R                                                                   601
```

What is claimed is:

1. A multispecific antibody comprising a structural formula of:

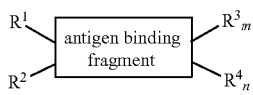

wherein the antigen binding fragment is a serum albumin Fab comprising
a heavy chain complementarity determining domain 1 (CDR1) comprising the amino acid sequence of AYSMN (SEQ ID NO:74), a heavy chain CDR2 comprising the amino acid sequence of SISSSGRYIHYADSVKG (SEQ ID NO:75), and a heavy chain CDR3 comprising the amino acid sequence of ETVMAGKALDY (SEQ ID NO:76), and
a light chain complementarity determining domain 1 (CDR1) comprising the amino acid sequence of RASQSVGSNLA (SEQ ID NO:91), a light chain CDR2 comprising the amino acid sequence of GASTGAT (SEQ ID NO:92), and a light chain CDR3 comprising the amino acid sequence of QQYYSFLAKT (SEQ ID NO:93);
wherein $R^1$ and $R^2$ are bioactive effector moieties linked to an N-terminus of the Fab, each linked to a heavy chain variable domain or a light chain variable domain of the Fab, wherein each of the $R^1$ and $R^2$ is an anti-CD40L hu5c8 scFv comprising an amino acid sequence of SEQ ID NO:48;
wherein $R^3$ and $R^4$ are bioactive effector moieties linked to a C-terminus of the Fab, each linked to a heavy chain variable domain or a light chain variable domain of the Fab;
wherein m is 0; and
wherein n is 0.

2. The multispecific antibody of claim 1, wherein each of $R^1$ and $R^2$ is linked to the Fab by one or more linkers.

3. The multispecific antibody of claim 1, wherein the Fab comprises a heavy chain variable domain comprising an amino acid sequence having at least 98% identity to SEQ ID NO: 99.

4. The multispecific antibody of claim 1, wherein the Fab comprises a heavy chain variable domain comprising an amino acid sequence of SEQ ID NO: 99.

5. The multispecific antibody of claim 1, wherein the Fab comprises a light chain variable domain comprising an amino acid sequence having at least 98% identity to SEQ ID NO: 105.

6. The multispecific antibody of claim 1, wherein the Fab comprises a heavy chain variable domain comprising an amino acid sequence having at least 98% identity to SEQ ID NO: 99, and a light chain variable domain comprising an amino acid sequence having at least 98% identity to SEQ ID NO: 105.

7. The multispecific antibody of claim 1, wherein the Fab comprises a heavy chain domain comprising an amino acid sequence of SEQ ID NO:45 ($V_H$-$C_{H1}$ domain) and a light chain domain comprising an amino acid sequence of SEQ ID NO:46 ($V_L$-$C_L$ domain).

8. The multispecific antibody of claim 2, wherein each linker comprises 1 to 20 amino acids.

9. The multispecific antibody of claim 2, wherein each linker comprises an amino acid sequence having at least 90% identity to SEQ ID NO:3 or SEQ ID NO:4.

10. The multispecific antibody of claim 1, wherein the multispecific antibody comprises a heavy chain comprising an amino acid sequence of SEQ ID NO:41, and a light chain comprising an amino acid sequence of SEQ ID NO:42.

11. A multispecific antibody comprising a structural formula of:

wherein the antigen binding fragment is a serum albumin Fab comprising
a heavy chain complementarity determining domain 1 (CDR1) comprising the amino acid sequence of AYSMN (SEQ ID NO:74), a heavy chain CDR2 comprising the amino acid sequence of SISSSGRYIHY-ADSVKG (SEQ ID NO:75), and a heavy chain CDR3 comprising the amino acid sequence of ETVMAGKA-LDY (SEQ ID NO:76), and
a light chain complementarity determining domain 1 (CDR1) comprising the amino acid sequence of RASQSVGSNLA (SEQ ID NO:91), a light chain CDR2 comprising the amino acid sequence of GAST-GAT (SEQ ID NO:92), and a light chain CDR3 comprising the amino acid sequence of QQYYSFLAKT (SEQ ID NO:93);
wherein $R^1$ and $R^2$ are bioactive effector moieties linked to an N-terminus of the Fab, each linked to a heavy chain variable domain or a light chain variable domain of the Fab, wherein each of the $R^1$ and $R^2$ is an anti-CD40L hu5c8 scFv comprising an amino acid sequence of SEQ ID NO:48;
wherein $R^3$ and $R^4$ are bioactive effector moieties linked to a C-terminus of the Fab, each linked to a heavy chain variable domain or a light chain variable domain of the Fab;
wherein m is 0;
wherein n is 0; and
wherein each of $R^1$ and $R^2$ is linked to the Fab by one or more linkers, wherein each linker comprises an amino acid sequence of SEQ ID NO:3 or SEQ ID NO:4.

12. The multispecific antibody of claim 11, wherein the Fab comprises a heavy chain variable domain comprising an amino acid sequence having at least 98% identity to SEQ ID NO: 99.

13. The multispecific antibody of claim 11, wherein the Fab comprises a heavy chain variable domain comprising an amino acid sequence of SEQ ID NO: 99.

14. The multispecific antibody of claim 11, wherein the Fab comprises a light chain variable domain comprising an amino acid sequence having at least 98% identity to SEQ ID NO: 105.

15. The multispecific antibody of claim 11, wherein the Fab comprises a heavy chain variable domain comprising an amino acid sequence having at least 98% identity to SEQ ID NO: 99, and a light chain variable domain comprising an amino acid sequence having at least 98% identity to SEQ ID NO: 105.

16. The multispecific antibody of claim 11, wherein the Fab comprises a heavy chain domain comprising an amino acid sequence of SEQ ID NO:45 ($V_H$-$C_{H1}$ domain) and a light chain domain comprising an amino acid sequence of SEQ ID NO:46 ($V_L$-$C_L$ domain).

17. The multispecific antibody of claim 11, wherein the multispecific antibody comprises a heavy chain comprising an amino acid sequence of SEQ ID NO:41, and a light chain comprising an amino acid sequence of SEQ ID NO:42.

18. A pharmaceutical composition comprising the multispecific antibody of claim 1 and a pharmaceutically acceptable excipient.

19. A pharmaceutical composition comprising the multispecific antibody of claim 11 and a pharmaceutically acceptable excipient.

* * * * *